US012714556B2

(12) United States Patent
Dienno et al.

(10) Patent No.: US 12,714,556 B2
(45) Date of Patent: Aug. 25, 2026

(54) PROSTHETIC VALVES WITH MECHANICALLY COUPLED LEAFLETS

(71) Applicant: EDWARDS LIFESCIENCES CORPORATION, Irvine, CA (US)

(72) Inventors: Dustin V. Dienno, Flagstaff, AZ (US); Cody L. Hartman, Flagstaff, AZ (US); Ryan S. Titone, Flagstaff, AZ (US); David J. Arcaro, Flagstaff, AZ (US); Roy Manygoats, Jr., Flagstaff, AZ (US)

(73) Assignee: Edwards Lifesciences Corporation, Irvine, CA (US)

(*) Notice: Subject to any disclaimer, the term of this patent is extended or adjusted under 35 U.S.C. 154(b) by 0 days.

(21) Appl. No.: 18/630,501

(22) Filed: Apr. 9, 2024

(65) Prior Publication Data

US 2024/0252314 A1 Aug. 1, 2024

Related U.S. Application Data

(63) Continuation of application No. 17/377,091, filed on Jul. 15, 2021, now Pat. No. 11,986,387, which is a (Continued)

(51) Int. Cl.
*A61F 2/24* (2006.01)
*A61L 27/16* (2006.01)
(Continued)

(52) U.S. Cl.
CPC .......... *A61F 2/2412* (2013.01); *A61F 2/2418* (2013.01); *A61F 2/2433* (2013.01); (Continued)

(58) Field of Classification Search
CPC ............ A61F 2/24–2424; A61F 2/2475; A61F 2230/0026
See application file for complete search history.

(56) References Cited

U.S. PATENT DOCUMENTS 654,799 A 7/1900 Levett
3,739,402 A 6/1973 Kahn et al.
(Continued)

FOREIGN PATENT DOCUMENTS

CA 2462509 A1 4/2003
CN 101057796 A 10/2007
(Continued)

OTHER PUBLICATIONS

Clough N., et al., “Introducing a New Family of GORE (Trademark) ePTFE Fibers,” 2007, pp. 1-10.
(Continued)

*Primary Examiner* — Rebecca S Preston
(74) *Attorney, Agent, or Firm* — Klarquist Sparkman LLP

(57) ABSTRACT

Described embodiments are directed toward centrally-opening leaflet prosthetic valve devices having a leaflet frame and a mechanically coupled leaflet. The described leaflet frames have projections that are configured to couple with a leaflet attachment region of a leaflet. Some embodiments include a leaflet retention feature that engages the leaflet frame projections and operates to secure the leaflet to the leaflet frame. Methods of making and using such prosthetic valve devices are also described.

14 Claims, 41 Drawing Sheets

Related U.S. Application Data continuation of application No. 16/129,682, filed on Sep. 12, 2018, now Pat. No. 11,109,963.

(60) Provisional application No. 62/579,753, filed on Oct. 31, 2017, provisional application No. 62/572,274, filed on Oct. 13, 2017, provisional application No. 62/564,031, filed on Sep. 27, 2017.

(51) Int. Cl.
*A61L 27/18* (2006.01)
*A61L 27/56* (2006.01)

(52) U.S. Cl.
CPC .......... *A61F 2/2415* (2013.01); *A61F 2/2436* (2013.01); *A61F 2/246* (2013.01); *A61F 2/2463* (2013.01); *A61F 2/2466* (2013.01); *A61F 2210/0014* (2013.01); *A61F 2220/0016* (2013.01); *A61F 2220/0033* (2013.01); *A61F 2220/005* (2013.01); *A61F 2220/0075* (2013.01); *A61F 2220/0083* (2013.01); *A61F 2230/0013* (2013.01); *A61F 2230/0023* (2013.01); *A61F 2230/0026* (2013.01); *A61F 2230/0043* (2013.01); *A61F 2230/0052* (2013.01); *A61F 2230/0069* (2013.01); *A61F 2250/0069* (2013.01); *A61L 27/16* (2013.01); *A61L 27/18* (2013.01); *A61L 27/56* (2013.01); *A61L 2430/20* (2013.01)

(56) References Cited

U.S. PATENT DOCUMENTS

| | | | |
|---|---|---|---|
| 3,953,566 | A | 4/1976 | Gore |
| 4,178,639 | A | 12/1979 | Bokros |
| 4,187,390 | A | 2/1980 | Gore |
| 4,222,126 | A | 9/1980 | Boretos et al. |
| 4,265,694 | A | 5/1981 | Boretos et al. |
| 4,332,035 | A | 6/1982 | Mano |
| 4,340,091 | A | 7/1982 | Skelton et al. |
| 4,477,930 | A | 10/1984 | Totten et al. |
| 4,556,996 | A | 12/1985 | Wallace |
| 4,626,255 | A | 12/1986 | Reichart et al. |
| 4,759,759 | A | 7/1988 | Walker et al. |
| 4,851,000 | A | 7/1989 | Gupta |
| 4,877,661 | A | 10/1989 | House et al. |
| 4,955,899 | A | 9/1990 | Della, V et al. |
| 5,026,513 | A | 6/1991 | House et al. |
| 5,064,435 | A | 11/1991 | Porter |
| 5,071,609 | A | 12/1991 | Tu et al. |
| 5,123,918 | A | 6/1992 | Perrier et al. |
| 5,163,955 | A | 11/1992 | Love et al. |
| 5,415,667 | A | 5/1995 | Frater |
| 5,469,868 | A | 11/1995 | Reger |
| 5,476,589 | A | 12/1995 | Bacino |
| 5,489,297 | A | 2/1996 | Duran |
| 5,534,007 | A | 7/1996 | St et al. |
| 5,549,663 | A | 8/1996 | Cottone, Jr. |
| 5,554,183 | A | 9/1996 | Nazari |
| 5,562,729 | A | 10/1996 | Purdy et al. |
| 5,628,791 | A | 5/1997 | Bokros et al. |
| 5,673,102 | A | 9/1997 | Suzuki et al. |
| 5,708,044 | A | 1/1998 | Branca |
| 5,718,973 | A | 2/1998 | Lewis et al. |
| 5,749,852 | A | 5/1998 | Schwab et al. |
| 5,752,934 | A | 5/1998 | Campbell et al. |
| 5,759,192 | A | 6/1998 | Saunders |
| 5,772,884 | A | 6/1998 | Tanaka et al. |
| 5,814,405 | A | 9/1998 | Branca et al. |
| 5,824,043 | A | 10/1998 | Cottone, Jr. |
| 5,843,158 | A | 12/1998 | Lenker et al. |
| 5,843,161 | A | 12/1998 | Solovay |
| 5,843,171 | A | 12/1998 | Campbell et al. |
| 5,853,419 | A | 12/1998 | Imran |
| 5,925,061 | A | 7/1999 | Ogi et al. |
| 5,928,281 | A | 7/1999 | Huynh et al. |
| 5,935,162 | A | 8/1999 | Dang |
| 5,935,163 | A | 8/1999 | Gabbay |
| 5,944,654 | A | 8/1999 | Crawford |
| 5,957,974 | A | 9/1999 | Thompson et al. |
| 6,010,529 | A | 1/2000 | Herweck et al. |
| 6,013,854 | A | 1/2000 | Moriuchi |
| 6,019,785 | A | 2/2000 | Strecker |
| 6,042,588 | A | 3/2000 | Munsinger et al. |
| 6,042,606 | A | 3/2000 | Frantzen |
| 6,086,612 | A | 7/2000 | Jansen |
| 6,110,198 | A | 8/2000 | Fogarty et al. |
| 6,117,169 | A | 9/2000 | Moe |
| 6,129,758 | A | 10/2000 | Love |
| 6,161,399 | A | 12/2000 | Jayaraman |
| 6,171,335 | B1 | 1/2001 | Wheatley et al. |
| 6,174,329 | B1 | 1/2001 | Callol et al. |
| 6,174,331 | B1 | 1/2001 | Moe et al. |
| 6,190,406 | B1 | 2/2001 | Duerig et al. |
| 6,197,143 | B1 | 3/2001 | Bodnar |
| 6,217,609 | B1 | 4/2001 | Haverkost |
| 6,245,012 | B1 | 6/2001 | Kleshinski |
| 6,261,320 | B1 | 7/2001 | Tam et al. |
| 6,261,620 | B1 | 7/2001 | Leadbeater |
| 6,283,995 | B1 | 9/2001 | Moe et al. |
| 6,287,334 | B1 | 9/2001 | Moll et al. |
| 6,328,763 | B1 | 12/2001 | Love et al. |
| 6,352,552 | B1 | 3/2002 | Levinson et al. |
| 6,379,382 | B1 | 4/2002 | Yang |
| 6,454,799 | B1 | 9/2002 | Schreck |
| 6,461,665 | B1 | 10/2002 | Scholander |
| 6,482,228 | B1 | 11/2002 | Norred |
| 6,488,701 | B1 | 12/2002 | Nolting et al. |
| 6,541,589 | B1 | 4/2003 | Baillie |
| 6,558,418 | B2 | 5/2003 | Carpentier et al. |
| 6,582,464 | B2 | 6/2003 | Gabbay |
| 6,613,086 | B1 | 9/2003 | Moe et al. |
| 6,620,190 | B1 | 9/2003 | Colone |
| 6,626,939 | B1 | 9/2003 | Burnside et al. |
| 6,645,244 | B2 | 11/2003 | Shu et al. |
| 6,673,102 | B1 | 1/2004 | Vonesh et al. |
| 6,673,107 | B1 | 1/2004 | Brandt et al. |
| 6,726,715 | B2 | 4/2004 | Sutherland |
| 6,730,120 | B2 | 5/2004 | Berg et al. |
| 6,755,856 | B2 | 6/2004 | Fierens et al. |
| 6,755,857 | B2 | 6/2004 | Peterson et al. |
| 6,758,858 | B2 | 7/2004 | Mccrea et al. |
| 6,890,350 | B1 | 5/2005 | Walak |
| 6,916,338 | B2 | 7/2005 | Speziali |
| 6,936,067 | B2 | 8/2005 | Buchanan |
| 7,049,380 | B1 | 5/2006 | Chang et al. |
| 7,083,642 | B2 | 8/2006 | Sirhan et al. |
| 7,105,018 | B1 | 9/2006 | Yip et al. |
| 7,137,184 | B2 | 11/2006 | Schreck |
| 7,163,556 | B2 | 1/2007 | Xie et al. |
| 7,247,167 | B2 | 7/2007 | Gabbay |
| 7,419,678 | B2 | 9/2008 | Falotico |
| 7,513,909 | B2 | 4/2009 | Lane et al. |
| 7,531,611 | B2 | 5/2009 | Sabol et al. |
| 7,563,277 | B2 | 7/2009 | Case et al. |
| 7,727,274 | B2 | 6/2010 | Zilla et al. |
| 7,758,640 | B2 | 7/2010 | Vesely |
| 7,811,314 | B2 | 10/2010 | Fierens et al. |
| 7,815,763 | B2 | 10/2010 | Fierens et al. |
| 7,879,085 | B2 | 2/2011 | Sowinski et al. |
| 7,887,562 | B2 | 2/2011 | Young et al. |
| 7,927,364 | B2 | 4/2011 | Fierens et al. |
| 7,927,365 | B2 | 4/2011 | Fierens et al. |
| 8,048,440 | B2 | 11/2011 | Chang et al. |
| 8,092,523 | B2 | 1/2012 | Li et al. |
| 8,167,935 | B2 | 5/2012 | Mcguckin, Jr. et al. |
| 8,246,678 | B2 | 8/2012 | Salahieh et al. |
| 8,252,037 | B2 | 8/2012 | Styrc et al. |
| 8,303,647 | B2 | 11/2012 | Case |
| 8,545,525 | B2 | 10/2013 | Surti et al. |
| 8,585,757 | B2 | 11/2013 | Agathos |
| 8,637,144 | B2 | 1/2014 | Ford |
| 8,722,178 | B2 | 5/2014 | Ashmead et al. |

(56) References Cited

U.S. PATENT DOCUMENTS

| | | | |
|---|---|---|---|
| 8,728,103 | B2 | 5/2014 | Surti et al. |
| 8,801,774 | B2 | 8/2014 | Silverman |
| 8,808,848 | B2 | 8/2014 | Bacino |
| 8,845,709 | B2 | 9/2014 | Styrc et al. |
| 8,852,272 | B2 | 10/2014 | Gross et al. |
| 8,870,948 | B1 | 10/2014 | Erzberger et al. |
| 8,936,634 | B2 | 1/2015 | Irwin et al. |
| 9,039,757 | B2 | 5/2015 | Mclean et al. |
| 9,101,696 | B2 | 8/2015 | Leontein et al. |
| 9,107,771 | B2 | 8/2015 | Wubbeling et al. |
| 9,125,740 | B2 | 9/2015 | Morriss et al. |
| 9,198,787 | B2 | 12/2015 | Kratzberg et al. |
| 9,241,695 | B2 | 1/2016 | Peavey et al. |
| 9,295,552 | B2 | 3/2016 | Mclean et al. |
| 9,345,601 | B2 | 5/2016 | Jantzen et al. |
| 9,375,308 | B2 | 6/2016 | Norris |
| 9,399,085 | B2 | 7/2016 | Cleek et al. |
| 9,554,786 | B2 | 1/2017 | Carley et al. |
| 9,554,900 | B2 | 1/2017 | Bruchman et al. |
| 9,681,948 | B2 | 6/2017 | Levi et al. |
| 9,737,422 | B2 | 8/2017 | Armstrong et al. |
| 9,743,932 | B2 | 8/2017 | Amplatz et al. |
| 9,839,540 | B2 | 12/2017 | Armstrong et al. |
| 9,931,204 | B2 | 4/2018 | Rothstein et al. |
| 9,968,443 | B2 | 5/2018 | Bruchman et al. |
| 10,335,298 | B2 | 7/2019 | Armstrong et al. |
| D926,322 | S | 7/2021 | Bennett et al. |
| 11,055,112 | B2 | 7/2021 | Miller et al. |
| 11,278,399 | B2 | 3/2022 | Liu |
| 2001/0053929 | A1 | 12/2001 | Vonesh et al. |
| 2002/0045936 | A1 | 4/2002 | Moe |
| 2002/0055773 | A1 | 5/2002 | Campbell et al. |
| 2002/0076542 | A1 | 6/2002 | Kramer et al. |
| 2002/0082687 | A1 | 6/2002 | Moe |
| 2002/0133226 | A1 | 9/2002 | Marquez et al. |
| 2002/0151953 | A1 | 10/2002 | Chobotov et al. |
| 2002/0151956 | A1 | 10/2002 | Chobotov et al. |
| 2002/0183840 | A1 | 12/2002 | Lapeyre et al. |
| 2002/0198588 | A1 | 12/2002 | Armstrong et al. |
| 2003/0055494 | A1 | 3/2003 | Bezuidenhout et al. |
| 2003/0055496 | A1 | 3/2003 | Cai et al. |
| 2003/0060871 | A1 | 3/2003 | Hill et al. |
| 2003/0074052 | A1 | 4/2003 | Besselink |
| 2003/0097175 | A1 | 5/2003 | O'Connor et al. |
| 2003/0125805 | A1 | 7/2003 | Johnson et al. |
| 2003/0180488 | A1 | 9/2003 | Lim et al. |
| 2003/0209835 | A1 | 11/2003 | Chun et al. |
| 2003/0229394 | A1 | 12/2003 | Ogle et al. |
| 2004/0024448 | A1 | 2/2004 | Chang et al. |
| 2004/0024451 | A1 | 2/2004 | Johnson et al. |
| 2004/0026245 | A1 | 2/2004 | Agarwal et al. |
| 2004/0044400 | A1 | 3/2004 | Cheng et al. |
| 2004/0044401 | A1 | 3/2004 | Bales et al. |
| 2004/0133266 | A1 | 7/2004 | Clerc et al. |
| 2004/0176839 | A1 | 9/2004 | Huynh et al. |
| 2004/0224442 | A1 | 11/2004 | Grigg |
| 2004/0243222 | A1 | 12/2004 | Osborne et al. |
| 2004/0260277 | A1 | 12/2004 | Maguire |
| 2004/0260389 | A1 | 12/2004 | Case et al. |
| 2004/0260393 | A1 | 12/2004 | Rahdert et al. |
| 2005/0027348 | A1 | 2/2005 | Case et al. |
| 2005/0080476 | A1 | 4/2005 | Gunderson et al. |
| 2005/0119722 | A1 | 6/2005 | Styrc et al. |
| 2005/0137680 | A1 | 6/2005 | Ortiz et al. |
| 2005/0137682 | A1 | 6/2005 | Justino |
| 2005/0203614 | A1 | 9/2005 | Forster et al. |
| 2005/0261765 | A1 | 11/2005 | Liddicoat |
| 2005/0283224 | A1 | 12/2005 | King |
| 2006/0008497 | A1 | 1/2006 | Gabbay |
| 2006/0009835 | A1 | 1/2006 | Osborne et al. |
| 2006/0015171 | A1 | 1/2006 | Armstrong |
| 2006/0036311 | A1 | 2/2006 | Nakayama et al. |
| 2006/0041091 | A1 | 2/2006 | Chang et al. |
| 2006/0106337 | A1 | 5/2006 | Blankenship |
| 2006/0122693 | A1 | 6/2006 | Biadillah et al. |
| 2006/0135985 | A1 | 6/2006 | Cox et al. |
| 2006/0154365 | A1 | 7/2006 | Ratcliffe et al. |
| 2006/0161241 | A1 | 7/2006 | Barbut et al. |
| 2006/0190070 | A1 | 8/2006 | Dieck et al. |
| 2006/0229718 | A1 | 10/2006 | Marquez |
| 2006/0259136 | A1 | 11/2006 | Nguyen et al. |
| 2006/0265053 | A1 | 11/2006 | Hunt |
| 2006/0271091 | A1 | 11/2006 | Campbell et al. |
| 2006/0276813 | A1 | 12/2006 | Greenberg |
| 2006/0276883 | A1 | 12/2006 | Greenberg et al. |
| 2006/0276888 | A1 | 12/2006 | Lee et al. |
| 2006/0282162 | A1 | 12/2006 | Nguyen et al. |
| 2006/0287719 | A1 | 12/2006 | Rowe et al. |
| 2006/0290027 | A1 | 12/2006 | O'Connor et al. |
| 2007/0010876 | A1 | 1/2007 | Salahieh et al. |
| 2007/0012624 | A1 | 1/2007 | Bacino et al. |
| 2007/0021826 | A1 | 1/2007 | Case et al. |
| 2007/0060999 | A1 | 3/2007 | Randall et al. |
| 2007/0100435 | A1 | 5/2007 | Case et al. |
| 2007/0118210 | A1 | 5/2007 | Pinchuk |
| 2007/0129786 | A1 | 6/2007 | Beach et al. |
| 2007/0207186 | A1 | 9/2007 | Scanlon et al. |
| 2007/0207816 | A1 | 9/2007 | Spain |
| 2007/0208417 | A1 | 9/2007 | Agnew |
| 2007/0208421 | A1 | 9/2007 | Quigley |
| 2007/0213800 | A1 | 9/2007 | Fierens et al. |
| 2007/0244552 | A1 | 10/2007 | Salahieh et al. |
| 2007/0250146 | A1 | 10/2007 | Cully et al. |
| 2007/0250153 | A1 | 10/2007 | Cully et al. |
| 2007/0254012 | A1 | 11/2007 | Ludwig et al. |
| 2008/0009940 | A1 | 1/2008 | Cribier |
| 2008/0026190 | A1 | 1/2008 | King et al. |
| 2008/0039934 | A1 | 2/2008 | Styrc |
| 2008/0051876 | A1 | 2/2008 | Ta et al. |
| 2008/0065198 | A1 | 3/2008 | Quintessenza |
| 2008/0071369 | A1 | 3/2008 | Tuval et al. |
| 2008/0082154 | A1 | 4/2008 | Tseng et al. |
| 2008/0097401 | A1 | 4/2008 | Trapp et al. |
| 2008/0097579 | A1 | 4/2008 | Shanley et al. |
| 2008/0097582 | A1 | 4/2008 | Shanley et al. |
| 2008/0119943 | A1 | 5/2008 | Armstrong et al. |
| 2008/0133004 | A1 | 6/2008 | White |
| 2008/0140178 | A1 | 6/2008 | Rasmussen et al. |
| 2008/0195199 | A1 | 8/2008 | Kheradvar et al. |
| 2008/0208327 | A1 | 8/2008 | Rowe |
| 2008/0220041 | A1 | 9/2008 | Brito et al. |
| 2008/0228263 | A1 | 9/2008 | Ryan |
| 2008/0319531 | A1 | 12/2008 | Doran et al. |
| 2009/0005854 | A1 | 1/2009 | Huang et al. |
| 2009/0030499 | A1 | 1/2009 | Bebb et al. |
| 2009/0036976 | A1 | 2/2009 | Beach et al. |
| 2009/0043373 | A1 | 2/2009 | Arnault et al. |
| 2009/0099640 | A1 | 4/2009 | Weng |
| 2009/0104247 | A1 | 4/2009 | Pacetti |
| 2009/0117334 | A1 | 5/2009 | Sogard et al. |
| 2009/0138079 | A1 | 5/2009 | Tuval et al. |
| 2009/0157175 | A1 | 6/2009 | Benichou |
| 2009/0182413 | A1 | 7/2009 | Burkart et al. |
| 2009/0240320 | A1 | 9/2009 | Tuval et al. |
| 2009/0264997 | A1 | 10/2009 | Salahieh et al. |
| 2009/0276039 | A1 | 11/2009 | Meretei |
| 2009/0281609 | A1 | 11/2009 | Benichou et al. |
| 2009/0287305 | A1 | 11/2009 | Amalaha |
| 2009/0292350 | A1 | 11/2009 | Eberhardt et al. |
| 2009/0306762 | A1 | 12/2009 | McCullagh et al. |
| 2009/0306766 | A1 | 12/2009 | McDermott et al. |
| 2010/0016940 | A1 | 1/2010 | Shokoohi et al. |
| 2010/0023114 | A1 | 1/2010 | Chambers et al. |
| 2010/0036021 | A1 | 2/2010 | Lee et al. |
| 2010/0036484 | A1 | 2/2010 | Hariton et al. |
| 2010/0049294 | A1 | 2/2010 | Zukowski et al. |
| 2010/0082089 | A1 | 4/2010 | Quadri et al. |
| 2010/0082094 | A1 | 4/2010 | Quadri et al. |
| 2010/0094394 | A1 | 4/2010 | Beach et al. |
| 2010/0094405 | A1 | 4/2010 | Cottone |
| 2010/0106240 | A1 | 4/2010 | Duggal et al. |
| 2010/0114307 | A1 | 5/2010 | Agnew et al. |
| 2010/0131056 | A1 | 5/2010 | Lapeyre |
| 2010/0137998 | A1 | 6/2010 | Sobrino-Serrano et al. |

(56) References Cited

U.S. PATENT DOCUMENTS

2010/0159171 A1 6/2010 Clough
2010/0168839 A1* 7/2010 Braido .................. A61F 2/2418 623/2.18
2010/0185274 A1 7/2010 Moaddeb et al.
2010/0185277 A1 7/2010 Braido et al.
2010/0191320 A1 7/2010 Straubinger et al.
2010/0204785 A1 8/2010 Alkhatib
2010/0217382 A1 8/2010 Chau et al.
2010/0248324 A1 9/2010 Xu et al.
2010/0249923 A1 9/2010 Alkhatib et al.
2010/0256738 A1 10/2010 Berglund
2010/0262231 A1 10/2010 Tuval et al.
2010/0286760 A1 11/2010 Beach et al.
2010/0298931 A1 11/2010 Quadri et al.
2011/0009953 A1 1/2011 Luk et al.
2011/0040366 A1 2/2011 Goetz et al.
2011/0054515 A1 3/2011 Bridgeman et al.
2011/0064781 A1 3/2011 Cleek et al.
2011/0087318 A1 4/2011 Daugherty et al.
2011/0160836 A1 6/2011 Behan
2011/0172784 A1 7/2011 Richter et al.
2011/0208283 A1 8/2011 Rust
2011/0218619 A1 9/2011 Benichou et al.
2011/0257739 A1 10/2011 Corbett
2011/0282439 A1 11/2011 Thill et al.
2011/0282440 A1* 11/2011 Cao ....................... A61F 2/2418 623/2.18
2011/0295363 A1 12/2011 Girard et al.
2012/0035722 A1 2/2012 Tuval
2012/0078357 A1 3/2012 Conklin
2012/0089223 A1* 4/2012 Nguyen ................ A61F 2/2418 623/2.14
2012/0101567 A1 4/2012 Jansen
2012/0116496 A1 5/2012 Chuter et al.
2012/0116498 A1 5/2012 Chuter et al.
2012/0123529 A1 5/2012 Levi et al.
2012/0123530 A1 5/2012 Carpentier et al.
2012/0130468 A1 5/2012 Khosravi et al.
2012/0130471 A1 5/2012 Shoemaker et al.
2012/0215303 A1 8/2012 Quadri et al.
2012/0253453 A1 10/2012 Bruchman et al.
2012/0277734 A1 11/2012 Goetz et al.
2012/0290082 A1 11/2012 Quint et al.
2013/0018456 A1 1/2013 Li et al.
2013/0018458 A1 1/2013 Yohanan et al.
2013/0079700 A1 3/2013 Ballard et al.
2013/0110229 A1 5/2013 Bokeriya et al.
2013/0116655 A1 5/2013 Bacino et al.
2013/0131780 A1 5/2013 Armstrong et al.
2013/0150956 A1 6/2013 Yohanan et al.
2013/0158647 A1 6/2013 Norris et al.
2013/0183515 A1 7/2013 White
2013/0184807 A1 7/2013 Kovach et al.
2013/0197624 A1 8/2013 Armstrong et al.
2013/0204360 A1 8/2013 Gainor
2013/0253466 A1 9/2013 Campbell et al.
2013/0297003 A1 11/2013 Pinchuk
2013/0338755 A1 12/2013 Goetz et al.
2014/0005771 A1 1/2014 Braido et al.
2014/0031924 A1 1/2014 Bruchman et al.
2014/0031927 A1 1/2014 Bruchman et al.
2014/0094898 A1 4/2014 Borck
2014/0106951 A1 4/2014 Brandon
2014/0135897 A1 5/2014 Cully et al.
2014/0163671 A1 6/2014 Bruchman et al.
2014/0163673 A1 6/2014 Bruchman et al.
2014/0172066 A1 6/2014 Goepfrich et al.
2014/0172069 A1 6/2014 Roeder et al.
2014/0172077 A1 6/2014 Bruchman et al.
2014/0172078 A1 6/2014 Bruchman et al.
2014/0172079 A1 6/2014 Bruchman et al.
2014/0172082 A1 6/2014 Bruchman et al.
2014/0172083 A1* 6/2014 Bruchman ............ A61F 2/2412 156/185
2014/0180400 A1 6/2014 Bruchman et al.
2014/0180402 A1 6/2014 Bruchman et al.
2014/0194968 A1 7/2014 Zukowski
2014/0277413 A1 9/2014 Richter et al.
2014/0277418 A1 9/2014 Miller
2014/0296969 A1 10/2014 Tegels et al.
2014/0324164 A1 10/2014 Gross et al.
2014/0330368 A1 11/2014 Gloss et al.
2014/0343670 A1 11/2014 Bakis et al.
2015/0005870 A1 1/2015 Kovach et al.
2015/0018944 A1 1/2015 O'Connell et al.
2015/0088250 A1 3/2015 Zeng et al.
2015/0142100 A1 5/2015 Morriss et al.
2015/0157456 A1 6/2015 Armstrong
2015/0157770 A1 6/2015 Cully et al.
2015/0224231 A1 8/2015 Bruchman et al.
2015/0245910 A1 9/2015 Righini et al.
2015/0313871 A1 11/2015 Li et al.
2015/0366664 A1 12/2015 Guttenberg et al.
2016/0001469 A1 1/2016 Bacchereti et al.
2016/0015422 A1 1/2016 De et al.
2016/0074161 A1* 3/2016 Bennett ................. A61F 2/2418 29/890.126
2016/0106537 A1 4/2016 Christianson et al.
2016/0113699 A1 4/2016 Sverdlik et al.
2016/0175095 A1 6/2016 Dienno et al.
2016/0206424 A1 7/2016 Al-Jilaihawi et al.
2016/0213465 A1 7/2016 Girard et al.
2016/0235525 A1 8/2016 Rothstein et al.
2016/0250051 A1 9/2016 Lim et al.
2016/0310268 A1 10/2016 Oba et al.
2017/0000603 A1 1/2017 Conklin et al.
2017/0027727 A1 2/2017 Wuebbeling et al.
2017/0056169 A1 3/2017 Johnson et al.
2017/0095330 A1 4/2017 Malewicz et al.
2017/0100236 A1 4/2017 Robertson et al.
2017/0105854 A1 4/2017 Treacy et al.
2017/0106176 A1 4/2017 Taft et al.
2017/0128199 A1 5/2017 Gurovich et al.
2017/0143488 A1 5/2017 Lashinski
2017/0156859 A1 6/2017 Chang et al.
2017/0165066 A1 6/2017 Rothstein
2017/0252153 A1 9/2017 Chau et al.
2017/0348101 A1 12/2017 Vaughn et al.
2018/0021129 A1 1/2018 Peterson et al.
2018/0177583 A1 6/2018 Cully et al.
2018/0271653 A1 9/2018 Vidlund et al.
2019/0076245 A1 3/2019 Arcaro et al.
2019/0091014 A1 3/2019 Arcaro et al.
2019/0091015 A1 3/2019 Dienno et al.
2019/0110893 A1 4/2019 Haarer et al.
2019/0125517 A1 5/2019 Cully et al.
2019/0125528 A1 5/2019 Busalacchi et al.
2019/0125530 A1 5/2019 Arcaro et al.
2019/0125531 A1 5/2019 Bennett et al.
2019/0125534 A1 5/2019 Arcaro et al.
2019/0209739 A1 7/2019 Goepfrich et al.
2019/0216592 A1 7/2019 Cully et al.
2019/0328525 A1 10/2019 Noe et al.
2020/0022828 A1 1/2020 Armstrong et al.
2020/0179663 A1 6/2020 McDaniel et al.
2020/0276014 A1 9/2020 Burkart et al.
2022/0183831 A1 6/2022 Burkart et al.
2022/0273426 A1 9/2022 Hagaman et al.

FOREIGN PATENT DOCUMENTS

CN 101091675 A 12/2007
CN 101374477 A 2/2009
CN 101420913 A 4/2009
CN 101849863 A 10/2010
CN 101902989 A 12/2010
CN 101926699 A 12/2010
CN 201744060 U 2/2011
CN 102015009 A 4/2011
CN 102119013 A 7/2011
CN 102573703 A 7/2012
CN 102652694 A 9/2012
CN 102764169 A 11/2012
CN 102883684 A 1/2013

(56) References Cited

FOREIGN PATENT DOCUMENTS

| | | | |
|---|---|---|---|
| CN | 103079498 | A | 5/2013 |
| CN | 103732183 | A | 4/2014 |
| CN | 103781439 | A | 5/2014 |
| CN | 105007955 | A | 10/2015 |
| CN | 105662651 | A | 6/2016 |
| CN | 105792780 | A | 7/2016 |
| CN | 106794065 | A | 5/2017 |
| CN | 107690323 | A | 2/2018 |
| CN | 108578016 | A | 9/2018 |
| DE | 212013000104 | U1 | 11/2014 |
| EP | 0293090 | A2 | 11/1988 |
| EP | 0313263 | A2 | 4/1989 |
| EP | 0582870 | A2 | 2/1994 |
| EP | 0775472 | A2 | 5/1997 |
| EP | 0815806 | A2 | 1/1998 |
| EP | 0893108 | A2 | 1/1999 |
| EP | 1057460 | A1 | 12/2000 |
| EP | 1666003 | A1 | 6/2006 |
| EP | 2193762 | A1 | 6/2010 |
| EP | 2400923 | A1 | 1/2012 |
| FR | 2591100 | A1 | 6/1987 |
| GB | 2513194 | A | 10/2014 |
| JP | 44032400 | B | 12/1969 |
| JP | H09241412 | A | 9/1997 |
| JP | H11290448 | A | 10/1999 |
| JP | H11512635 | A | 11/1999 |
| JP | 2001508641 | A | 7/2001 |
| JP | 2005505320 | A | 2/2005 |
| JP | 2007526098 | A | 9/2007 |
| JP | 2012152563 | A | 8/2012 |
| WO | WO-1994013224 | A1 | 6/1994 |
| WO | WO-1995005555 | A1 | 2/1995 |
| WO | WO-1995009586 | A1 | 4/1995 |
| WO | WO-1996002212 | A1 | 2/1996 |
| WO | WO-1996007370 | A1 | 3/1996 |
| WO | WO-1996040348 | A1 | 12/1996 |
| WO | WO-1997010871 | A1 | 3/1997 |
| WO | WO-1999026558 | A1 | 6/1999 |
| WO | WO-2000018333 | A1 | 4/2000 |
| WO | WO-2000041649 | A1 | 7/2000 |
| WO | WO-2000047271 | A1 | 8/2000 |
| WO | WO-2000062716 | A1 | 10/2000 |
| WO | WO-2001028453 | A2 | 4/2001 |
| WO | WO-2001041679 | A1 | 6/2001 |
| WO | WO-2001064278 | A1 | 9/2001 |
| WO | WO-2001074272 | A2 | 10/2001 |
| WO | WO-2002007795 | A2 | 1/2002 |
| WO | WO-2002024118 | A1 | 3/2002 |
| WO | WO-2002024119 | A1 | 3/2002 |
| WO | WO-2002045933 | A2 | 6/2002 |
| WO | WO-2002047468 | A1 | 6/2002 |
| WO | WO-2002060506 | A1 | 8/2002 |
| WO | WO-2002100301 | A1 | 12/2002 |
| WO | WO-2003003946 | A1 | 1/2003 |
| WO | WO-2003007795 | A2 | 1/2003 |
| WO | WO-2003047468 | A1 | 6/2003 |
| WO | WO-2003090834 | A2 | 11/2003 |
| WO | WO-2004000375 | A1 | 12/2003 |
| WO | WO-2006058322 | A2 | 6/2006 |
| WO | WO-2007016251 | A2 | 2/2007 |
| WO | WO-2008021002 | A1 | 2/2008 |
| WO | WO-2008021006 | A2 | 2/2008 |
| WO | WO-2008028964 | A2 | 3/2008 |
| WO | WO-2008036870 | A2 | 3/2008 |
| WO | WO-2008052421 | A1 | 5/2008 |
| WO | WO-2008091589 | A1 | 7/2008 |
| WO | WO-2008097589 | A1 | 8/2008 |
| WO | WO-2008097592 | A2 | 8/2008 |
| WO | WO-2008150529 | A1 | 12/2008 |
| WO | WO-2009029199 | A1 | 3/2009 |
| WO | WO-2009045332 | A2 | 4/2009 |
| WO | WO-2009100210 | A1 | 8/2009 |
| WO | WO-2009108355 | A1 | 9/2009 |
| WO | WO-2010006783 | A1 | 1/2010 |
| WO | WO-2010008570 | A1 | 1/2010 |
| WO | WO-2010030766 | A1 | 3/2010 |
| WO | WO-2010057262 | A1 | 5/2010 |
| WO | WO-2010086460 | A1 | 8/2010 |
| WO | WO-2010132707 | A1 | 11/2010 |
| WO | WO-2010150208 | A2 | 12/2010 |
| WO | WO-2011098565 | A1 | 8/2011 |
| WO | WO-2011109450 | A2 | 9/2011 |
| WO | WO-2012004460 | A2 | 1/2012 |
| WO | WO-2012011261 | A1 | 1/2012 |
| WO | WO-2012040643 | A2 | 3/2012 |
| WO | WO-2012065080 | A2 | 5/2012 |
| WO | WO-2012082952 | A2 | 6/2012 |
| WO | WO-2012099979 | A1 | 7/2012 |
| WO | WO-2012110767 | A2 | 8/2012 |
| WO | WO-2012116368 | A2 | 8/2012 |
| WO | WO-2012158944 | A1 | 11/2012 |
| WO | WO-2012167131 | A1 | 12/2012 |
| WO | WO-2013074990 | A1 | 5/2013 |
| WO | WO-2013096854 | A2 | 6/2013 |
| WO | WO-2013109337 | A1 | 7/2013 |
| WO | WO-2014099722 | A1 | 6/2014 |
| WO | WO-2014144937 | A2 | 9/2014 |
| WO | WO-2014149319 | A1 | 9/2014 |
| WO | WO-2015045002 | A1 | 4/2015 |
| WO | WO-2015171743 | A2 | 11/2015 |
| WO | WO-2015173794 | A1 | 11/2015 |
| WO | WO-2016028591 | A1 | 2/2016 |
| WO | WO-2016100913 | A1 | 6/2016 |
| WO | WO-2016186909 | A1 | 11/2016 |
| WO | WO-2017038145 | A1 | 3/2017 |
| WO | WO-2017096157 | A1 | 6/2017 |
| WO | WO-2017136596 | A1 | 8/2017 |
| WO | WO-2019074869 | A1 | 4/2019 |
| WO | WO-2019246268 | A1 | 12/2019 |

OTHER PUBLICATIONS

Cohn L.H., “Cardiac Surgery in the Adult,” Third Edition, Chapter 2, 2008, 31 Pages.

Forward citations for E12 obtained from: https://scholar.google.com/scholar?cites=5981833429320176658&assdt=2005&sciodt=0,5&hl= en. no date provided /RSP/ Mar. 20, 2026.

Nakayama Y., “Microporous Stent Achieves Brain Aneurysm Occlusion Without Disturbing Branching Flow,” NeuroNews, Nov. 2012, No. 8, pp. 1-2.

Nishi S., et al., “Development of Microporous Self-expanding Stent Grafts for Treating Cerebral Aneurysms: Designing Micropores to Control Intimal Hyperplasia,” Journal of Artificial Organs, 2011, vol. 14, pp. 348-356.

“S-Shaped,” Google Image Search Results, Accessed on Nov. 1, 2013, 1 Page.

Thubrikar M., “The Aortic Valve,” Chapter 1: Geometry of the Aortic Valve, Informa Healthcare, CRC Press, Inc, 2011, 40 Pages.

* cited by examiner

PROSTHETIC VALVES WITH MECHANICALLY COUPLED LEAFLETS

PRIORITY INFORMATION

This application is a continuation of U.S. patent application Ser. No. 17/377,091, filed Jul. 15, 2021, which is a continuation of U.S. application Ser. No. 16/129,682, filed Sep. 12, 2018, now U.S. Pat. No. 11,109,963, which claims the benefit of Provisional Application No. 62/572,274, filed Oct. 13, 2017. The present application also claims the benefit of Provisional Application No. 62/579,753, filed Oct. 31, 2017. The present application also claims the benefit of Provisional Application No. 62/564,031, filed Sep. 27, 2017. The prior applications are incorporated by reference herein in their entireties.

FIELD

The present disclosure relates generally to prosthetic valves and more specifically flexible leaflet-type prosthetic valve devices.

BACKGROUND

Prosthetic valves with flexible leaflets typically require some means for securing the leaflets to a support structure, such as a leaflet frame. Prosthetic valve leaflets are thus generally coupled to a support structure to form the prosthetic valve. In operation, the leaflets open when the inflow fluid pressure exceeds the outflow fluid pressure and close when the outflow fluid pressure exceeds the inflow fluid pressure. The free edges of the leaflets coapt under the influence of outflow fluid pressure closing the valve so as to restrict outflow blood from flowing retrograde through the prosthetic valve. A commissure is an area where adjacently situated leaflets come together at the support structure. Commissure posts are generally those structures of a leaflet frame in the area of a commissure to which adjacently situated leaflets attach.

Some conventional means for attaching leaflets to leaflet frames include sewing or adhesive/thermal bonding of the leaflet to the leaflet frame. Both techniques have disadvantages that affect the life and performance of a prosthetic valve. In particular, the integrity of adhesive bonds tends to be negatively impacted in an aqueous environment, particularly on the time scale of a prosthetic valve. The suturing process tends to be labor-intensive, and the quality of the result may depend on the skill-level of the assembler. Moreover, the tension applied to the suture may not be well-controlled, which can affect the local geometries of the leaflet. All of these factors may adversely impact the functionality and structural integrity of the leaflets over the long term. Other means include disposing the leaflet over a plurality of projections of the leaflet frame as disclosed, for example, in U.S. Pat. No. 9,855,141 to Dienno.

However, leaflet failure due to tearing and/or detaching from the leaflet frame in the area of the commissure continues to be an undesirable risk to patients. One factor contributing to tearing and/or detachment of the leaflet is that a peak stress in the leaflet is generally observed in the area of the commissure when the prosthetic valve is closed and under fluid backpressure.

A number of attempts have been made to mitigate this stress, including increasing the ultimate tensile strength of the leaflet material to increase tear resistance (e.g., by increasing a thickness of the leaflet material), increasing the height of the commissure posts in an effort to help distribute the load on the leaflet in an area of the commissure posts over a greater length and/or area, and changing a geometry of those portions of the commissure post that interface with the leaflet. However, increasing leaflet thickness can reduce overall prosthetic valve performance due, at least in part, to an increase in bending stiffness of the leaflet. And, increasing leaflet thickness and/or a height of the commissure post increases prosthetic valve profile, which is undesirable in transcatheter applications. Moreover, a prosthetic valve with an increased commissure post height (and thus overall prosthetic valve height) has a potential to have undesirable interaction with native anatomy, such as ventricular wall interaction or left ventricular outflow tract obstruction in the mitral position and coronary obstruction in the aortic position.

New ways of securing leaflets to support structures are needed to further minimize the potential for leaflet failure while minimizing the profile of the prosthetic valve.

SUMMARY

Various embodiments are directed toward prosthetic valves having a leaflet frame and one or more leaflets, where the leaflet(s) are coupled to the leaflet frame via one or more leaflet frame projections. Some examples are directed to apparatuses, systems, and methods for valve replacement, such as cardiac valve replacement, although a variety of applications are contemplated According to one example, ("Example 1"), prosthetic valve includes a plurality of leaflets including a first leaflet and a second leaflet, each leaflet having a leaflet attachment region; and a frame including a commissure post that includes: a first tine including a first interior edge and a first exterior edge opposite the first interior edge, the first exterior edge including a first projection extending from the first exterior edge of the first tine; and a second tine including a second interior edge and a second exterior edge opposite the second interior edge, the second exterior edge including a second projection extending from the second exterior edge of the second tine, a spine positioned between the first and second tines such that the interior edges of the first and second tines face the spine; and a plurality of slots including a first slot and a second slot, the first slot being defined at least between the first tine and the spine, and the second slot being defined at least between the second tine and the spine, wherein the leaflet attachment region of the first leaflet extends through the first slot and wraps around the first tine and engages the first projection, and wherein a first portion of the leaflet attachment region of the second leaflet extends through the second slot and wraps around a portion of the second tine and engages the second projection.

According to another example, ("Example 2") further to Example 1, the spine is positioned between at least a portion of the first and second leaflets.

According to another example, ("Example 3") further to any of Examples 1 to 2, wherein the first and second leaflets each comprise a leaflet free edge and wherein a gap is defined between the leaflet free edges of the first and second leaflets adjacent the commissure post.

According to another example, ("Example 4") further to any of Examples 1 to 3, the first projection extends through the leaflet attachment region of the first leaflet, and wherein the second projection extends through the leaflet attachment region of the second leaflet.

According to another example, ("Example 5") further to any of Examples 1 to 4, an end of the first slot is an open end and wherein end of the first tine is a free end.

According to another example, ("Example 6") further to any of Examples 1 to 5, the first tine has a first end and a second end and wherein the first and second ends are each integral to the frame.

According to another example, ("Example 7") further to any of Examples 1 to 6, the first tine extends from the commissure post at a position proximate a free end of the commissure post.

According to another example, ("Example 8") further to any of Examples 1 to 7, the frame further includes a third projection, and wherein a second portion of the leaflet attachment region of the first leaflet engages the third projection without being wrapped around the frame.

According to another example, ("Example 9") further to any of Examples 1 to 8, the valve further includes a leaflet retention member coupled to the leaflet frame such that the leaflet attachment region of the leaflet is situated between the leaflet frame and the leaflet retention member.

According to another example, ("Example 10") further to Example 9, the leaflet retention member engages the first and second frame to secure the leaflet retention member to the leaflet frame, wherein the leaflet retention member includes a first portion that extends along a leaflet frame inner surface of the first frame projection, and wherein the leaflet retention member includes a second portion that extends along a leaflet frame outer surface of the second frame projection.

According to another example, ("Example 11") further to any of Examples 9 to 10, wherein the leaflet retention member is a fiber.

According to another example, ("Example 12") further to any of Examples 1 to 11, the valve further includes a jacket molded over the leaflet retention member.

According to another example, ("Example 13") further to Example 12, the jacket is formed of a TFE-PMVE copolymer.

According to another example, ("Example 14") further to any of Examples 12 to 13, wherein the jacket is formed of a flexible polymer.

According to another example, ("Example 15") further to Example 14, wherein the flexible polymer is silicone.

According to another example, ("Example 16") further to any of Examples 1 to 15, the first and second leaflets each define two termini at an intersection of a leaflet free edge and a leaflet attachment region of the respective leaflet, the leaflet attachment region of each leaflet being coupled to the frame such that the leaflet attachment region adjacent the terminus of the first and second leaflets when positioned adjacent to one another diverge relative to each other from a location away from the terminus to the terminus.

According to another example, ("Example 17") a prosthetic valve includes a plurality of leaflets including a first leaflet and a second leaflet, each leaflet having a leaflet attachment region; and a frame including: a spine; a plurality of tines situated adjacent the spine such that a first slot is defined between the spine and a first tine of the plurality of tines, and such that a second slot is defined between the spine a second tine of the plurality of tines; and a plurality of projections extending from the first and second tines, the plurality of projections includes a first projection extending from the first tine and a second projection extending from the second tine, wherein the leaflet attachment region of the first leaflet extends through the first slot and wraps around the first tine and engages the first projection extending from the first tine, and wherein the leaflet attachment region of the second leaflet extends through the second slot and wraps around the second tine and engages the second projection extending from the second tine.

According to another example, ("Example 18") further to Example 17, the spine is positioned between at least a portion of the first and second leaflets such that a gap is formed between the leaflet free edges of the first and second leaflets adjacent the spine.

According to another example, ("Example 19") further to any of Examples 17 to 18, the first projection extends through the leaflet attachment region of the first leaflet, and wherein the second projection extends through the leaflet attachment region of the second leaflet.

According to another example, ("Example 20") further to any of Examples 17 to 19, an end of the first slot is an open end, and an end of the first tine is a free end.

According to another example, ("Example 21") further to any of Examples 17 to 20, the frame further includes a third projection, and wherein a second portion of the leaflet attachment region of the first leaflet engages the third projection without being wrapped around the frame.

According to another example, ("Example 22") further to any of Examples 17 to 21, the valve further includes a leaflet retention member coupled to the leaflet frame such that the leaflet attachment region of the leaflet is situated between the leaflet frame and the leaflet retention member.

According to another example, ("Example 23") further to Example 22, the leaflet retention member engages the first and second frame to secure the leaflet retention member to the leaflet frame, wherein the leaflet retention member includes a first portion that extends along a leaflet frame inner surface of the first frame projection, and wherein the leaflet retention member includes a second portion that extends along a leaflet frame outer surface of the second frame projection.

According to another example, ("Example 24") further to any of Examples 22 to 23, wherein the leaflet retention member is a fiber.

According to another example, ("Example 25") further to any of Examples 17 to 24, the valve further includes a jacket molded over the leaflet retention member.

According to another example, ("Example 26") further to Example 25, the jacket is formed of a TFE-PMVE copolymer.

According to another example, ("Example 27") further to any of Examples 25 to 26, wherein the jacket is formed of a flexible polymer.

According to another example, ("Example 28") further to Example 28, the flexible polymer is silicone.

According to another example, ("Example 29") further to any of Examples 22 to 28, wherein the leaflet retention member has a body including a plurality of adjacently situated struts that extend from a first side of the body, wherein a region is defined between adjacently situated struts, and wherein the first frame projection extends through the region defined between the adjacently situated struts such that the adjacently situated struts engage the frame projection.

According to another example, ("Example 30") further to Example 29, the body of the leaflet retention member further includes a first end, a second end opposite the first end, a first side extending between the first and second ends, a second side extending between the first and second ends, wherein the adjacently situated struts extend between the first and second sides and are situated between the first and second ends, the leaflet retention member including a first cell and a second cell, the first cell being defined between the first side and the strut, and the second cell being defined adjacent the first cell between the second side and the strut, wherein the first frame projection extends through the first cell and wherein the second frame projection extends through the second cell.

According to another example, ("Example 31") further to any of Examples 17 to 30, the first and second leaflets each define two termini at an intersection of a leaflet free edge and a leaflet attachment region of the respective leaflet, the leaflet attachment regions of each of the first and second leaflets being coupled to the frame such that the leaflet attachment regions of the first and second leaflets adjacent the termini diverge relative to each other from a location away from the terminus to the terminus.

According to another example, ("Example 32") further to any of Examples 17 to 30, wherein the frame includes a plurality of support attachment regions each defining two leaflet support attachment regions having distal ends, the respective two support attachment regions diverge relative to each other from a location away from the respective distal ends towards the respective distal ends defining a respective diverging region, and wherein the first and second leaflets each define a leaflet free edge and a leaflet attachment region intersecting at two termini of the respective leaflet, wherein the leaflet attachment regions of each of the first and second leaflets adjacent to a respective terminus are coupled to one of the respective support attachment regions along the respective diverging region, wherein the respective leaflet attachment region adjacent the respective terminus of the first and second leaflets diverge relative to each other from a location away from the respective terminus to the respective terminus.

According to another example, ("Example 33") further to any of Examples 17 to 30, the frame includes a support structure defining a plurality of commissure regions each defining two support attachment portions that diverge relative to each other from a location away from a commissure post tip in an outflow direction towards the commissure post tip; and wherein each of the first and second leaflets defines two leaflet commissure attachment portions adjacent to a leaflet free edge, wherein a respective leaflet commissure attachment portion of each of the first and second leaflets is coupled to one of the two support attachment portions such that the respective leaflet free edges of the first and second leaflets at the leaflet commissure attachment portion diverge relative to each other.

According to another example, ("Example 34") further to any of Examples 17 to 30, each of the first and second leaflets attaches to a support structure of the frame along a diverging region of the support structure such that adjacent leaflet free edges of the first and second leaflets diverge relative to each other at the support structure.

According to another example, ("Example 35") further to any of Examples 17 to 30, each of the first and second leaflets includes a leaflet free edge, wherein the first and second leaflets are attached to a support structure of the frame along a diverging region of the support structure such that the leaflet free edges of the first and second leaflets at the support structure diverge relative to each other, whereby stress within the leaflet along the diverging region is reduced more than 40% relative to a non-diverging attachment when exposed to peak closing pressures of about 135 mmHg for a given support structure length.

According to another example, ("Example 36") a method of manufacturing a heart valve, includes providing a plurality of leaflets including a first leaflet and a second leaflet, each leaflet having a leaflet attachment region, and providing a frame including a commissure post that includes: a first tine including a first interior edge and a first exterior edge opposite the first interior edge, the first exterior edge including a first projection extending from the first exterior edge of the first tine; and a second tine including a second interior edge and a second exterior edge opposite the second interior edge, the second exterior edge including a second projection extending from the second exterior edge of the second tine, a spine positioned between the first and second tines such that the interior edges of the first and second tines face the spine; and a plurality of slots including a first slot and a second slot, the first slot being defined at least between the first tine and the spine, and the second slot being defined at least between the second tine and the spine. The method further includes coupling the leaflet attachment region of the first leaflet to the frame by extending the leaflet attachment region of the first leaflet through the first slot and wrapping the leaflet attachment region of the first leaflet around the first tine such that the leaflet attachment region of the first leaflet engages the first projection; and coupling the leaflet attachment region of the second leaflet to the frame by extending the leaflet attachment region of the second leaflet through the second slot and wrapping the leaflet attachment region of the second leaflet around the second tine such that the leaflet attachment region of the second leaflet engages the second projection.

According to another example, ("Example 37") a method of treating a failing natural heart valve includes surgically implanting into a patient the prosthetic valve of any of Examples 1 to 36.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

Figure 40:
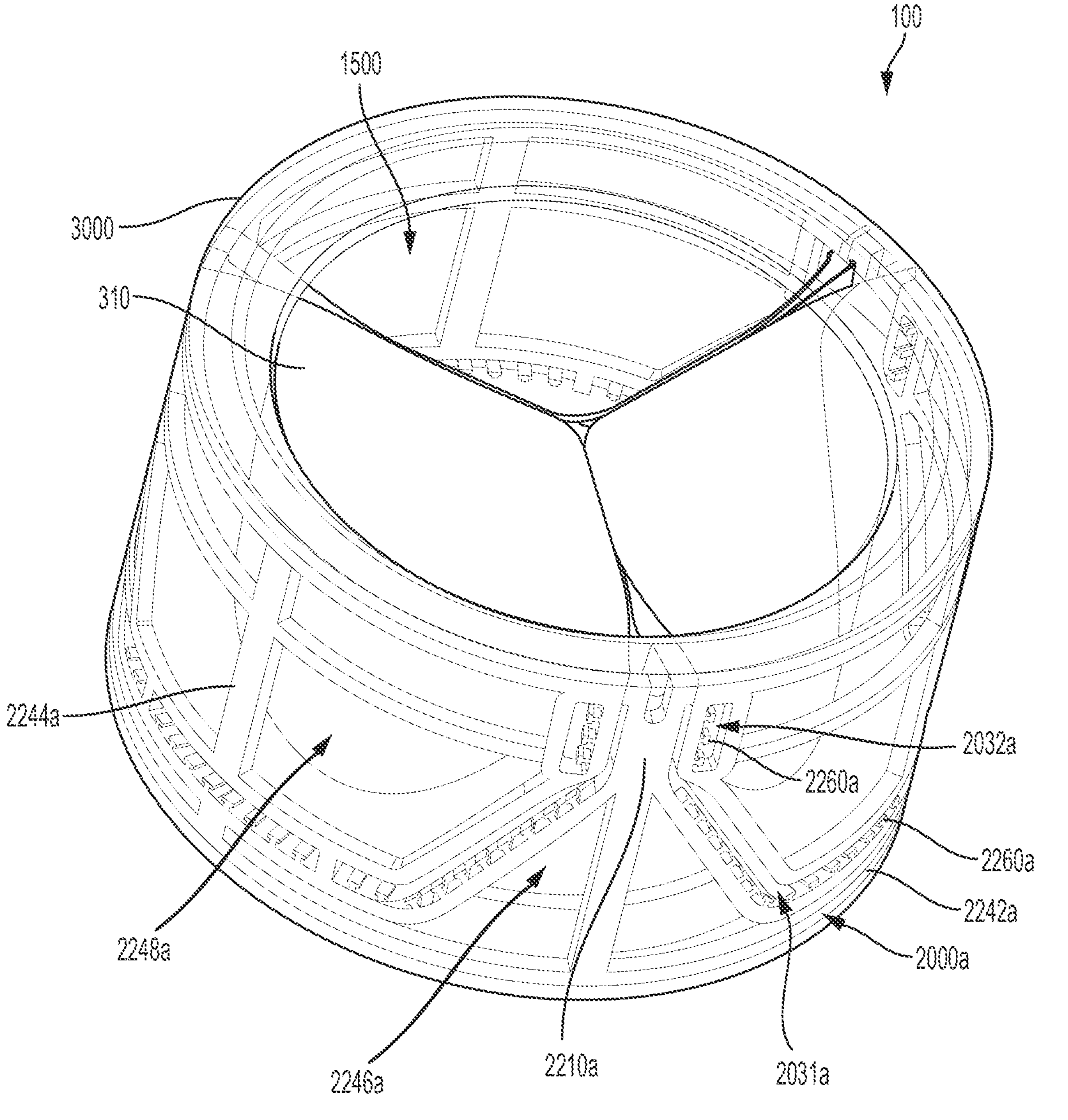
FIG. 40 is a perspective view of an illustration of another example jacket coupled to a prosthetic valve, in accordance with an embodiment.
Figure 41:
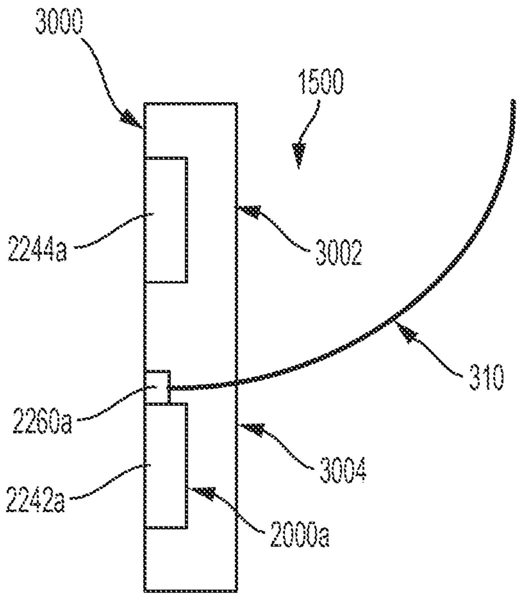
FIG. 41 is a cross-sectional illustration of the jacket and the prosthetic valve shown in FIG. 40, in accordance with an embodiment.

42A-42B are illustrations of a leaflet arranged within the jacket shown in FIGS. 40-41, according to some embodiments.

DETAILED DESCRIPTION

The present disclosure relates to prosthetic valves used for cardiac valve replacement or other applications associated with native valve or other valve orifices, and related systems, methods, and apparatuses. In various embodiments, the prosthetic valve is operable as a one-way prosthetic valve that defines a valve orifice into which leaflets open to permit flow and close so as to block or occlude the valve orifice and partially or entirely prevent flow in response to differential fluid pressure.

In the instant disclosure, the examples are primarily described in association with surgical or transcatheter cardiac valve applications, although it should be readily appreciated embodiments within the scope of this disclosure can be applied toward any prosthetic valve or mechanism of similar structure and/or function. For example, the prosthetic valve 100 of FIG. 1A can be applied in non-cardiac applications, such as respiratory or gastrointestinal tract applications. Implantable valve orifices include anatomical structures into which a prosthetic valve can be placed. Such anatomical structures include, but are not limited to, a location wherein a cardiac valve may or may not have been surgically removed. Other anatomical structures that can receive a prosthetic valve include, but are not limited to, veins, arteries, ducts and shunts. A valve orifice or implant site may also refer to a location in a synthetic or biological conduit that may receive a prosthetic valve.

The term "leaflet" as used in the context of prosthetic valves is generally a flexible component operable to move between an open and closed position under the influence of pressure differentials. In an open position, the leaflet allows blood to flow through the prosthetic valve. In a closed position, the leaflet substantially blocks retrograde flow through the prosthetic valve. In embodiments comprising multiple leaflets, each leaflet cooperates with at least one neighboring leaflet to block the retrograde flow of blood. Examples of suitable leaflet constructions and methods of attachment to leaflet frames are illustrated and described in U.S. patent application Ser. No. 13/833,650, U.S. Pat. No. 9,855,141 to Dienno referred to above, and U.S. Pat. No. 9,801,712 to Bruchman, the contents of each of which are incorporated herein by reference.

Various embodiments provided herein relate to a non-sewn or minimally sewn, mechanically coupled leaflet that is coupled, in a mechanical manner by way of leaflet frame projections, to a leaflet frame along a leaflet attachment region or a section thereof. Described leaflet frame projections allow for simple, reproducible coupling of a leaflet to a leaflet frame, which can be beneficial in either a manufacture or a research setting. A leaflet frame projection on the leaflet frame can be an integral part of the leaflet frame that projects from one or more leaflet retention surfaces. In accordance with an embodiment, the leaflet frame projections are configured to extend through the leaflet attachment region. In accordance with an embodiment, the leaflet frame projections are configured to extend through an aperture defined by the leaflet in the leaflet attachment region.

Some embodiments provided herein relate to leaflets made from a flat pattern. The leaflet can be made separately from the leaflet frame and then upon attachment to the leaflet frame, the leaflet obtains its operable shape, as the shape of leaflet frame elements, the two-dimensional shape of the leaflet, and the line of attachment are the primary determinants of the resulting three-dimensional operable shape of the leaflet. Thus, in some embodiments, this aspect can negate the need for leaflet shape-setting to a three-dimensional shape.

As the leaflets and leaflet frames can be manufactured independently and the attachment process does not require sewing or adhesion/thermal bonding (though sewing and adhesion/thermal bonding remain available as secondary securement options), the process of producing a prosthetic valve may be simplified, which can translate to manufacturing efficiencies. Moreover, embodiments provided herein can be particularly useful in a research context because of the option of a simplified process in making a leaflet and the leaflet frame and coupling the two together, allowing for quick prototyping.

In accordance with a present disclosure, a prosthetic valve can comprise a leaflet frame defining an annular ring and having a leaflet retention surface configured to impart a shape to the leaflet that provides proper function of the valve and one or more leaflet retention surfaces to facilitate leaflet retention to the leaflet frame. A plurality of leaflet frame projections that are spaced from each other can be coupled to or integral with the leaflet retention surface. The leaflet frame projections are configured to assist in maintaining a coupling between the leaflet and the leaflet frame.

The prosthetic valve also comprises one or more leaflets. In some embodiments, each leaflet includes a leaflet attachment region and a region terminating at a leaflet free edge, as will be discussed in greater detail below. In some embodiments, the leaflet attachment region of the leaflet includes a plurality of leaflet apertures spaced apart from each other and are complementary of the leaflet frame projections of the leaflet frame. In some embodiments, the leaflet frame projections extend through a corresponding one of the plurality of leaflet apertures when the two components are coupled together. In other words, in various embodiments, a spatial pattern of the leaflet frame projections is the same as a spatial pattern of the leaflet apertures. The coupling of the leaflet frame projections to the leaflets facilitates the retention of the leaflet on the leaflet frame. It is appreciated that embodiments of this disclosure are suitable for prosthetic valves having one, two, three, or more than three leaflets.

Figure 1B:
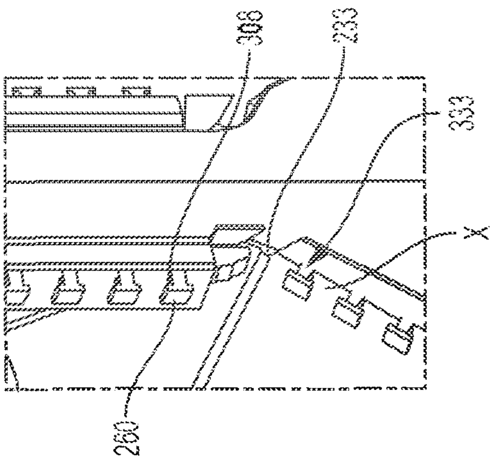
FIG. 1B is a magnified view of Box 1B in FIG. 1A.
Figure 1C:
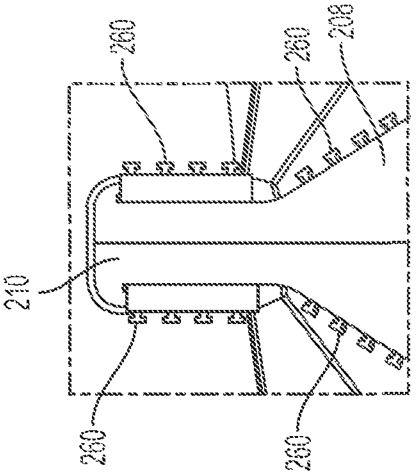
FIG. 1C is a magnified view of Box 1C in FIG. 1A.
Figure 1A:
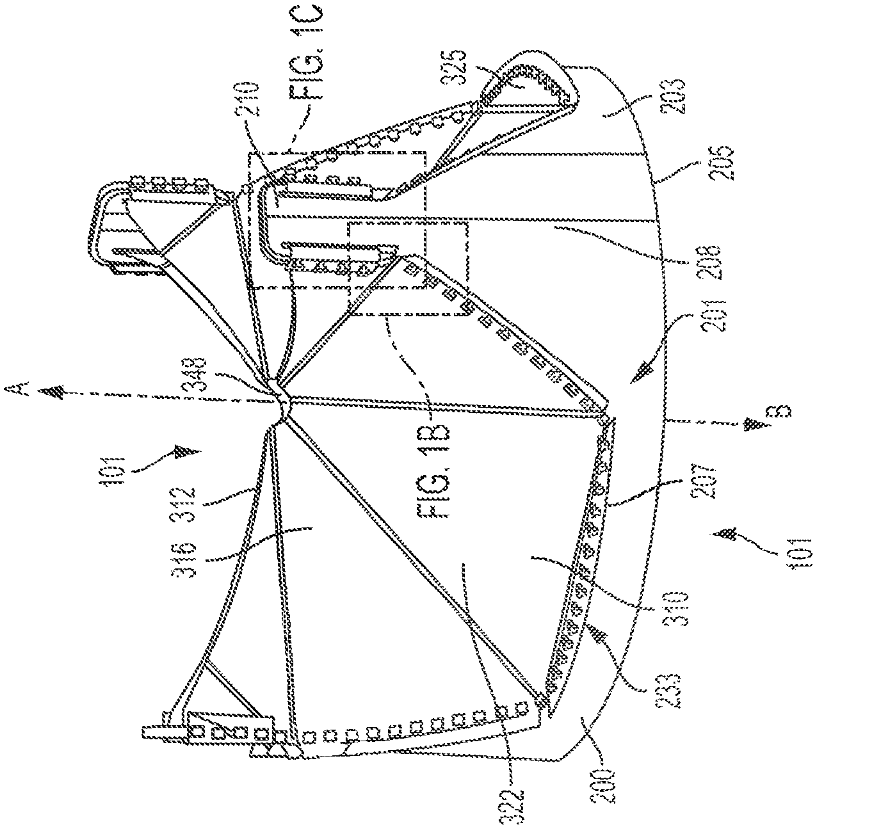
FIG. 1A is an outflow-side, perspective view of a prosthetic valve, according to some embodiments.

FIG. 1A is an outflow perspective view of a prosthetic valve 100, in accordance with an embodiment, shown in a closed configuration. FIG. 1B is a magnified view of Box 1B in FIG. 1A. FIG. 1C is a magnified view of Box 1B in FIG. 1A. FIG. 1C is a top view of the prosthetic valve 100 in FIG. 1A, also shown in a closed configuration. The components of the prosthetic valve 100 that can be observed in FIG. 1A include a plurality of leaflets 310 and a leaflet frame 200 that includes a plurality of commissure posts 210 flanked on each side by leaflet window frame element(s) (e.g., two commissure post supports 208 and a leaflet window base 207 therebetween) that define the leaflet window 204 (labeled in FIG. 2A). In various embodiments, the leaflet free edges 312 of adjacently situated leaflets 310 come together at a coaptation region 316. In some embodiments, the leaflet free edges 312 of adjacently situated leaflets come together in a Y-shaped pattern when viewed from above (see, e.g., FIG. 1D). In various embodiments, coaptation of adjacent leaflets operates to obstruct the flow of fluid (e.g., blood) through the prosthetic valve 100. It will be appreciated that, in some instances, coaptation of adjacent leaflets may operate to completely block the flow of fluid (e.g., blood) through the prosthetic valve 100, while in others coaptation of adjacent leaflets may operate to block less than all of the flow of fluid (e.g., blood) through the prosthetic valve 100.

In some embodiments, the leaflet free edges 312 of adjacently situated leaflets coapt in response to a pressure on the leaflet outflow side A exceeds a pressure on the leaflet inflow side B of the prosthetic valve 100. In some embodiments, the pressure on the leaflet outflow side A increases in response a contraction of a ventricle, as those of skill will appreciate. Conversely, in various embodiments, the leaflet free edges 312 of adjacently situated leaflets 310 move apart to open the prosthetic valve 100 and to let fluid (e.g., blood) flow through the prosthetic valve 100 (e.g., from the leaflet inflow side B to the leaflet outflow side A) when the pressure on the leaflet inflow side B exceeds the pressure on the leaflet outflow side A.

FIG. 1B shows a magnified view of a leaflet frame projection 260 on the leaflet frame 200 about which a leaflet aperture 308 is disposed. In various embodiments, a leaflet aperture 308 is disposed about a leaflet frame projection 260 after a portion of the leaflet 310 is folded over or otherwise wrapped and/or wound about a portion of the leaflet frame 200, as discussed in greater detail below. In the example illustrated in FIGS. 1B and 1C, leaflet frame projections 260 are located along a plurality of surfaces and/or edges of the leaflet frame 200.

Figure 2A:
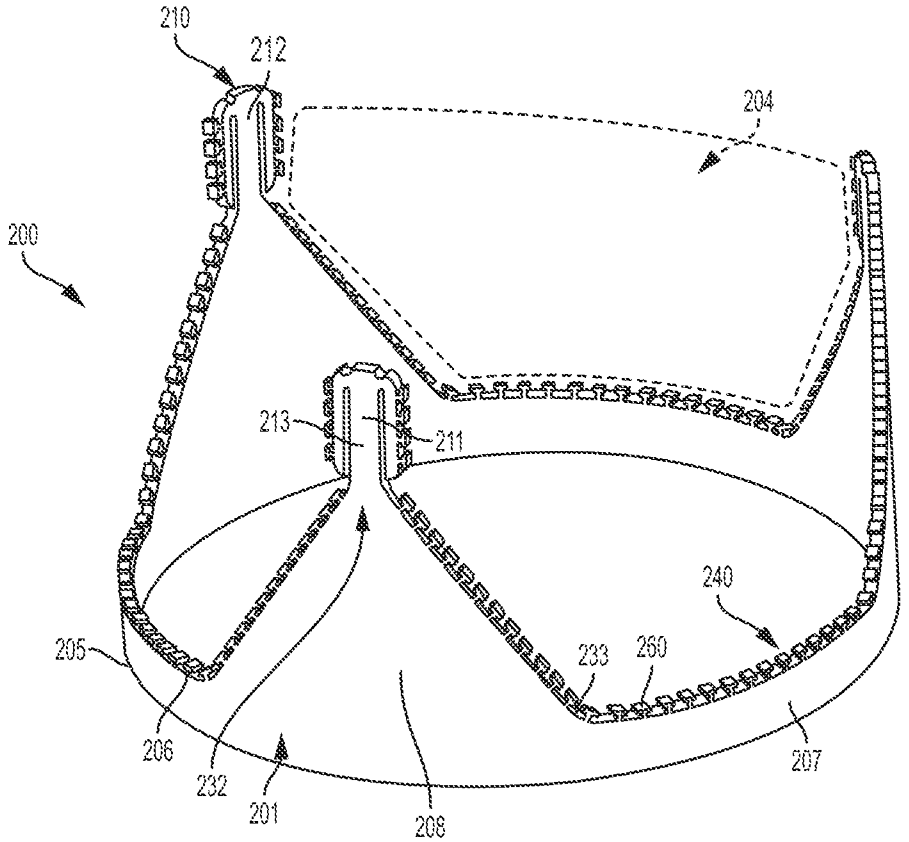
FIG. 2A is an outflow-side, perspective view of a leaflet frame, according to some embodiments.
Figure 2B:
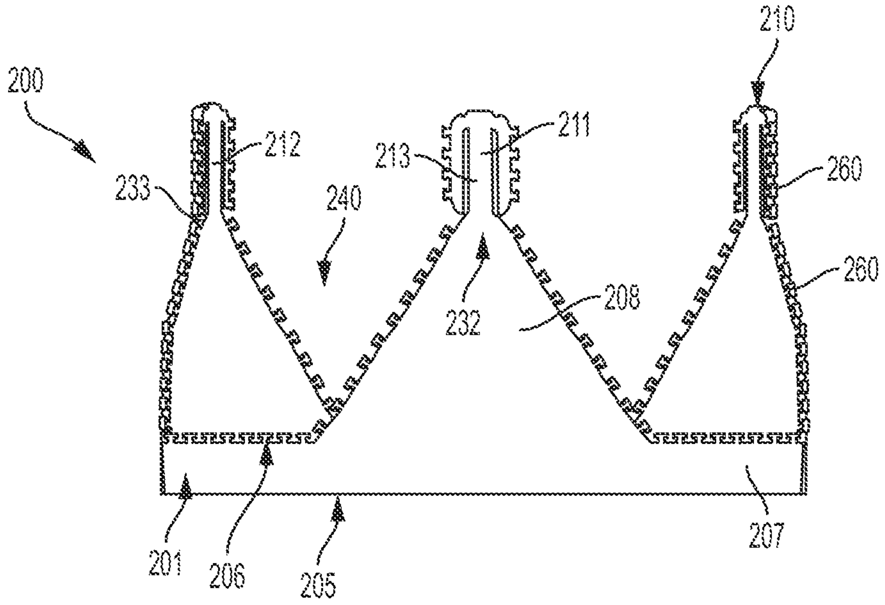
FIG. 2B is a side view of the leaflet frame embodiment of FIG. 2A.
Figure 2C:
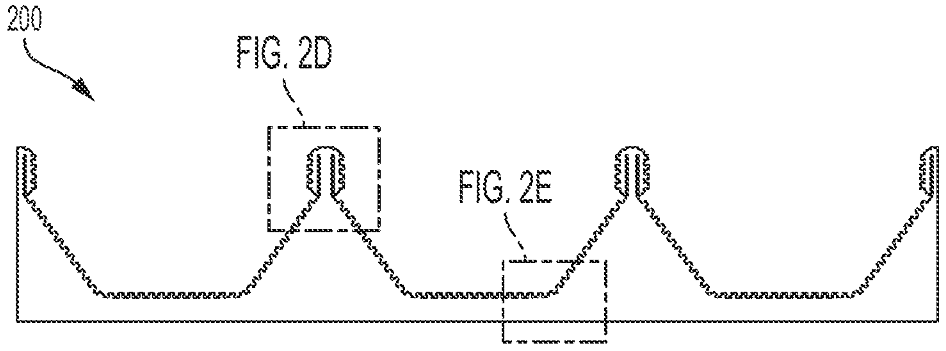
FIG. 2C is a representation of the leaflet frame shown in FIG. 2A that has been unrolled to a flat orientation.
Figure 2D:
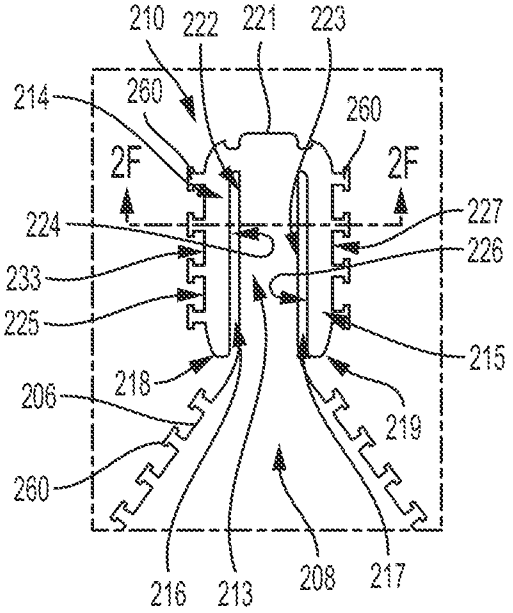
FIG. 2D is a magnified view of Box 2D in FIG. 2C.
Figure 2E:
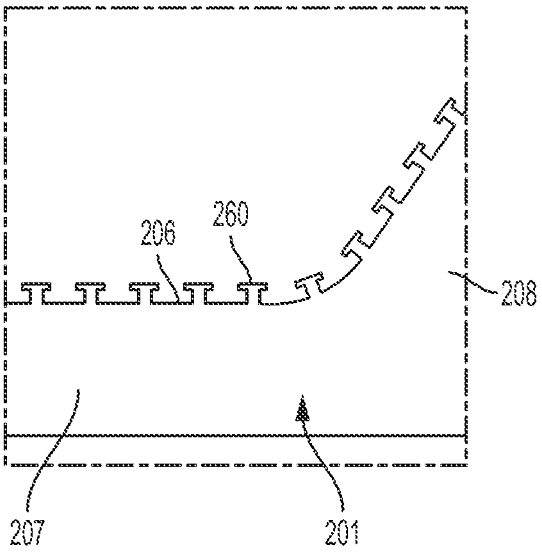
FIG. 2E is a magnified view of Box 2E in FIG. 20.

FIGS. 2A and 2B show a perspective view and a side view, respectively, of the leaflet frame 200 in accordance with an embodiment. FIG. 2C is a representation of the leaflet frame shown in FIG. 2A that has been longitudinally cut, opened, and laid flat to better illustrate the elements of the leaflet frame 200. FIG. 2D is a magnified view of circle 2D in FIG. 2C. FIG. 2E is a magnified view of circle 2E in FIG. 2C.

Figure 7A:
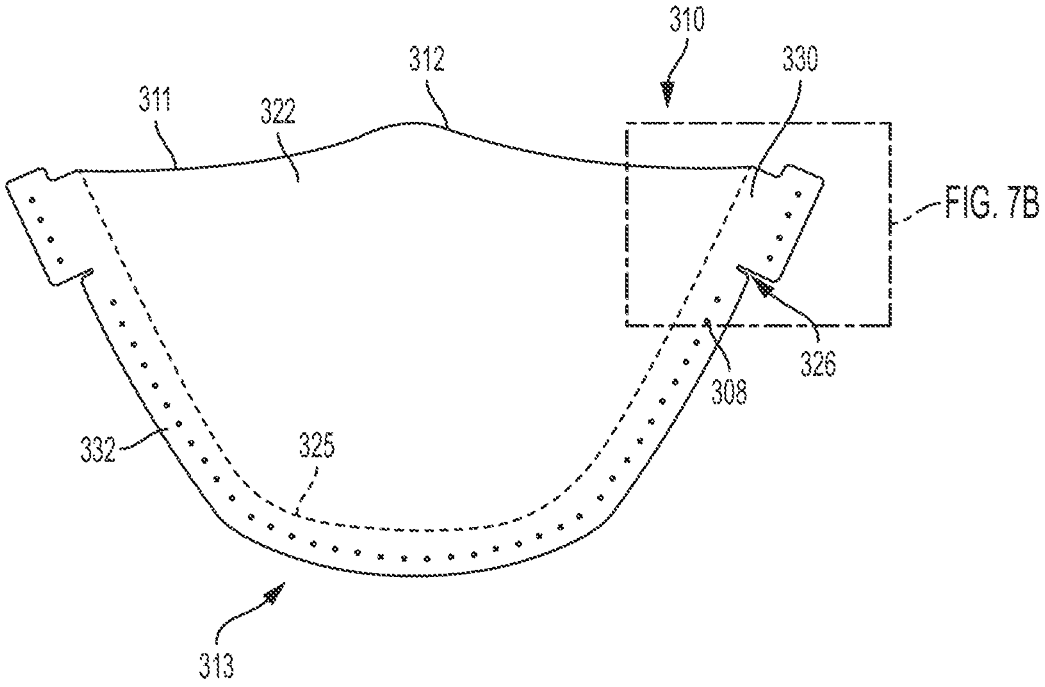
FIG. 7A is a top view of the leaflet of the prosthetic valve of FIG. 1A in a flattened configuration.
Figure 7B:
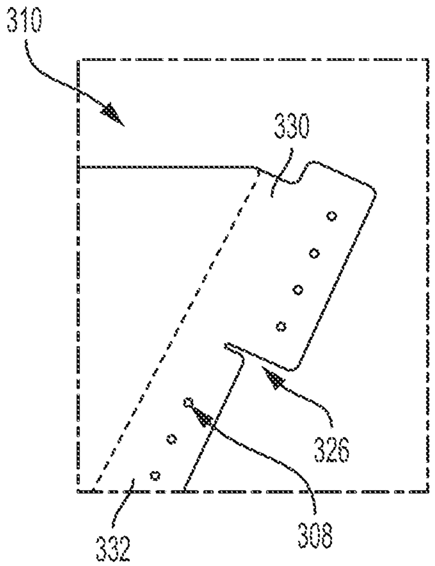
FIG. 7B is a magnified view of Box 7B in FIG. 7A.

FIG. 7A shows a top view of the leaflet of FIG. 1A in a flat configuration, and FIG. 7B shows a magnified view of Box 7B of FIG. 7A. While the leaflets 310 of FIGS. 7A and 7B are shown flat to better show the shape and features, it is understood that the shape of the leaflet when coupled to the frame is determined, at least in part, by the shape of the leaflet frame, the shape of the leaflet attachment surface, and the fluid pressure that the leaflet encounters during operation, for example.

In various embodiments, the leaflet frame 200 defines an annular shape having a leaflet frame inner surface 202 and a leaflet frame outer surface 203 opposite the leaflet frame inner surface 202. In some embodiments, the leaflet frame 200 further includes a leaflet frame first edge 205 and a leaflet frame second edge 206 opposite the leaflet frame first edge 205.

In various embodiments, the various leaflet frames described herein can be etched, cut, laser cut, stamped, three-dimensional printed, or wire wound, among other suitable processes. The leaflet frames can be self-expanding or balloon expandable (e.g., when configured for transcatheter implantation) or non-expandable (e.g., when configured for surgical implantation). The leaflet frames can comprise materials, such as, but not limited to, any metallic or polymeric material, such as an elastically (e.g., nitinol) or plastically (e.g., stainless steel) deformable metallic or polymeric material that is generally biocompatible. Other materials suitable for any of the leaflet frames described herein include, but are not limited to, other titanium alloys, stainless steel, cobalt-nickel alloy, polypropylene, acetyl homopolymer, acetyl copolymer, a drawn filled tube (e.g., nitinol wire with a platinum core), other alloys or polymers, or any other material that is generally biocompatible having adequate physical and mechanical properties to function as a frame as described herein. The leaflet frames may be formed into an annular structure or a sheet of material, with the sheet then formed into an annular structure. The leaflet frame shape can be configured for transcatheter or surgical devices.

Additionally, in various embodiments, the leaflet frame 200 can comprise any rigid or semi-rigid biocompatible material. Materials suitable for the leaflet frame 200 include, but not limited to, titanium alloys, stainless steel, cobalt-nickel alloy, polypropylene, acetyl homopolymer, acetyl copolymer, other alloys or polymers, or any other material that is generally biocompatible having adequate physical and mechanical properties to function as the leaflet frame 200 as described herein. In some embodiments, the leaflet frame 200 can be a shape-memory material, such as nitinol, a nickel-titanium alloy.

In various embodiments, the leaflet frame 200 can be wrapped with a material, such as an ePTFE membrane, suitable for promoting tissue in-growth. All surfaces of the leaflet frame can be wrapped with a film prior to leaflet attachment. Additionally or alternatively, a polyethylene terephthalate fabric (e.g., that sold under the trade name "DACRON") suitable for promoting tissue ingrowth could be coupled to one or both of the leaflet frame inner surface and the leaflet frame outer surface of the leaflet frame and optionally between the leaflet frame projections prior to leaflet attachment.

In accordance with some embodiments, the leaflet frame 200 is annular about a central longitudinal axis A-B of the prosthetic valve 100, as shown in FIG. 1A. In some embodiments, the leaflet frame 200 defines a plurality of leaflet windows 204, each of which are complementary to a shape of a leaflet attachment region 330 of a leaflet 310. In some embodiments, the leaflet windows 204 are defined, in part, by a leaflet window base 207 and a plurality of commissure post supports 208. In the illustrated example of FIG. 1A, a leaflet window base 207 is flanked on each side by commissure post supports 208 that together define three sides of an arced isosceles trapezoid, wherein the leaflet frame second edge 206 at the leaflet window base 207 is substantially flat.

In some embodiments, the commissure posts 210 of the leaflet frame 200 are equally spaced from one another around the leaflet frame 200. In some embodiments, the commissure post support 208 includes that portion of the leaflet frame 200 that is disposed under each commissure post 210 and between adjacent leaflet windows 204. In some embodiments, an opening or aperture is formed in one or more of the commissure post support 208, as discussed further below.

On portions of the leaflet frame second edge 206 at the commissure post supports 208, the leaflet window base 207, and the commissure post 210, referred to as leaflet retention surfaces 233, are located a plurality of leaflet frame projections 260. Each of the plurality of the leaflet frame projections 260, but not necessarily all of the leaflet frame projections 260, is disposable within a corresponding one of a plurality of leaflet apertures 308 of a leaflet 310, as discussed further below. Exemplary projection-aperture junctions 333 are illustrated in the magnified view of Box 1B shown in FIG. 1B.

As shown, the leaflet frame projections 260 can extend from one or more leaflet retention surfaces 233 and can be configured to each extend through one of the leaflet apertures 308 to restrain the leaflet 310 and/or impede leaflet uplift away from the leaflet retention surface 233 in some embodiments. The leaflet frame projections 260 can be an integral part of or unitary with the leaflet frame 200 and project from the one or more leaflet retention surfaces 233, such as the leaflet frame second edge 206, in a direction normal to the surface (as shown) or off-normal (i.e. at an angle of less than 90 degrees to the leaflet retention surface 233). In various embodiments, each leaflet frame projection 260 of the leaflet frame 200 projects from the leaflet retention surface 233 in a direction that is substantially normal to the leaflet retention surface 233. In various other embodiments, however, it will be appreciated that one or more of the leaflet frame projections 260 project from a leaflet retention surface in a direction different from substantially normal to the leaflet retention surface 233. For example, one or more leaflet frame projections 260 may extend substantially parallel with central longitudinal axis A-B, which may be different than a direction substantially normal to a leaflet retention surface for those leaflet retention surfaces that are not perpendicular (or are otherwise angled relative to) the central longitudinal axis A-B. Various configurations of leaflet frame projections 260 are shown in FIGS. 3A-3E, 4A-4B, 5A-5B, and 6A-6B.

In various embodiments, adjacently situated leaflet frame projections 260 can be spaced-apart from each other a distance X (e.g., see FIG. 1B) that sufficiently disperses the load on the leaflet attachment region 330 of the leaflet 310 without significantly affecting the structural integrity thereof. In addition, the distance can be small enough for the leaflet attachment region 330 to abut sufficiently with the leaflet retention surface 233 so that fluid leakage between the two is insignificant or non-existent. Various non-limiting example distances are within a range of between 0.5 mm to 2 mm, such as 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, or 2 mm.

In various embodiments, a leaflet frame projection 260 is coupled to or unitary with a restraining element configured to provide a mechanical interference to impede leaflet decoupling from each leaflet frame projection 260. For instance, in some embodiments, the leaflet frame projection 260 itself can be configured to impede leaflet decoupling. In particular, as shown in FIGS. 3A-3E, a leaflet frame projection 260 can define a projection base portion 262 and a projection head portion 264 that defines a projection tip 266 (e.g., a projection head portion tip).

In various embodiments, the leaflet frame 200 is operable to mechanically couple and support the leaflets 310 by way of, at least in part, a plurality of the leaflet frame projections 260 that are spaced-apart and project from one or more leaflet retention surfaces 233 of the leaflet frame 200 (e.g., the leaflet frame 200 is operable to engage the leaflets 310). In various embodiments, the one or more leaflet retention surfaces 233 are one or more leaflet frame edges, such as a leaflet frame first edge 205, a leaflet frame second edge 206, and one or more of the various edges of the commissure post 210 as discussed below. As mentioned above, in various embodiments, the leaflet frame projections 260 are each configured to extend through a leaflet aperture 308 defined by the leaflet 310 within the one or more leaflet attachment regions 330 of the leaflet 310. In some embodiments, the leaflet frame projections 260 can have a tenon-like shape that operates to minimize a potential for decoupling (or "backing-off") of the leaflet 310 from the leaflet frame projections 260, as discussed further below.

In some embodiments, the leaflet frame 200 defines an annular shape and has a central longitudinal axis A-B (shown in FIG. 1A). In various embodiments, the leaflet frame includes a plurality of commissure posts 210 to which one or more leaflets attach. In some embodiments, the commissure posts are spaced from one another. In some embodiments, one or more of the commissure posts extend substantially parallel with the central longitudinal axis of the leaflet frame (e.g., axis A-B). In various embodiments, the commissure posts 210 are arranges such a leaflet window 204 is defined between adjacently situated commissure posts 210. It will be appreciated that, in various embodiments, the leaflet frame 200 includes a plurality of leaflet windows 204. In some embodiments, each commissure post 210 extends from one or more commissure post supports 208. In various embodiments, the one or more commissure post supports 208 extend from or are otherwise supported by a base portion 201 of the leaflet frame 200 and include a plurality of sides, including a commissure post support first side 236 and a commissure post support second side 238. In some embodiments, one or more of the commissure post supports 208 include one or more apertures, as discussed in greater detail below. That is, while the leaflet frame 200 illustrated in FIGS. 1A-1D and 2A-2F include commissure post supports 208 below the commissure posts 210 that includes a continuous wall, in various embodiments, one or more of the commissure post supports 208 include an opening or aperture. For instance, in some embodiments, one or more of the commissure post supports 208 are configured as an open triangular frame defined by commissure post support first and second sides 236 and 238 and base portion 201.

In exemplary illustrations shown in FIGS. 1A and 2A, each leaflet window 204 is further defined by a leaflet frame second edge 206. In some embodiments, the leaflet frame second edge 206 extends between adjacently situated commissure posts 210. Specifically, in some embodiments, the leaflet frame second edge 206 extends along a plurality of commissure post supports 208 from which adjacently situated commissure posts 210 extend, and along a leaflet window base 207 situated between the plurality of commissure post supports 208. In some embodiments, the leaflet frame second edge 206 defines a leaflet frame concavity 240 within which a leaflet window 204 is defined. Generally, the leaflet frame concavity 240 can be curved, angular, or include a combination of angled and curved features. In various embodiments, a leaflet window 204 flanks each side of a commissure post 210. As illustrated in FIG. 1A, the leaflet window base 207 and the commissure post supports 208, in combination with two adjacently situated commissure posts 210 form a perimeter of leaflet support structure that supports a leaflet 310 (with the exception of the leaflet free edge 312).

Figure 9A:
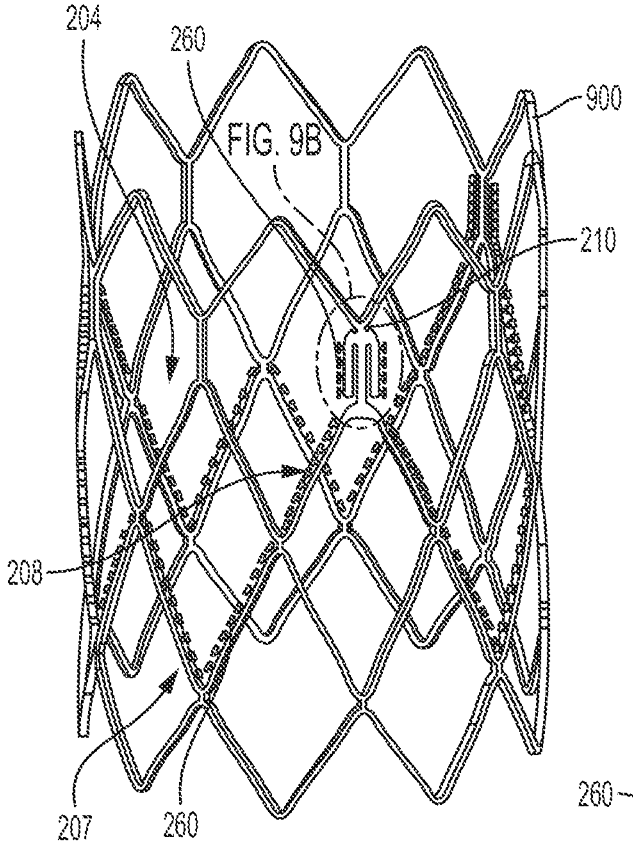
FIG. 9A is a perspective view of a leaflet frame for use in a transcatheter delivery procedure, according to some embodiments.

As mentioned above, in various embodiments, a commissure post 210 extends from or is otherwise supported by a commissure post support 208. In some embodiments, an apex 232 is formed at the intersection or transition from the commissure post support 208 and the commissure post 210. In some embodiments, the apex 232 is formed at a convergence of the commissure post support first and second sides 236 and 238, as shown in FIG. 2B. In some embodiments, the apex 232 is formed at a convergence of two leaflet frame elements (e.g., two commissure post supports 208), as shown in FIG. 9A.

Generally, each commissure post 210 includes a post outer side 211 and a post inner side 212 opposite the post outer side 211. In some embodiments, the post outer side 211 includes a surface that corresponds with or is otherwise continuous with the leaflet frame outer surface 203. Similarly, in some embodiments, the post inner side 212 includes a surface that corresponds with or is otherwise continuous with a leaflet frame inner surface 202.

In various embodiments, each commissure post 210 includes a spine 213, a plurality of tines extending from the spine 213, and a plurality of slots extending along and situated between the tines and at least the spine 213. It will be appreciated that the slots are generally free of leaflet frame projections unless specified otherwise. The spine 213 is generally situated between the first and second tines 214 and 215 and extends from the commissure post support 208 to a commissure tip 221. In some examples, the commissure tip 221 defines a free end of the commissure post 210. As discussed in greater detail below, the spine 213 effectuates a separation between adjacently situated leaflets 310 at the commissure post 210. Thus, a width of the spine 213 is generally selected based on a desired degree of separation between adjacently situated leaflets 310 at the commissure post 210. For example, wider spines 213 are associated with larger degrees of separation between adjacently situated leaflets 310 at the commissure post 210. It will be appreciated that configurations that include wider spines imparting larger degrees of separation between adjacently situated leaflets 310 at the commissure post 210 may be associated with some flow of fluid through these areas even during coaptation of the adjacently situated leaflets 310. Flow in such configurations operates to minimize thrombosis formation in these areas. Accordingly, the width of the spine 213 can be selected based on a desired degree of flow through the prosthetic valve 100 during coaptation (e.g., valve closure).

In various embodiments, the tines of each commissure post 210 extend from or are otherwise coupled with the spine 213. For example, as shown in FIG. 2D, the commissure post 210 includes a first tine 214 and a second tine 215 that each extend from the spine 213. In the example of FIG. 2D, the first and second tines 214 and 215 are illustrated as extending from the spine 213 at or proximate to the commissure tip 221. However, in some embodiments, one or more of the first and second tines 214 and 215 may extend from the spine at or proximate to the commissure post support 208, or apex 232, or from any point between the commissure tip 221 and the commissure post support 208 or apex 232. In some embodiments, the first and second tines 214 and 215 converge from either side of the spine 213 form the commissure tip 221.

In various embodiments, one or more of the tines of the commissure post 210 includes a free end or an end that is not otherwise coupled to or integral with the leaflet frame 200 (including the commissure post 210), but instead is an extension of a portion of the tine that is coupled or otherwise integral with the leaflet frame 200 (including the commissure post 210). For example, as shown in FIG. 2E, the first tine 214 includes a free end 218, and the second tine 215 includes a free end 219. However, as discussed in greater detail below, in various embodiments, one or more of the tines of the commissure post 210 is configured such that each respective end of the tine is coupled to or otherwise integral with the leaflet frame 200. That is, in some embodiments, one or more of the tines does not include a free end.

As mentioned above, one or more of the commissure posts 210 generally includes a plurality of slots situated between the tines and the spine 213 of the commissure post 210. Put different, in various embodiments, one or more of the tines of the commissure post 210 are offset from the spine 213 such that one or more slots or reliefs are formed therebetween. The slots, illustrated as a first slot 216 and a second slot 217 in FIG. 2D extend along either side of the spine 213 between the spine 213 and the first and second tines 214 and 215. In some embodiments, the spine 213 includes a first edge 222 and a second edge 223. In some embodiments, the first edge 222 of the spine 213 faces the first tine 214 and defines the first slot 216, in part. Similarly, in some embodiments, the second edge 223 of the spine 213 faces the second tine 215 and defines the second slot 217, in part.

One or more of the slots of the commissure posts 210 may extend or be oriented such that a longitudinal length of the slot is substantially parallel with the central longitudinal axis A-B of the leaflet frame 200. In some embodiments, the slots of the commissure posts 210 are parallel to one another. Additionally or alternatively, one or more of the slots of the commissure posts 210 may be nonparallel with one another. For example, the slots of the commissure posts 210 may diverge from one another at location below the commissure tip 221 in a direction of the outflow side A, towards the commissure tip 221. In some examples, one or more of the slots of the commissure posts 210 may curve slightly or include a nonlinear portion along a length of the slot.

In various embodiments, each slot of the commissure post 210 is dimensioned to have a width that accommodates the thickness of at least one of the leaflets 310, and a length that accommodates a portion of a length of the leaflet attachment region 330 that is couplable to the respective tine of the commissure post 210, as discussed in additional detail below.

In various embodiments, the first slot 216 is further defined by a first interior edge 224 of the first tine 214. As illustrated in FIG. 2D, the first interior edge 224 of the first tine 214 extends along a portion of the first tine 214 facing the spine 213 of the commissure post 210 between the first free end 218 of the first tine 214 and a region where the first tine 214 couples to or otherwise extends from the commissure post 210. Similarly, in various embodiments, the second slot 217 is further defined by a second interior edge 226 of the second tine 215. As illustrated in FIG. 2D, the second interior edge 226 of the second tine 215 extends along a portion of the second tine 215 facing the spine 213 of the commissure post 210 between the second free end 219 of the second tine 215 and a region where the second tine 215 couples to or otherwise extends from the spine 213. It will be appreciated that in embodiments where the tines of the commissure post do not include a free end, the interior edges of the respective tines generally extend between regions where the tines couple to or otherwise extend from the leaflet frame 200 (including the commissure post 210). As discussed in greater detail below, each slot of the commissure post 210 is configured to accommodate a portion of a leaflet 310 being extended therethrough for mating or otherwise coupling the leaflet 310 to the leaflet frame 200.

It will be appreciated that in embodiments where the tines of the commissure posts 210 include a free end, the slots defined between such tines and the spine of the commissure post 210 are open slots. That is, the slots are open on one end, or otherwise include at least one end that is open and accessible from an end of the slot, as opposed to be accessible only from the post outer side 211 or the post inner side 212. Configurations including slots having at least one open end generally ease assembly as the leaflet 310 can be slid into the slot from the open end of the slot as opposed to requiring a portion of the leaflet 310 to be threaded into a closed slot, as those of skill should appreciate.

In addition to an interior edge, each tine of the commissure post 210 generally includes an exterior edge. Generally, as discussed in greater detail below the interior and exterior edges of the tines of the commissure post 210 interface with a leaflet 310 and facilitate a couple between the leaflet 310 and the leaflet frame 200. In some embodiments, the exterior edge of a tine generally extends between a first region where the tine couples to or otherwise extends from the spine 213 and a free end of the tine (or alternative a second region where the tine couples to or otherwise extends from the spine 213 or other portion of the leaflet frame 200). As shown in FIG. 2D, the first tine 214 includes a first exterior edge 225 that extends between the first free end 218 of the first tine 214 and the commissure tip 221. Similarly, the second tine 215 includes a second exterior edge 227 that extends between the second free end 219 of the second tine 215 and the commissure tip 221.

In various embodiments, the first edge 222 of the spine 213 is continuous with or otherwise intersects with the first interior edge 224 of the first tine 214. Similarly, in various embodiments, the second edge 223 of the spine 213 is continuous with or otherwise intersects with the second interior edge 226 of the second tine 215. In embodiments including tines with free ends, a transition between the interior and exterior edges of the tines occurs at or proximate to the free end of the tine. For example, a transition between or intersection of the first interior edge 224 and the first exterior edge 225 of the first tine 214 occurs at or proximate to the first free end 218 of the first tine 214. Similarly, a transition between or intersection of the second interior edge 226 and the second exterior edge 227 of the second tine 215 occurs at or proximate to the second free end 219 of the second tine 215.

In various embodiments, one or more leaflet frame projections 260 extend from the first and second exterior edges 225 and 227 of the first and second tines 214 and 215, respectively. Thus, in various embodiments, one or more of the tines of the commissure post 210 includes one or more leaflet frame projections 260 that extend from a surface opposite a surface of the tine defining a slot through which a leaflet 310 extends for the purpose of mating or otherwise coupling the leaflet 310 to the leaflet frame 200.

As discussed above and further below, such a configuration provides that a portion of a leaflet 310 may be wrapped (completely or partially) about a respective tine (e.g., one or more edges of the respective tine and/or one or more surfaces of the respective tine) prior to being secured to the one or more leaflet frame projections 260 extending from the respective tine. In various embodiments, wrapping the leaflet 310 about one or more portions of the leaflet frame 200 prior to securing of the leaflet 310 to the leaflet frame projections 260 operates to maintain a coupling between the leaflet 310 and the leaflet frame 200. It will be appreciated that one factor contributing to leaflet failure (e.g., by way of the leaflet tearing and/or detaching from the leaflet frame) is that a peak stress in the leaflet generally occurs at the commissure region (e.g., where the leaflet attaches, engages, or is otherwise coupled to the leaflet frame) when the prosthetic valve is closed and under fluid backpressure. It has been observed that wrapping the leaflet 310 about a portion of the leaflet frame 200 prior to securing of the leaflet 310 to the leaflet frame projections 260 extending from a respective tine of the commissure post 210 helps mitigate undesirable loading and stress concentrations in the leaflet 310 (due at least in part to a "capstan effect"), and helps minimize a potential for failure of the leaflet 310.

As discussed above, the leaflet frame 200 includes a plurality of leaflet frame projections 260 that facilitate a mechanical interference to impede leaflet decoupling from each leaflet frame projection 260, according to some embodiments. Referring again to FIGS. 3A-3E, in various embodiments, the projection base portion 262 meets the leaflet retention surface 233 (in this case, the leaflet frame second edge 206) at one end and the projection head portion 264 at its opposite end. In some embodiments, the projection head portion 264 meets the projection base portion 262 at one end and terminates at the projection tip 266 at its opposite end.

Figure 3A:
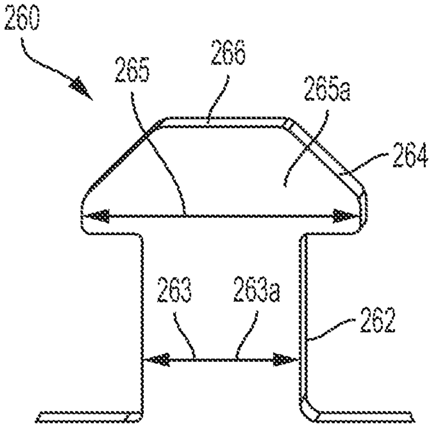
FIGS. 3A to 3E are perspective views of various leaflet frame projections defining various tenon-like shapes, according to some embodiments.
Figure 3B:
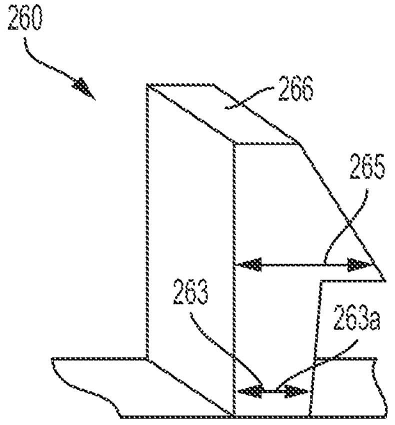
Figure 3C:
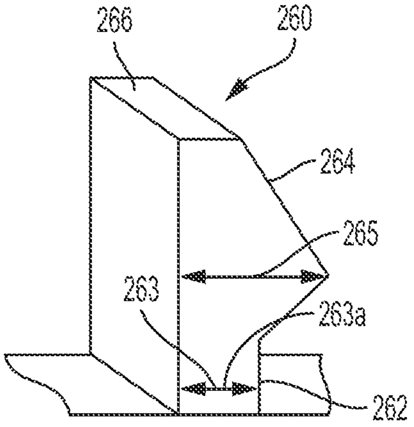
Figure 3D:
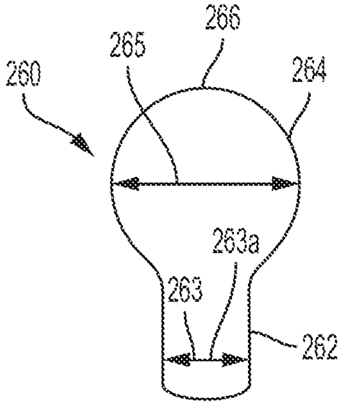

In various embodiments, the projection head portion 264 has a wider second transverse dimension 265 than a first transverse dimension 263 of the projection base portion 262. The transition between the wider projection head portion 264 and the narrower projection base portion 262 can be gradual, abrupt, or something therebetween. For example, the projection head portion 264 can define a bulbous shape (as shown in FIG. 3D), or an angular overhang. In various embodiments, the relative difference in the largest second transverse dimension 265 within the projection head portion 264, referred to as a projection head portion transverse dimension **265*a*, compared to the narrowest first transverse dimension 263 within the projection base portion 262, referred as the projection base portion transverse dimension 263*a*, can be between 20% to 160%, such as greater than 30%, 40%, 50%, 60%, 70%, 80%, 90%, 100%, 110%, 120%, 130% 140%, 150%, or any value or range derivable therein. In various embodiments, the narrowest first transverse dimension 263 within the projection base portion 262 can be directly adjacent the leaflet retention surface 233 with which the projection base portion 262** meets.

Figure 3E:
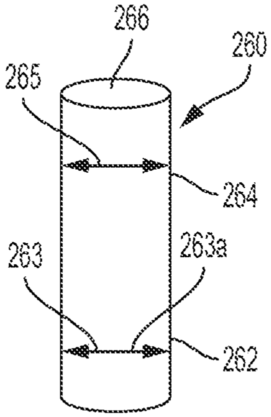

Other projection configurations are also contemplated and those illustrated and described herein should not be construed as limiting. For instance, in some other embodiments, the projection head portion 264 and the projection base portion 262 have the substantially same transverse dimension or cross-sectional area. For example, the leaflet frame projections 260 may define a helical column. In another example, the leaflet frame projection 260 is a straight post projecting from the leaflet retention surface 233, an embodiment of which is shown in FIG. 3E.

In various embodiments, the projection head portion 264 can be tapered such that the projection tip 266 has a smaller surface area than the cross-sectional area at the largest, transverse cross-section of the projection head portion 264. In addition, in some embodiments, a projection tip 266 is dimensioned such that the surface area of the projection tip 266 is less than the area of the leaflet aperture 308. It will be appreciated that this shape operates to help guide the leaflet 310 at one of the leaflet apertures 308 onto the leaflet frame projection 260 during the attachment process of the leaflet 310 to the leaflet frame 200 during manufacturing.

In some embodiments, the projection head portion 264 can be pointed to facilitate puncturing of the leaflets 310. Such examples may include forming the leaflet apertures 308 during the attachment process. That is, in some embodiments, the leaflet 310 does not include preformed leaflet apertures 308 (or alternatively includes less than all of the requisite leaflet apertures 308 required). In some embodiments, pointed head portions of the leaflet frame projections 260 can also facilitate puncturing of a conduit in the formation of a prosthetic valved conduit, described hereafter.

The cross-sectional shape of the projection base portion 262 can be any shape, such as triangular, rectangular (e.g., square) or rounded (e.g., oval or circle). In various embodiments, the shape and dimension of the projection base portion 262, particularly at the leaflet retention surface 233, is substantially the same as the shape and dimension of the leaflet aperture 308, except the leaflet aperture 308 can be slightly larger in dimension such that no strain or only negligible strain is placed on that portion of the leaflet attachment region 330 that defines the leaflet aperture 308 when seated adjacent the leaflet retention surface 233 of the leaflet frame 200 about the projection base portion 262.

Figure 4A:
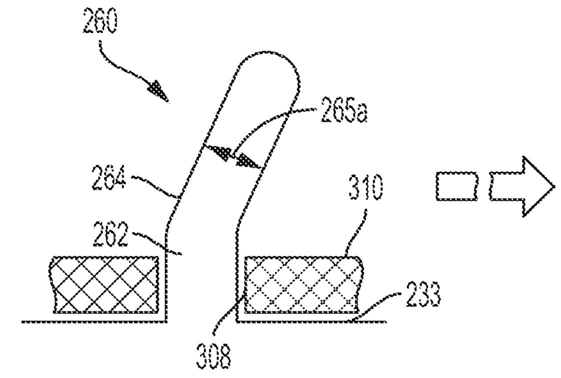
FIGS. 4A and 4B are side views of a leaflet frame projection, according to some embodiments.
Figure 4B:
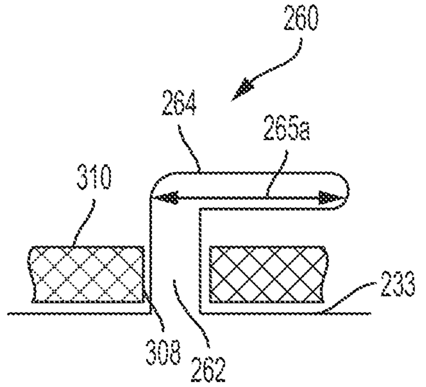

Other embodiments of the leaflet frame projections 260 include leaflet frame projections that are operable to change shape or deform so as to retain the leaflet 310 to the leaflet retention surfaces 233. In the illustrated example shown in FIGS. 4A-4B, the projection head portion 264 has a projection head portion transverse dimension 265*a* that is uniform along the length over which the leaflet aperture 308 may be disposed. In some embodiments, subsequent to disposing the leaflet aperture 308 over the projection head portion 264, the projection head portion 264 may be deformed in a manner that operates to retain the leaflet 310 to the leaflet retention surface 233, as shown in FIG. 4B. As shown, the projection head portion 264 includes a projection head portion transverse dimension 265*a* that is larger than a dimension of the leaflet aperture 308.

Figure 5A:
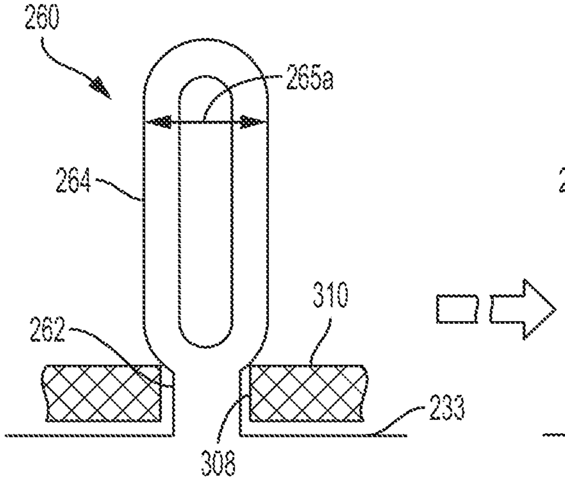
FIGS. 5A and 5B are side views of a leaflet frame projection, according to some embodiments.
Figure 5B:
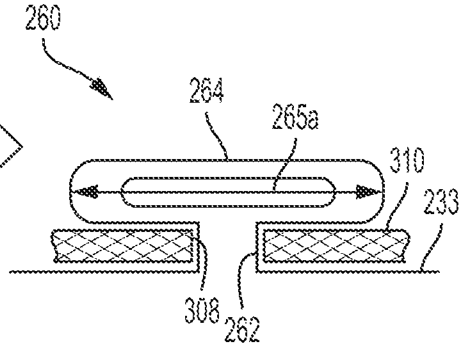

Similarly, in the embodiment of FIGS. 5A-5B, the projection head portion 264 has a shape of an "O" having a largest projection head portion transverse dimension 265*a* that is the same or slightly larger than a dimension of the leaflet aperture 308, as shown in FIG. 5A, over which the leaflet aperture 308 may be disposed. In some embodiments, subsequent to disposing the leaflet aperture 308 over the projection head portion 264, the projection head portion 264 may be deformed in a manner that operates to retain the leaflet 310 to the leaflet retention surface 233, as shown in FIG. 5B. As shown, the projection head portion 264 includes a projection head portion transverse dimension 265*a* that is larger than a dimension of the leaflet aperture 308.

Figure 6A:
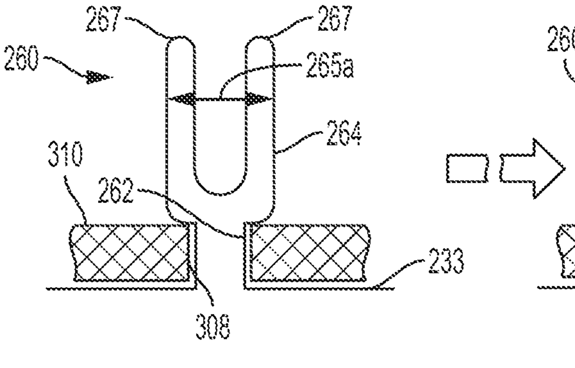
FIGS. 6A and 6B are side views of a leaflet frame projection, according to some embodiments.
Figure 6B:
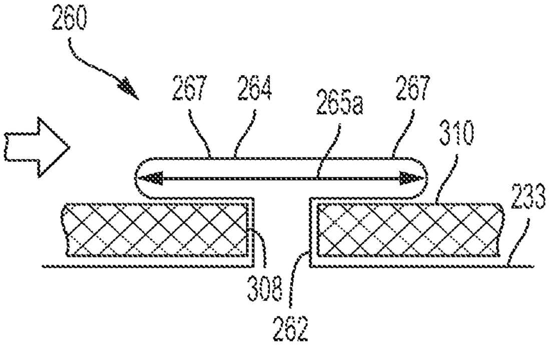

Similarly, in the embodiment of FIGS. 6A-6B, the projection head portion 264 has a shape of two prongs 267 having a largest projection head portion transverse dimension 265*a* that is the same or slightly larger than a dimension of the leaflet aperture 308, as shown in FIG. 6A, over which the leaflet aperture 308 may be disposed. In some embodiments, subsequent to disposing the leaflet aperture 308 over the projection head portion 264, the two prongs 267 may be deformed away from each other and down toward the leaflet retention surface 233 to help facilitate retention of the leaflet 310 on the leaflet retention surface 233, as shown in FIG. 6B. As shown, the projection head portion 264 includes a projection head portion transverse dimension 265*a* that is larger than a dimension of the leaflet aperture 308.

In the embodiments of FIGS. 4A-6B, the projection head portion 264 may be deformed in a number of ways. In some embodiments, the projection head portion 264 may be plastically deformed using mechanical means, such as, but not limited to, crimping. In other embodiments, the projection head portion 264 may additionally or alternatively comprise a shape memory material that may be deformed when exposed to an elevated temperature.

It will be appreciated that other restraining elements can be used to impede leaflet decoupling from the leaflet frame projections 260, such as by impeding leaflet uplift away from the leaflet retention surface and that the examples illustrated and described herein should not be construed as limiting.

While the illustrated embodiments show leaflet windows in the shape of an isosceles trapezoid, it is understood that elements or components of the leaflet frame 200 defining the leaflet windows can be configured to define other leaflet window shapes. In particular, in some embodiments, the two leaflet window sides and a leaflet window base therebetween can together define a parabolic curve. Also, while the illustrated embodiments show commissure posts that are equally spaced around the leaflet frame, it is understood that the commissure posts can be unequally spaced. Similarly, while the illustrated embodiments include three leaflets, it is understood that prosthetic valves and valved conduits of the present disclosure may include more or less than three leaflets, such as 2, 4, or 5 leaflets.

Figure 2F:
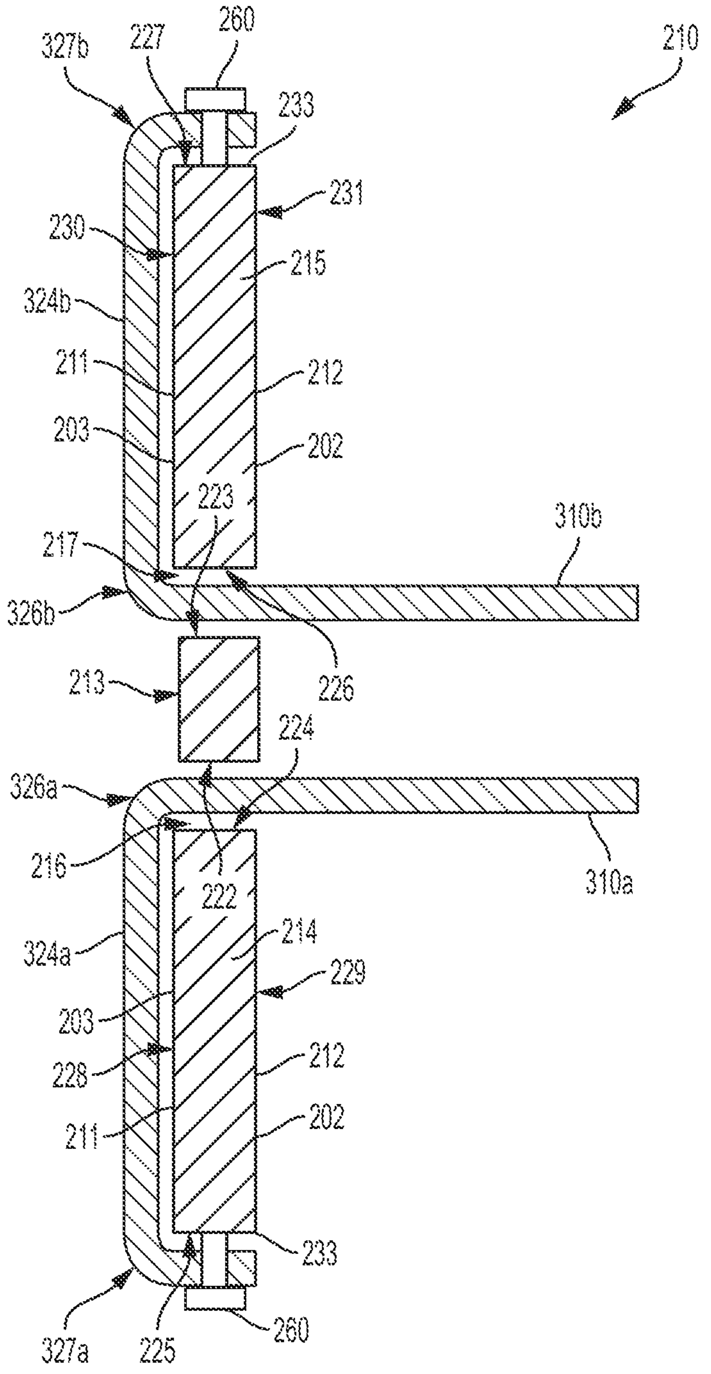
FIG. 2F is a cross-sectional view of FIG. 2D, along line 2F, of the commissure post showing a fold-over portion of the leaflet.

As described later in reference to FIGS. 7A and 7B, a leaflet attachment region 330 of each leaflet 310 is the portion extending through one of the first and second slots 216 and 217 of the commissure posts 210, and secured to the leaflet frame projections 260 along the various portions of the leaflet frame 200 (e.g., the first and second tines 214 and 216 of the commissure posts 210, and/or the commissure post supports 208, and/or the leaflet window base 207). As mentioned above, the fold-over portion 324 of the leaflet base 325 wraps or is otherwise wound around one or more portions (e.g., one or more edges and/or one or more surfaces) of a respective tine of the commissure posts 210. FIG. 2F is a cross-sectional view of FIG. 2E, along line 2F, of the commissure post 210 showing first and second fold-over portions 324*a* and 324*b* of first and second leaflets 310*a* and 310*b*, respectively, wrapped around portions of respective tines 214 and 215. As shown in FIG. 2F, in some embodiments, the first and second fold-over portions 324*a* and 324*b* of the first and second leaflets 310*a* and 310*b* are wrapped around the respective tines 214 and 215 such that the less than all of the surfaces and edges of the respective tines 214 and 215 are covered by the fold-over portions 324. In this example, the fold-over portions 324*a* and 324*b* of the first and second leaflets 310*a* and 310*b* are wrapped at least partially around the respective tines 214 and 215 of the commissure post 210. However, as discussed in greater detail below, in various other embodiments, the fold-over portion 324 of one or more of the leaflets 310 may be wrapped around a respective tine such that all of the surfaces and edges of the respective tine are covered by the fold-over portion 324.

With continued reference to FIG. 2F, the first tine 214 includes a first interior edge 224, a first exterior surface 228, a first exterior edge 225, and a first interior surface 229. In various embodiments, the first exterior surface 228 extends between and is adjacent to the first interior edge 224 and the first exterior edge 225. In various embodiments, the first interior surface 229 also extends between and is adjacent to the first interior edge 224 and the first exterior edge 225. Thus, in various embodiments, each of the first interior and exterior edges 224 and 225 extend between and are adjacent to each of the first exterior and interior surfaces 228 and 229. As shown, the first interior edge 224 and the first exterior surface 228 intersect one another at a first corner. Similarly, as shown, the first exterior surface 228 and the first exterior edge 225 intersect one another at a second corner. Similarly, as shown, the first exterior edge 225 and the first interior surface 229 intersect one another at a third corner. Similarly, as shown, the first interior surface 229 and the first interior edge 224 intersect one another at a fourth corner. In some examples, the first interior edge 224, the first exterior surface 228, the first exterior edge 225, and the first interior surface 229, define, at least in part, the first tine 214.

As shown in FIG. 2F, the second tine 215 includes a second interior edge 226, a second exterior surface 230, a second exterior edge 227, and a second interior surface 231. In various embodiments, the second exterior surface 230 extends between and is adjacent to the second interior edge 226 and the second exterior edge 227. In various embodiments, the second interior surface 231 also extends between and is adjacent to the second interior edge 226 and the second exterior edge 227. Thus, in various embodiments, each of the second interior and exterior edges 226 and 227 extend between and are adjacent to the second exterior and interior surfaces 230 and 231. As shown, the second interior edge 226 and the second exterior surface 230 intersect one another at a first corner. Similarly, as shown, the second exterior surface 230 and the second exterior edge 227 intersect one another at a second corner. Similarly, as shown, the second exterior edge 227 and the second interior surface 231 intersect one another at a third corner. Similarly, as shown, the second interior surface 231 and the second interior edge 226 intersect one another at a fourth corner. In some examples, the second interior edge 226, the second exterior surface 230, the second exterior edge 227, and the second interior surface 231, define, at least in part, the second tine 215.

As shown in FIG. 2F, the fold-over portion 324*a* of the first leaflet 310*a* extends through the first slot 216 between the first edge 222 of the spine 213 and the first interior edge 224 of the first tine 214. As shown, the fold-over portion 324*a* of the first leaflet 310*a* includes a first fold 326*a* such that the fold-over portion 324*a* of the first leaflet 310*a* extends along a first exterior surface 228 of the first tine 214. In some embodiments, the first fold is adjacent the first corner. As shown, the fold-over portion 324*a* of the first leaflet 310*a* includes a second fold 327*a* such that the fold-over portion 324*a* of the first leaflet 310*a* extends along the first exterior edge 225 of the first tine 214. In some embodiments, the second fold is adjacent the second corner. As shown, the fold-over portion 324*a* of the first leaflet 310*a* is disposed over a leaflet frame projection 260 extending from the first exterior edge 225 of the first tine 214. As shown, in this embodiment, the fold-over portion 324*a* of the first leaflet 310*a* does not extend along a first interior surface 229 of the first tine 214. It will be appreciated that while the fold-over portion 324*a* of the first leaflet 310*a* is shown in FIG. 2F as including a gap between the first interior surface 224 and the respective the fold-over portion 324*a* extending therealong, the first exterior surface 228 and the respective the fold-over portion 324*a* extending therealong, and the first exterior edge 225 and the respective the fold-over portion 324*b* extending therealong, the fold-over portion 324*a* may contact one or more of the first interior surface 224, the first exterior surface 228, and the first exterior edge 225.

Similarly, and with continued reference to FIG. 2F, the fold-over portion 324*b* of the second leaflet 310*b* extends through the second slot 217 between the second edge 223 of the spine 213 and the second interior edge 226 of the second tine 215. As shown, the fold-over portion 324*b* of the second leaflet 310*b* includes a first fold 326*b* such that the fold-over portion 324*b* of the second leaflet 310*b* extends along a second exterior surface 230 of the second tine 215. In some embodiments, the first fold is adjacent the first corner. As shown, the fold-over portion 324*b* of the second leaflet 310*b* includes a second fold 327*b* such that the fold-over portion 324*b* of the second leaflet 310*b* extends along the second exterior edge 227 of the second tine 215. In some embodiments, the first fold is adjacent the second corner. As shown, the fold-over portion 324*b* of the second leaflet 310*b* is disposed over a leaflet frame projection 260 extending from the second exterior edge 227 of the second tine 215. As shown, in this embodiment, the fold-over portion 324*b* of the second leaflet 310*b* does not extend along a second interior surface 231 of the second tine 215. It will be appreciated that while the fold-over portion 324*b* of the second leaflet 310*b* is shown in FIG. 2F as including a gap between the second interior edge 226 and the respective the fold-over portion 324*b* extending therealong, the second exterior surface 230 and the respective the fold-over portion 324*b* extending therealong, and the second exterior edge 227 and the respective the fold-over portion 324*b* extending therealong, the fold-over portion 324*b* may contact one or more of the second interior edge 226, the second exterior surface 230, and the second exterior edge 227.

Figure 2G:
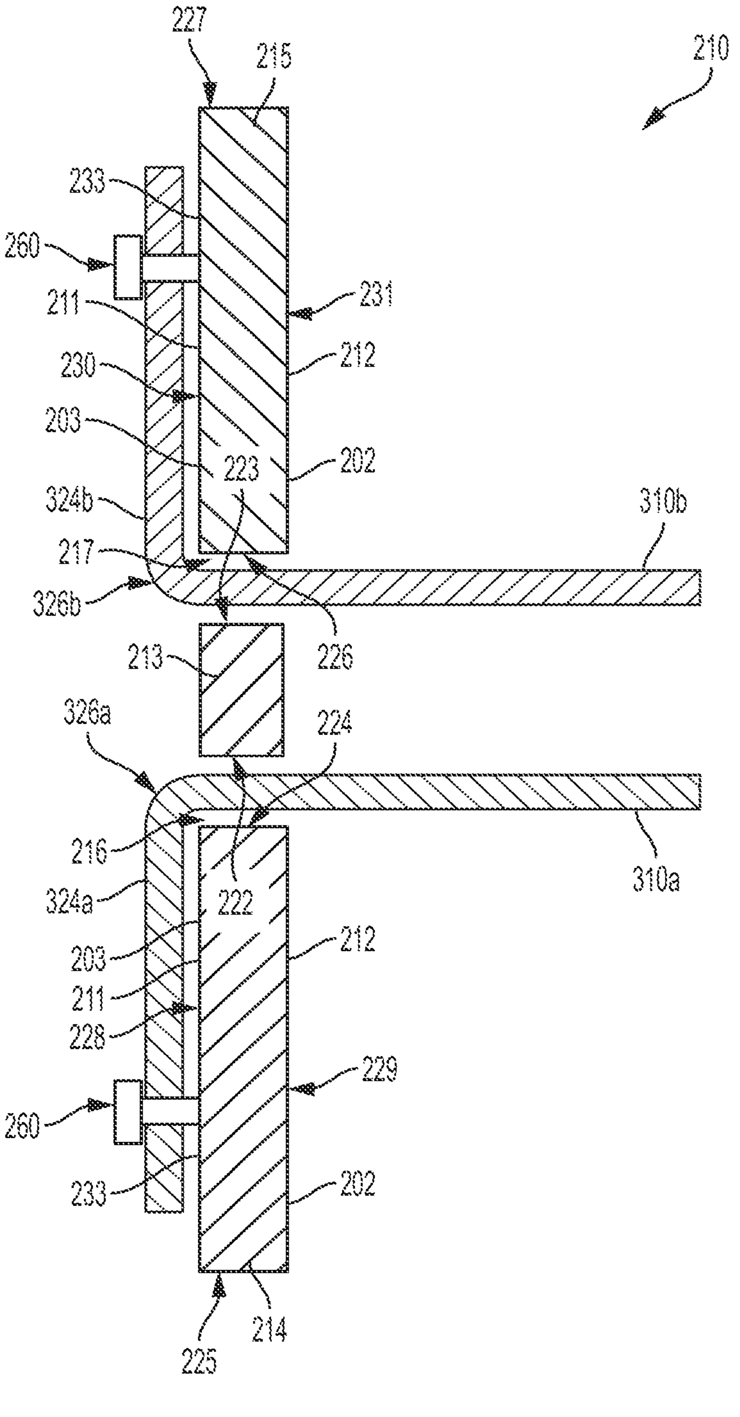
FIG. 2G is a cross-sectional view of a commissure post showing a fold-over portion of the leaflet, according to another embodiment.

FIG. 2G is a cross-sectional view of a commissure post 210, according to another embodiment. FIG. 2G shows first and second fold-over portions 324*a* and 324*b* of first and second leaflets 310*a* and 310*b*, respectively, wrapped around portions of respective tines 214 and 215. As shown in FIG. 2G, in some embodiments, the first and second fold-over portions 324*a* and 324*b* of the first and second leaflets 310*a* and 310*b* are wrapped around the respective tines 214 and 215 such that the less than all of the surfaces and edges of the respective tines 214 and 215 are covered by the fold-over portions 324. In this example, the fold-over portions 324*a* and 324*b* of the first and second leaflets 310*a* and 310*b* are wrapped at least partially around the respective tines 214 and 215 of the commissure post 210.

With continued reference to FIG. 2G, the fold-over portion 324*a* of the first leaflet 310*a* extends through the first slot 216 between the first edge 222 of the spine 213 and the first interior edge 224 of the first tine 214. As shown, the fold-over portion 324*a* of the first leaflet 310*a* includes a first fold 326*a* such that the fold-over portion 324*a* of the first leaflet 310*a* extends along the first exterior surface 228 of the first tine 214. As shown, the fold-over portion 324*a* of the first leaflet 310*a* is disposed over a leaflet frame projection 260 extending from the first exterior surface 228 of the first tine 214. As shown, in this embodiment, the fold-over portion 324*a* of the first leaflet 310*a* does not extend along the first exterior edge 225 or the first interior surface 229 of the first tine 214 (see FIG. 2H). It will be appreciated that while the fold-over portion 324*a* of the first leaflet 310*a* is shown in FIG. 2G as including a gap between the first interior surface 224 and the respective the fold-over portion 324*a* extending therealong, and the first exterior surface 228 and the respective the fold-over portion 324*a* extending therealong, the fold-over portion 324*a* may contact one or more of the first interior surface 224 and the first exterior surface 228.

Similarly, and with continued reference to FIG. 2G, the fold-over portion 324*b* of the second leaflet 310*b* extends through the second slot 217 between the second edge 223 of the spine 213 and the second interior edge 226 of the second tine 215. As shown, the fold-over portion 324*b* of the second leaflet 310*b* includes a first fold 326*b* such that the fold-over portion 324*b* of the second leaflet 310*b* extends along the second exterior surface 230 of the second tine 215. As shown, the fold-over portion 324*b* of the second leaflet 310*b* is disposed over a leaflet frame projection 260 extending from the second exterior surface 230 of the second tine 215. As shown, in this embodiment, the fold-over portion 324*b* of the second leaflet 310*b* does not extend along the second exterior edge 227 or the second interior surface 231 of the second tine 215. It will be appreciated that while the fold-over portion 324*b* of the second leaflet 310*b* is shown in FIG. 2G as including a gap between the second interior edge 226 and the respective the fold-over portion 324*b* extending therealong, and the second exterior surface 230 and the respective the fold-over portion 324*b* extending therealong, the fold-over portion 324*b* may contact one or more of the second interior edge 226 and the second exterior surface 230.

Figure 2H:
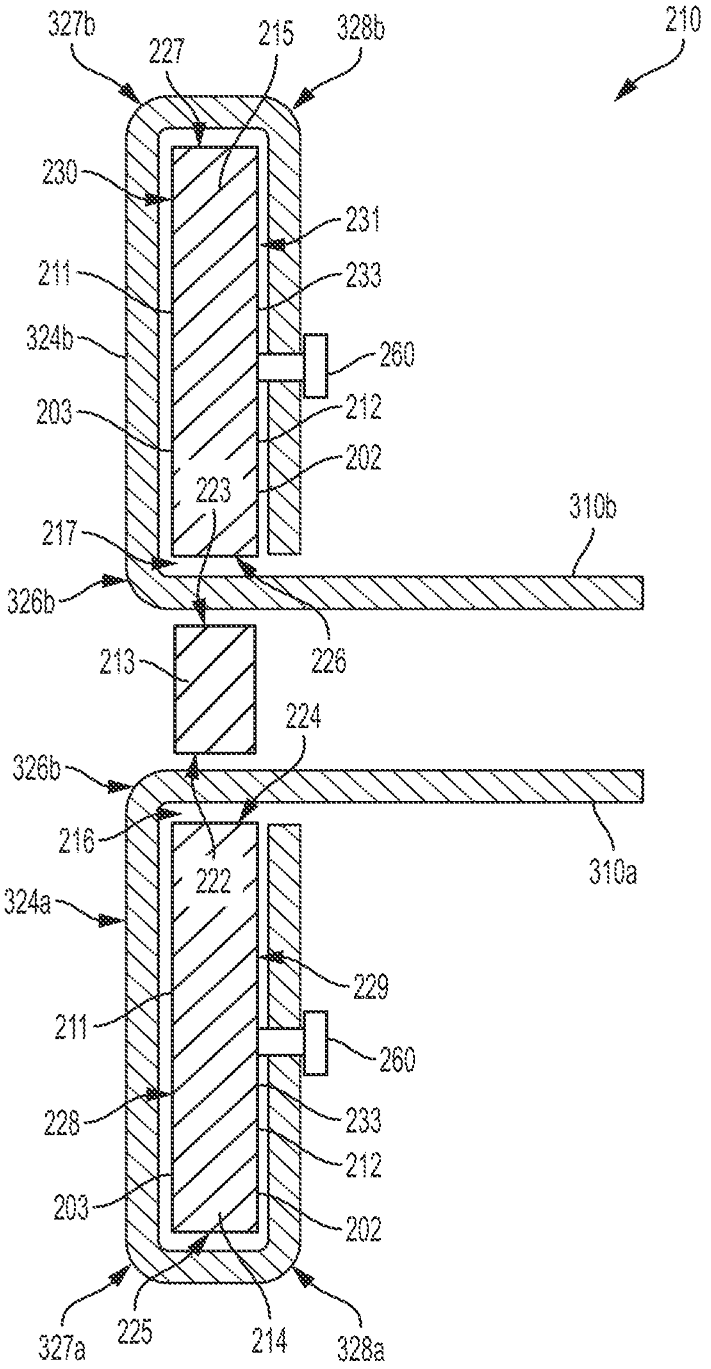
FIG. 2H is a cross-sectional view of a commissure post showing a fold-over portion of the leaflet, according to another embodiment.

FIG. 2H is a cross-sectional view of a commissure post 210, according to another embodiment. FIG. 2H shows first and second fold-over portions 324*a* and 324*b* of first and second leaflets 310*a* and 310*b*, respectively, wrapped around portions of respective tines 214 and 215. As shown in FIG. 2H, in some embodiments, the first and second fold-over portions 324*a* and 324*b* of the first and second leaflets 310*a* and 310*b* are wrapped around the respective tines 214 and 215 such that the fold-over portions 324*a* and 324*b* extend along each of the surfaces and edges of the respective tines 214 and 215. In this example, the fold-over portions 324*a* and 324*b* of the first and second leaflets 310*a* and 310*b* are wrapped at least partially around the respective tines 214 and 215 of the commissure post 210.

With continued reference to FIG. 2H, the fold-over portion 324*a* of the first leaflet 310*a* extends through the first slot 216 between the first edge 222 of the spine 213 and the first interior edge 224 of the first tine 214. As shown, the fold-over portion 324*a* of the first leaflet 310*a* includes a first fold 326*a* such that the fold-over portion 324*a* of the first leaflet 310*a* extends along a first exterior surface 228 of the first tine 214. As shown, the fold-over portion 324*a* of the first leaflet 310*a* includes a second fold 327*a* such that the fold-over portion 324*a* of the first leaflet 310*a* extends along the first exterior edge 225 of the first tine 214. As shown, the fold-over portion 324*a* of the first leaflet 310*a* includes a third fold 328*a* such that the fold-over portion 324*a* of the first leaflet 310*a* extends along the first interior surface 229 of the first tine 214. In some embodiments, the third fold is adjacent the third corner. As shown, the fold-over portion 324*a* of the first leaflet 310*a* is disposed over a leaflet frame projection 260 extending from the first interior surface 229 of the first tine 214. It will be appreciated that while the fold-over portion 324*a* of the first leaflet 310*a* is shown in FIG. 2H as including a gap between the first interior surface 224 and the respective the fold-over portion 324*a* extending therealong, the first exterior surface 228 and the respective the fold-over portion 324*a* extending therealong, the first exterior edge 225 and the respective the fold-over portion 324*b* extending therealong, and the first interior surface 229 and the respective the fold-over portion 324*b* extending therealong, the fold-over portion 324*a* may contact one or more of the first interior surface 224, the first exterior surface 228, the first exterior edge 225, and the first interior surface 229.

Similarly, and with continued reference to FIG. 2H, the fold-over portion 324*b* of the second leaflet 310*b* extends through the second slot 217 between the second edge 223 of the spine 213 and the second interior edge 226 of the second tine 215. As shown, the fold-over portion 324*b* of the second leaflet 310*b* includes a first fold 326*b* such that the fold-over portion 324*b* of the second leaflet 310*b* extends along a second exterior surface 230 of the second tine 215. As shown, the fold-over portion 324*b* of the second leaflet 310*b* includes a second fold 327*b* such that the fold-over portion 324*b* of the second leaflet 310*b* extends along the second exterior edge 227 of the second tine 215. As shown, the fold-over portion 324*b* of the second leaflet 310*b* includes a third fold 328*b* such that the fold-over portion 324*b* of the second leaflet 310*b* extends along the second interior surface 231 of the second tine 215. In some embodiments, the third fold is adjacent the third corner. As shown, the fold-over portion 324*b* of the second leaflet 310*b* is disposed over a leaflet frame projection 260 extending from the second interior surface 231 of the second tine 215. It will be appreciated that while the fold-over portion 324*b* of the second leaflet 310*b* is shown in FIG. 2H as including a gap between the second interior edge 226 and the respective the fold-over portion 324*b* extending therealong, the second exterior surface 230 and the respective the fold-over portion 324*b* extending therealong, the second exterior edge 227 and the respective the fold-over portion 324*b* extending therealong, the second interior surface 231 and the respective the fold-over portion 324*b* extending therealong, the fold-over portion 324*b* may contact one or more of the second interior edge 226, the second exterior surface 230, the second exterior edge 227, and the second interior surface 231.

Figure 2I:
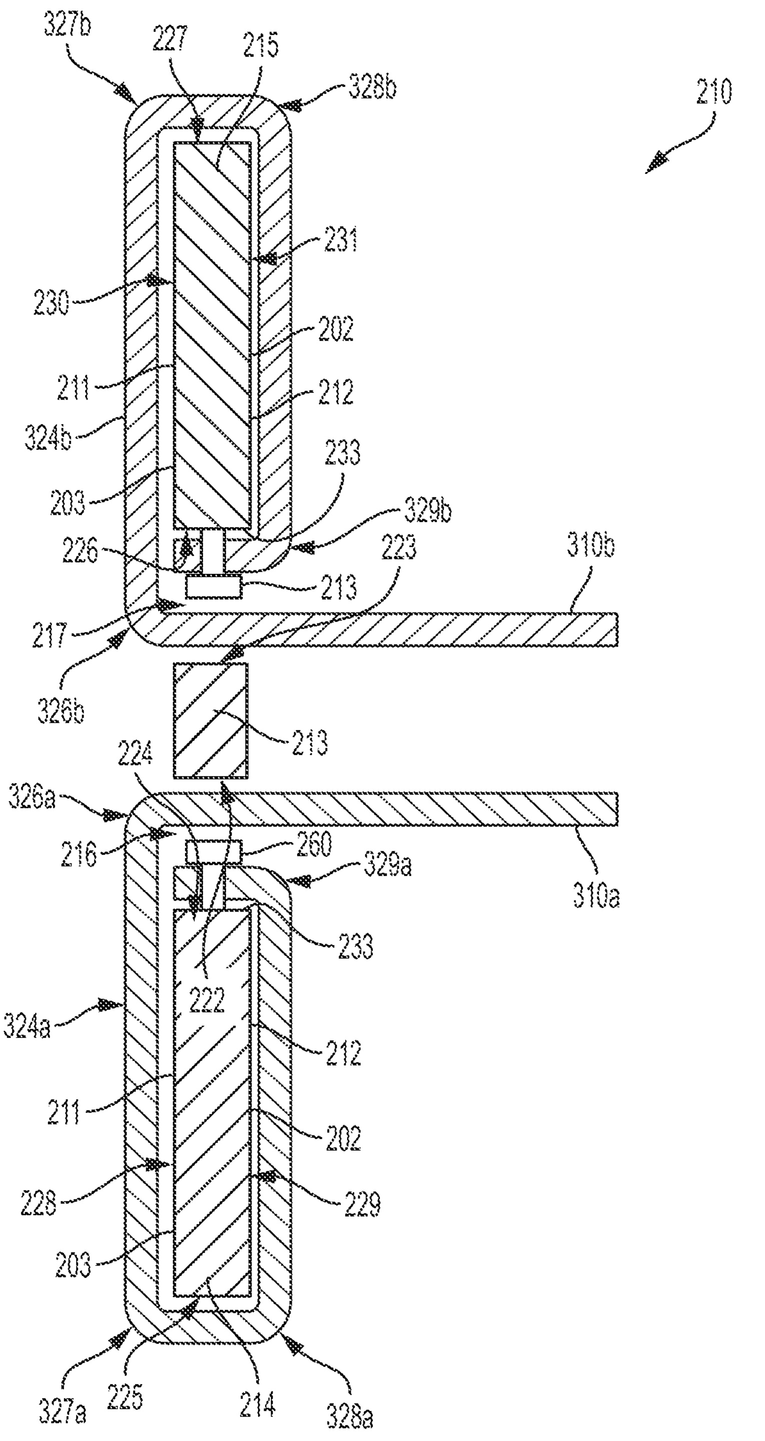
FIG. 2I is a cross-sectional view of a commissure post showing a fold-over portion of the leaflet, according to another embodiment.

FIG. 2I is a cross-sectional view of a commissure post 210, according to another embodiment. FIG. 2I shows first and second fold-over portions 324*a* and 324*b* of first and second leaflets 310*a* and 310*b*, respectively, wrapped around the respective tines 214 and 215. As shown in FIG. 2I, in some embodiments, the first and second fold-over portions 324*a* and 324*b* of the first and second leaflets 310*a* and 310*b* are wrapped around the respective tines 214 and 215 such that the surfaces and edges of the respective tines 214 and 215 are completely covered by the fold-over portions 324. Thus, in this example, the fold-over portions 324*a* and 324*b* of the first and second leaflets 310*a* and 310*b* are wrapped completely around the respective tines 214 and 215 of the commissure post 210.

With continued reference to FIG. 2I, the fold-over portion 324*a* of the first leaflet 310*a* extends through the first slot 216 between the first edge 222 of the spine 213 and the first interior edge 224 of the first tine 214. As shown, the fold-over portion 324*a* of the first leaflet 310*a* includes a first fold 326*a* such that the fold-over portion 324*a* of the first leaflet 310*a* extends along a first exterior surface 228 of the first tine 214. As shown, the fold-over portion 324*a* of the first leaflet 310*a* includes a second fold 327*a* such that the fold-over portion 324*a* of the first leaflet 310*a* extends along the first exterior edge 225 of the first tine 214. As shown, the fold-over portion 324*a* of the first leaflet 310*a* includes a third fold 328*a* such that the fold-over portion 324*a* of the first leaflet 310*a* extends along the first interior surface 229 of the first tine 214. As shown, the fold-over portion 324*a* of the first leaflet 310*a* includes a fourth fold 329*a* such that the fold-over portion 324*a* of the first leaflet 310*a* extends along the first interior edge 224 of the first tine 214 a plurality of times. That is, as shown, the fold-over portion 324*a* of the first leaflet 310*a* is wrapped around the first tine 214 such that the fold-over portion 324*a* of the first leaflet 310*a* overlaps itself. In some embodiments, the fourth fold is adjacent the fourth corner. As shown, the fold-over portion 324*a* of the first leaflet 310*a* is disposed over a leaflet frame projection 260 extending from the first interior edge 224 of the first tine 214. It will be appreciated that while the fold-over portion 324*a* of the first leaflet 310*a* is shown in FIG. 2I as including a gap between the first interior surface 224 and the respective the fold-over portion 324*a* extending therealong, the first exterior surface 228 and the respective the fold-over portion 324*a* extending therealong, the first exterior edge 225 and the respective the fold-over portion 324*b* extending therealong, and the first interior surface 229 and the respective the fold-over portion 324*b* extending therealong, the fold-over portion 324*a* may contact one or more of the first interior surface 224, the first exterior surface 228, the first exterior edge 225, and the first interior surface 229.

Similarly, and with continued reference to FIG. 2I, the fold-over portion 324*b* of the second leaflet 310*b* extends through the second slot 217 between the second edge 223 of the spine 213 and the second interior edge 226 of the second tine 215. As shown, the fold-over portion 324*b* of the second leaflet 310*b* includes a first fold 326*b* such that the fold-over portion 324*b* of the second leaflet 310*b* extends along a second exterior surface 230 of the second tine 215. As shown, the fold-over portion 324b of the second leaflet 310b includes a second fold 327b such that the fold-over portion 324b of the second leaflet 310b extends along the second exterior edge 227 of the second tine 215. As shown, the fold-over portion 324b of the second leaflet 310b includes a third fold 328b such that the fold-over portion 324b of the second leaflet 310b extends along the second interior surface 231 of the second tine 215. As shown, the fold-over portion 324b of the second leaflet 310b includes a fourth fold 329b such that the fold-over portion 324b of the second leaflet 310b extends along the second interior edge 226 of the second tine 215 a plurality of times. That is, as shown, the fold-over portion 324b of the second leaflet 310b is wrapped around the second tine 215 such that the fold-over portion 324b of the second leaflet 310b overlaps itself. In some embodiments, the fourth fold is adjacent the fourth corner. As shown, the fold-over portion 324b of the second leaflet 310b is disposed over a leaflet frame projection 260 extending from the second interior surface 231 of the second tine 215. It will be appreciated that while the fold-over portion 324b of the second leaflet 310b is shown in FIG. 2H as including a gap between the second interior edge 226 and the respective the fold-over portion 324b extending therealong, the second exterior surface 230 and the respective the fold-over portion 324b extending therealong, the second exterior edge 227 and the respective the fold-over portion 324b extending therealong, the second interior surface 231 and the respective the fold-over portion 324b extending therealong, the fold-over portion 324b may contact one or more of the second interior edge 226, the second exterior surface 230, the second exterior edge 227, and the second interior surface 231.

The various wrapping schemes illustrated and described above with regard to FIGS. 2F-2I should not be construed as limiting. That is, it should be understood that various alternative wrapping schemes are envisioned and fall within the scope of the present disclosure. It should also be appreciated that while the tines illustrated and described herein are polygonal, one or more of the tines may be cylindrical. That is, in some embodiments, one or more of the tines includes a continuous exterior surface. In some embodiments, similar to the embodiments and examples illustrated and described herein, one or more leaflet frame projections extend from the continuous exterior surface. Accordingly, in various examples, in a manner similar to embodiments and examples illustrated and described herein, the leaflet 310 may be wrapped (partially or completely) about one or more tines having a continuous exterior surface.

It will also be appreciated that one or more of the various wrapping schemes illustrated and described above with regard to FIGS. 2F-2I can be utilized to secure, attach, or otherwise couple leaflets 310 to a leaflet frame 200. For example, a first leaflet can be coupled to a leaflet frame 200 in accordance with the wrapping scheme illustrated and described above in FIG. 2F, while a second leaflet can be coupled to a leaflet frame 200 in accordance with the wrapping scheme illustrated and described above in FIG. 2I. Similarly, for a given leaflet 310, the leaflet 310 may be coupled to a first commissure post 210 in accordance with a first one of the wrapping schemes illustrated and described above (e.g., FIG. 2G), and coupled to a second commissure post 210 leaflet frame 200 in accordance with a first one of the wrapping schemes illustrated and described above (e.g., FIG. 2H).

Generally, the leaflets 310 extend radially inward from the leaflet frame 200 when coupled to the leaflet frame 200. As mentioned above, the leaflet 310 is configured to couple to the leaflet frame 200 by way of a plurality of leaflet apertures 308 located in the leaflet attachment region 330 of the leaflet 310 that are complementary in shape, size, and/or pattern to the corresponding leaflet frame projections 260 of the leaflet frame 200.

In various embodiments, each leaflet 310 defines a leaflet attachment region 330, a leaflet belly region 322, and a leaflet free edge 312; the leaflet belly region 322 terminates at the leaflet free edge 312. A leaflet base 325 generally refers to the intersection between the leaflet attachment region 330 and the leaflet belly region 322. The leaflet belly region 322 of each leaflet 310 is the operating portion of the leaflet 310 when assembled into a finished prosthetic valve 100. The leaflet attachment region 330 of each leaflet 310 is the portion that is used to secure the leaflet 310 to the leaflet frame 200.

In accordance with various embodiments, the leaflet attachment region 330 is couplable to the leaflet frame 200 at the commissure post 210, the commissure post support 208, and the leaflet window base 207. More particularly, the leaflet attachment region 330 defines a plurality of leaflet apertures 308 that are configured to each receive a leaflet frame projection 260, like the illustrated example shown in FIG. 1A. As previously described, in various embodiments, the shape and dimensions of the leaflet aperture 308 can be substantially the same as the shape and dimensions of the projection base portion 262 of the leaflet frame projection 260.

In some embodiments, the leaflet 310 is reinforced about one or more leaflet apertures 308. A reinforcement can be, for example, a leaflet attachment region 330 comprising a thickened portion of leaflet material that defines the leaflet aperture 308. In some embodiments, the reinforcement can be a reinforcement strip 332 that is added to the leaflet 310 in the leaflet attachment region 330 and defines the leaflet apertures 308. In some embodiments, the reinforcement can be a folded over portion to provide a double or triple, or more, layers of leaflet material and defines the leaflet apertures 308. In some embodiments, the reinforcement strip 332 can comprise leaflet material that is the same material as the leaflet 310. In various embodiments, when coupled to the leaflet frame 200, the reinforcement strip 332 can be located on a leaflet first side 311 of the leaflet 310, which faces the leaflet retention surface 233 of the leaflet frame 200. Alternatively the reinforcement strip 332 can be on a leaflet second side 313 that is opposite from the leaflet first side 311. Alternatively, the reinforcement strip 332 can be on both the leaflet first side 311 and the leaflet second side 313.

In various embodiments, when the leaflets 310 are in a fully open position, the prosthetic valve 100 presents a valve orifice 101 that is substantially circular, and fluid flow is permitted through the valve orifice 101 when the leaflets 310 are in the open position. In some embodiments, in the open position, each leaflet 310 is extended from the leaflet frame inner surface 202 at an angle of greater than 45 degrees.

Figure 1D:
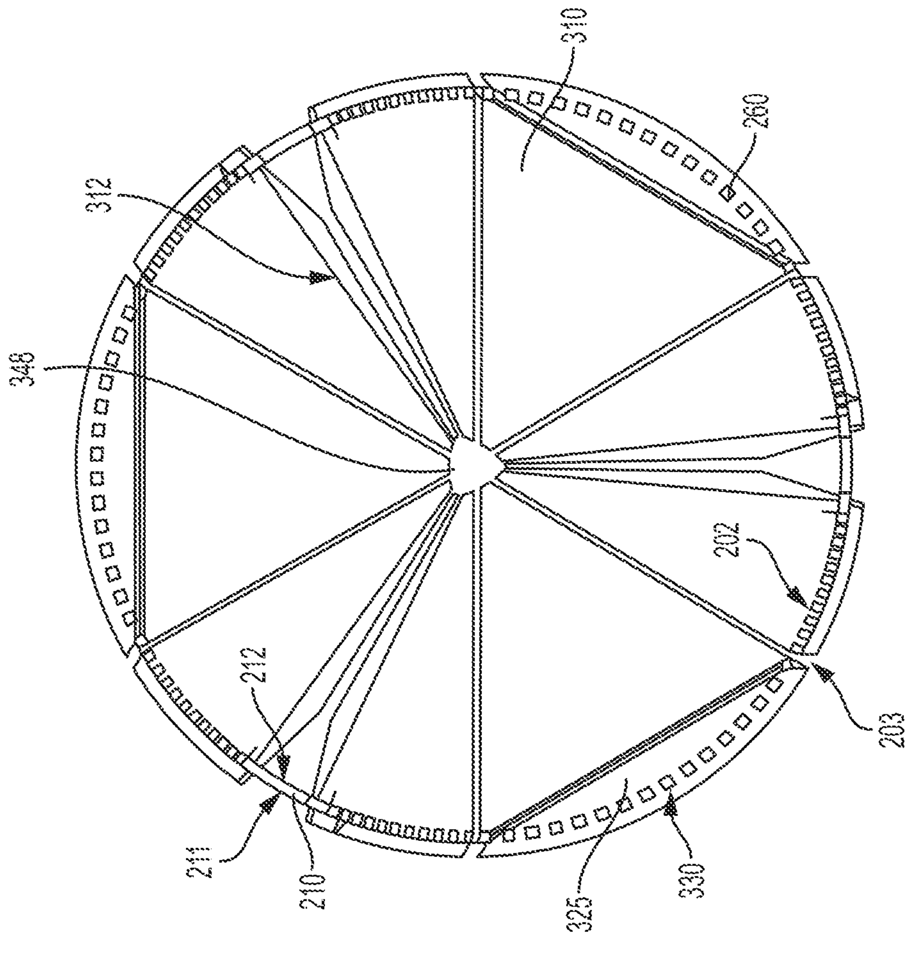
FIG. 1D is a top view of the prosthetic valve embodiment of FIG. 1A.

In various embodiments, when the prosthetic valve 100 is closed, generally about half of each leaflet free edge 312 abuts an adjacent half of a leaflet free edge 312 of an adjacently situated leaflet 310, as shown in FIG. 1D for example. In some embodiments, the leaflets 310 of the prosthetic valve converge at a central point. For example, as shown in FIGS. 1A and 1D, the leaflets 310 meet or nearly meet at a triple point 348. The valve orifice 101 is generally occluded when the leaflets 310 are in the closed position stopping or significantly reducing fluid flow through the valve orifice 101. In some embodiments, in the closed position, each leaflet 310 is extended substantially perpendicular from the leaflet frame inner surface 202. In some embodiments, the leaflets 310 exhibit a bias toward the closed position by virtue of the leaflet 310 extending from the leaflet frame inner surface 202 substantially normal to the central longitudinal axis A-B of the leaflet frame 200 which defines the central longitudinal axis of the prosthetic valve 100. It will be appreciated that such a configuration is beneficial in that the leaflets 310 will tend to close earlier during the phase of the cardiac cycle where the blood is decelerating or reversing. Such a configuration will generally tend to reduce back flow through the prosthetic valve 100.

The shape of each leaflet 310 when coupled to the leaflet frame 200 is determined in part by the shape of the leaflet retention surface of the leaflet frame elements defining the leaflet window 204, and the particular attachment method (e.g., wrapping about one or more portions of the leaflet frame 200 before engaging the leaflet apertures 308 with the leaflet frame projections 260), as well as the shape of the leaflet attachment region 330 and the leaflet free edge 312.

FIG. 7A shows a top view of the leaflet 310, as used in the prosthetic valve 100 of FIG. 1A, in a flat configuration. This view shows that the leaflet 310 has substantially the shape of an isosceles trapezoid with bowed sides at the leaflet attachment region 330. In some embodiments, the degree of bowing corresponds to the arc of the leaflet frame 200 at the two commissure post supports 208 and the leaflet window base 207, respectively. FIG. 7A also illustrates an exemplary configuration where the leaflet free edge 312 includes a scallop-like shape with an apex at the center flanked on each side by a generally concave edge that is straight near the apex. By modifying the geometries and dimensions of this flat pattern, three-dimensional shape of a leaflet 310 can be altered. Of course, while not necessarily required, the shape of the leaflets 310 can also be influenced by other techniques, such as, but not limited to, leaflet molding and shape-setting.

In various embodiments, the leaflet 310 includes a fold-over portion 324 that is adjacent to the leaflet base 325. In some embodiments, the fold-over portion 324 includes the reinforcement strip 332. In various embodiments, the leaflet 310 is configured to wrap around a portion of one or more elements or components of the leaflet frame 200. For example, as mentioned above, each commissure post 210 includes a first and second tine 214 and 215 and the fold-over portion 324 of the leaflet 310 is configuration to wrap around or otherwise "fold-over" at least a portion of either of the first and second tine 214 and 215 of the commissure post 210.

In various embodiments, to facilitate wrapping around the respective leaflet frame elements (e.g., the tines of the commissure posts 210), the leaflet attachment region 330 can define one or more notches 323. A notch 323 can be located on the leaflet 310 such that when coupled to the leaflet frame 200, the notch 323 is at an intersection, joint, or other position between two leaflet frame elements (e.g., a position between the end of a tine and a commissure post support side). In some embodiments, as discussed in greater detail below, a notch 323 is located on the leaflet such that when coupled to the leaflet frame 200, the notch 323 is situated between adjacent discontinuous receiving slots (e.g., side, base, or commissure receiving slots) along the leaflet frame 200.

When coupled to the leaflet frame 200 of FIG. 2A-2F, the first and second slots 216 and 217 of the commissure post 210 each receive respective portions of the leaflet attachment region 330. In some embodiments, the fold-over portion 324 of a leaflet 310 is disposed within the first slot 216 and wrapped around the first tine 214 from the post inner side 212 to the post outer side 211 of the commissure post 210, as shown in FIG. 2F. As further illustrated in FIG. 2F, the leaflet attachment region 330 that includes the leaflet apertures 308 is seated on the first exterior edge 225 of the first tine 214 such that each leaflet aperture 308 is disposed about a corresponding leaflet frame projection 260 on the leaflet retention surface 233, in this case, the first exterior edge 225 of the first tine 214. In various embodiments, the fold-over portions 324 of adjacently situated leaflets 310 are separated from one another at the commissure post 210 by the spine 213, as shown in FIG. 2F and as mentioned above. In some embodiments, such a configuration provides that the leaflet free edge 312 immediately adjacent or proximate the post inner side 212 of the commissure post 210 do not coapt or otherwise contact one another (e.g., a slight gap is formed between adjacently situated leaflets 310 immediately adjacent or proximate the post inner side 212 of the commissure post 210). It will be appreciated that the adjacently situated leaflets coapt at a point radially inward of this gap, between the post inner side 212 and the triple point 348. In some embodiments, such a configuration helps minimize thrombus formation at or immediately proximate the post inner side 212 of the commissure post 210. It will be appreciated, however, that alternative configurations provide for fold-over portions 324 of adjacently situated leaflets 310 passing through a single post slot of a commissure post so that the leaflet free edges 312 of the adjacently situated leaflets 310 are operable to coapt or contact one another at or proximate to the post inner side 212 of the commissure post 210. Examples of such configurations are illustrated and described in U.S. Pat. No. 9,855,141 to Dienno referred to above, the entire contents of which are incorporated herein by reference. In various embodiments, in addition to engagement with one or more of the leaflet frame projections 260, the leaflet 310 can be fixed to one or more portions of the leaflet frame 200 such as by way of an adhesive agent, sewing, or some other suitable means, such as via one or more windings about one or more fibers, as discussed further below.

In various embodiments, wrapping the leaflet 310 about one or more portions of the leaflet frame 200 as described herein helps more evenly distribute the load exerted on the leaflets 310 and avoids stress concentrations in critical areas of the leaflet 310 that could lead to a premature failure of the leaflet 310. In some embodiments, force can be more evenly distributed by additionally or alternatively increasing the distance between the leaflet aperture 308 and the leaflet base 325, which is the intersection between the leaflet attachment region 330 and the leaflet belly region 322.

In various embodiments, the leaflet 310 can be made of a polymer (non-biological tissue) or biological tissue, as discussed in greater detail below. For instance, in some embodiments, the leaflet 310 is made from a sheet of polymer material or biological tissue that has been cut into a shape with the leaflet apertures 308 like that shown in FIGS. 7A-7C. In various embodiments, the leaflet 310 can become "shaped" upon attachment to the leaflet frame 200. That is, prior to coupling with the leaflet frame 200, the leaflet 310 is an otherwise flat sheet of material, and upon coupling the leaflet 310 with the leaflet frame 200, the leaflet 310 adopts a contoured or non-flat shape consistent with that illustrated in FIGS. 1A and 1D. In some embodiments, leaflets 310 can be pre-shaped. Pre-shaped polymer leaflets are generally made cutting a cylinder of polymer material into a shape like that shown in FIGS. 7A-7C with the leaflet apertures 308. In some embodiments, a reinforcement strip 332 is bonded or otherwise coupled to the polymer material or biological material. In some embodiments, the leaflet apertures 308 are cut into both the leaflet 310 and reinforcement strip 332. This can occur simultaneously or alternatively prior to mating the leaflet 310 and reinforcement strip 332.

It will be appreciated that while the leaflet 310 is passed through one or more slots and wrapped about one or more portions of the leaflet frame 200 before being disposed about one or more leaflet frame projections 260 on a leaflet retention surface 233, in some embodiments, one or more other portions of the leaflet frame 200 are disposed about one or more leaflet frame projections 260 on a leaflet retention surface 233 without first passing through a slot of the leaflet frame or being wrapped or wound about a portion of the leaflet frame 200. That is, in some embodiments, one or more other portions of the leaflet 310 are disposed about one or more leaflet frame projections 260 without being wrapped or wound (partially or completely) about the leaflet frame 200. For example, as shown in FIG. 1A, those portions of the leaflet 310 coupled to the leaflet frame 200 along the commissure post supports 208 and the leaflet window base 207 do no first pass through a slot or wrap around a portion of the leaflet frame 200. Examples of other configurations where the leaflet 310 is coupled to the leaflet frame 200 without first passing through a slot or wrapping around a portion of the leaflet frame 200 are illustrated and described in U.S. Pat. No. 9,855,141 to Dienno, referred to above.

Additionally, while the examples illustrated and described above include slots that are free of leaflet frame projections, in various embodiments, one or more slots of the leaflet frame may include one or more leaflet frame projections 260. In such embodiments, it will be appreciated that the leaflet 310 is wrapped about a surface of the leaflet frame 200 prior to being inserted into the slot and disposed about the one or more leaflet frame projections 260 included in the one or more slots.

Additionally, while the embodiments illustrated and described above include a commissure post 210 with a plurality of tines having free ends, in various other embodiments, one or more of the tines of the commissure posts are coupled at both ends to the leaflet frame 200. That is, in various embodiments, the leaflet frame 200 includes one or more closed slots. In particular, in various embodiments, one or more of the slots of the commissure post 210 are closed slots in that the tine defining a portion of the closed slot is coupled at each of its ends to the leaflet frame 200. For instance, a first end of the tine is coupled to or extends from the spine 213 of the commissure post (e.g., at or proximate to the commissure tip 221, and a second end of the tine is coupled to or extends from a position below or inferior to the first end. In some embodiments, the second end of the tine is coupled to or extends from a portion of the spine 213 below or inferior to where the first end of the tine couples to or extends from the spine 213. In some other embodiments, the second end of the tine is coupled to or extends from a portion of the leaflet frame below or inferior to the spine 213 (e.g., the commissure post support 208, leaflet window base 207, etc.).

Although relatively sharp corners are shown in the various representative figures of the present disclosure, it should be understood that chamfers, rounds, reliefs, coatings, and other features may be provided to avoid stress concentrations or other wearing of the leaflets or other components interfacing therewith.

Figure 8:
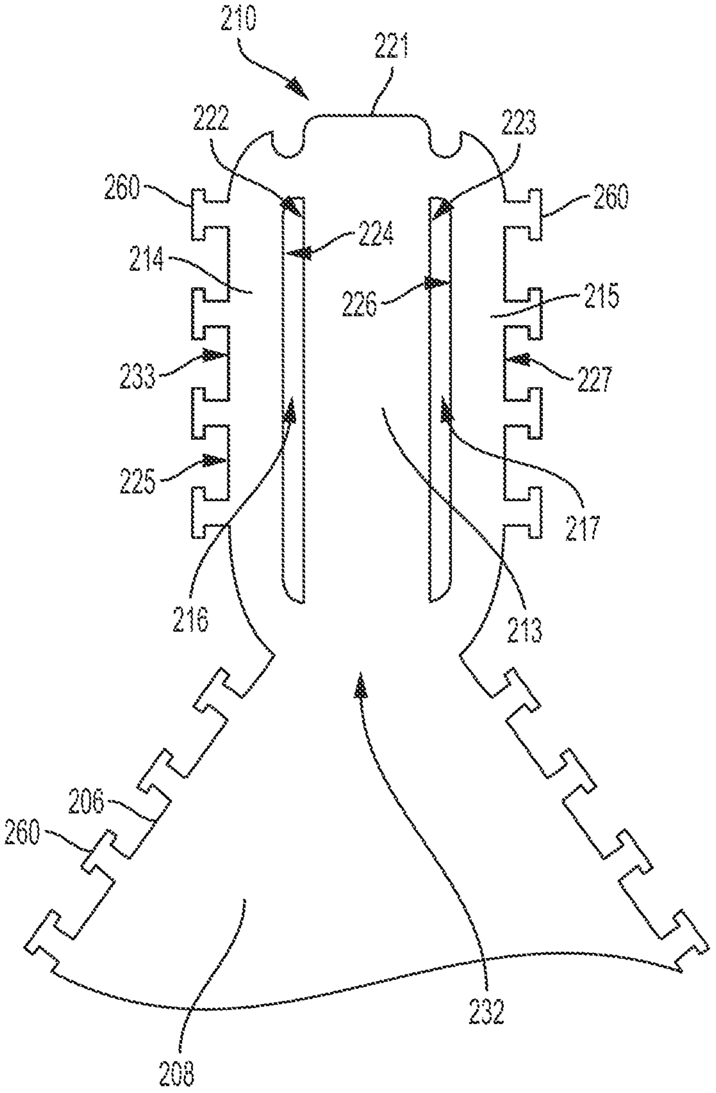
FIG. 8 is magnified view of a commissure post, according to some embodiments.

Turning now to FIG. 8, a commissure post 210 of a leaflet frame 200 is illustrated as including a spine 213, a first tine 214, second tine 215, a first slot 216 defined between at least the first tine 214 and the spine 213, and a second slot 217 defined between at least the second tine 215 and the spine 213. As shown, the ends of each of the first and second tines 214 and 215 terminate into or extend from the leaflet frame 200. Specifically, as shown, the first tine 214 includes a first end that extends from or is otherwise coupled to (or terminates into) the commissure post 210 at a position above or superior to the first slot 216, as well as a second end that extends from or is otherwise coupled to (or terminates into) the apex 232 of the commissure post support 208. The termination of the respective ends of the first tine 214 into the leaflet frame 200 provides for a first slot 216 that is closed. It will be appreciated that any portion of a leaflet 310 passing through the first slot 216 will require threading of the leaflet 310 into the first slot 216 from one of the post inner side 212 and post outer side 211.

Similarly, the second tine 215 includes a first end that extends from or is otherwise coupled to (or terminates into) the commissure post 210 at a position above or superior to the second slot 217, as well as a second end that extends from or is otherwise coupled to (or terminates into) the apex 232 of the commissure post support 208. The termination of the respective ends of the second tine 215 into the leaflet frame 200 provides for a closed second slot 217. It will be appreciated that any portion of a leaflet 310 passing through the second slot 217 will require threading of the leaflet 310 into the second slot 217 from one of the post inner side 212 and post outer side 211.

Figure 9B:
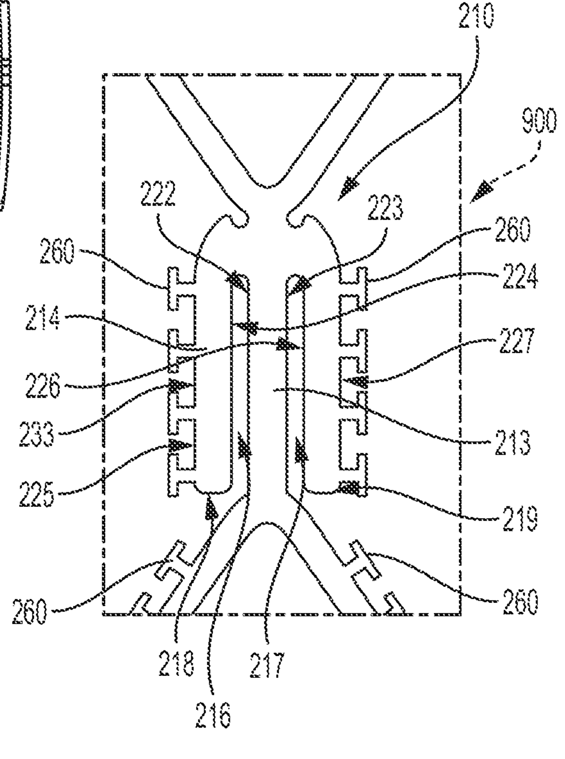
FIG. 9B is a magnified view of circle B in FIG. 9A.
Figure 10:
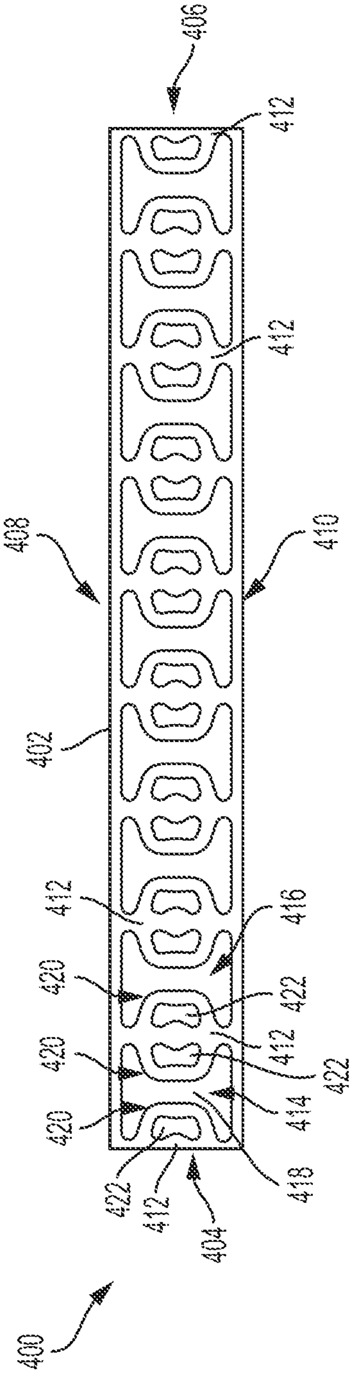
FIG. 10 is a top view of a leaflet retention remember, according to some embodiments.

As discussed above, the prosthetic valve 100 of the present disclosure is configurable for both transcatheter and surgical devices. With reference now to FIGS. 9A and 9B a leaflet frame 900 that is operable to be used in a transcatheter procedure, wherein the leaflet frame 900 has a smaller pre-deployment diameter and a larger deployed diameter. As mentioned above, it is understood that embodiments of leaflet frame projections 260 and the specific configurations of the commissure post 210 discussed herein are operable to be used for either surgical or transcatheter prosthetic heart valves.

FIG. 9A is an outflow-side, perspective view of a non-limiting example of a leaflet frame 900 for use in a transcatheter procedure. FIG. 9B is a magnified view of circle B in FIG. 9A. Similar to the leaflet frame 200 discussed above, the leaflet frame 900 defines three leaflet windows 204, each of which follow the shape of the leaflet attachment region 330 of the leaflet. Example transcatheter configurations where a leaflet 310 is coupled to a leaflet frame for use in transcatheter procedures are illustrated and described in U.S. Pat. No. 9,855,141 to Dienno, referred to above.

However, in various embodiments, the above discussed commissure post 210 configurations including a plurality of tines and a plurality of slots separated by a spine are operable alternatives to those commissure post configurations of U.S. Pat. No. 9,855,141 to Dienno, referred to above.

Specifically, and with continued reference to FIGS. 9A and 9B, the leaflet frame 900 includes one or more commissure posts 210. As shown in FIG. 9B, and as similarly discussed above, the commissure post 210 of the leaflet frame 900 includes a spine 213, a first tine 214, second tine 215, a first slot 216 defined between at least the first tine 214 and the spine 213, and a second slot 217 defined between at least the second tine 215 and the spine 213.

While the first and second tines 214 and 215 of the commissure post 210 illustrated in FIGS. 9A and 9B include first and second free ends 218 and 219, respectively, it will be appreciated that one or more of the first and second tines 214 and 215 may be configured with both ends terminating into the leaflet frame 900, as discussed above with respect to FIG. 8.

As shown, the first and second slots 216 and 217 extend along either side of the spine 213 between the spine 213 and the first and second tines 214 and 215. In some embodiments, the spine 213 includes a first edge 222 and a second edge 223. In some embodiments, the first edge 222 of the spine 213 faces the first tine 214 and defines the first slot 216, in part. Similarly, in some embodiments, the second edge 223 of the spine 213 faces the second tine 215 and defines the second slot 217, in part. As mentioned above, in various embodiments, one or more of the slots of the commissure posts 210 may extend or be oriented such that a longitudinal length of the slot is substantially parallel with a central longitudinal axis of the leaflet frame 900. Additionally or alternatively, one or more of the slots of the commissure posts 210 may curve slightly. In various embodiments, each slot of the commissure post 210 is dimensioned to have a width that accommodates the thickness of at least one of the leaflets 310, and a length that accommodates a portion of a length of the leaflet attachment region 330 that is couplable to the respective tine of the commissure post 210, as discussed in additional detail below.

In various embodiments, the first slot 216 is further defined by a first interior edge 224 of the first tine 214. The first interior edge 224 of the first tine 214 generally extends along a portion of the first tine 214 facing the spine 213 of the commissure post 210 between the first free end 218 of the first tine 214 and a region where the first tine 214 couples to or otherwise extends from the commissure post 210. Similarly, in various embodiments, the second slot 217 is further defined by a second interior edge 226 of the second tine 215. The second interior edge 226 of the second tine 215 generally extends along a portion of the second tine 215 facing the spine 213 of the commissure post 210 between the second free end 219 of the second tine 215 and a region where the second tine 215 couples to or otherwise extends from the spine 213. It will be appreciated that in embodiments where the tines of the commissure post do not include a free end, the interior edges of the respective tines generally extend between regions where the tines couple to or otherwise extend from the leaflet frame 900 (including the commissure post 210). As mentioned above, each slot of the commissure post 210 is configured to accommodate a portion of a leaflet 310 being extended therethrough for mating or otherwise coupling the leaflet 310 to the leaflet frame 900. In some embodiments, a width of the slots remains constant, while in other embodiments, one or more of the slots include one or more tapered regions, such as one or more tapered ends where the width of the slot decreases.

As similarly discussed above, in addition to an interior edge, each tine of the commissure post 210 generally includes an exterior edge. For example, the first tine 214 includes a first exterior edge 225 that extends between the first free end 218 of the first tine 214 and the commissure tip 221. Similarly, the second tine 215 includes a second exterior edge 227 that extends between the second free end 219 of the second tine 215 and the commissure tip 221.

In various embodiments, the first edge 222 of the spine 213 is continuous with or otherwise intersects with the first interior edge 224 of the first tine 214. Similarly, in various embodiments, the second edge 223 of the spine 213 is continuous with or otherwise intersects with the second interior edge 226 of the second tine 215.

In various embodiments, one or more leaflet frame projections 260 extend from the first and second exterior edges 225 and 227 of the first and second tines 214 and 215, respectively. Thus, in various embodiments, one or more of the tines of the commissure post 210 includes one or more leaflet frame projections 260 that extend from a surface opposite a surface of the tine defining a slot through which a leaflet 310 extends for the purpose of mating or otherwise coupling the leaflet 310 to the leaflet frame 900.

As mentioned above, such a configuration provides that a portion of a leaflet 310 may be wrapped (partially or completely) about a tine prior to being secured to the one or more leaflet frame projections 260 extending from the exterior edge of the tine. In various embodiments, the wrapping the leaflet 310 about a portion of the leaflet frame 900 prior to securing of the leaflet 310 to the leaflet frame projections 260 extending from the exterior edge of a tine of the commissure post 210 operates to maintain a couple between the leaflet 310 and the leaflet frame 900, minimize undesirable loading and stress concentrations in the leaflet 310, and minimize a potential for failure of the leaflet 310 due to fatigue (due at least in part to a "capstan effect").

As mentioned above, in addition to engagement with one or more of the leaflet frame projections 260, the leaflet 310 can be fixed to or otherwise coupled with one or more portions of the leaflet frame 200 by way winding one or more portions of the leaflet frame about one or more retaining elements, such as one or more fibers. For example, a retaining element is positioned on either side of a slot and portion of a leaflet is passed back and forth through a slot a plurality of times, such that the leaflet forms a portion of a loop on either side of the slot. In some embodiments, a retaining element is positioned within each loop formed on either side of the slot such that the leaflet encircles each retaining element. Generally, the width of the loops formed by the leaflet encircling the retaining elements exceeds a width of the slot such that the leaflets and the retaining element are prevented from pulling through the slot.

In accordance with various additional embodiments, the prosthetic valves illustrated and described herein can be incorporated into a valved conduit. Valved conduits may be used for replacing a native heart valve and an associated blood vessel in a patient. The pulmonary valve and the pulmonary artery represent one non-limiting example of such a valve and an associated blood vessel. The aortic valve and the ascending aorta are another such example. The conduit portion of such a valved conduit generally includes an elongate tube, such as an elongate polymeric tube, where the prosthetic valve 100 is disposed within the elongate polymeric tube. In certain embodiments, the conduit is formed from expanded Polytetrafluoroethylene (ePTFE). The prosthetic valve (e.g., 100, 900, 1010) may be coupled to the elongate polymeric tube according to known methods, including without limitation, adhesives, fasteners, suturing, and frictional retention. The conduit generally defines a conduit first end and a conduit second end. In various examples, the prosthetic valve (e.g., 100, 900, 1010) is disposed within the conduit. In some examples, the prosthetic valve is disposed within the conduit at one of the first and second ends of the conduit. In some examples, the prosthetic valve is disposed within the conduit between the first and second ends. For instance, in some examples, the prosthetic valve is disposed within the conduit such that a portion of the conduit extends axially outwardly from one or more of the inflow and outflow ends of the prosthetic valve to define a conduit lumen that is contiguous along a longitudinal axis of the prosthetic valve with the plurality of the leaflets 310, which are operable within the conduit lumen. Examples of valved conduits and the integration of various prosthetic valves into the same are illustrated and described in U.S. Pat. No. 9,855,141 to Dienno, referred to above. It will be appreciated that the prosthetic valves 100 (e.g., including leaflet frames 200, 900, and 1020) of the present disclosure are operable to be incorporated into valved conduits in the same or similar manner as are those prosthetic valves illustrated and described in U.S. Pat. No. 9,937,037 to Dienno.

A method of making a prosthetic valve, in accordance various embodiments, comprises forming (such as by cutting a metal tube, casting, molding, printing, or the like) a leaflet frame defining leaflet frame windows and one or more leaflet retention surfaces, having commissure posts therebetween, and a plurality of projections spaced apart from each other extending from one or more leaflet retention surfaces. In various embodiments, each leaflet frame projection is configured to couple to a leaflet. The leaflet frame projections can have a projection base portion and a projection head portion, where the projection base portion meets the leaflet retention surface at one side and the projection head portion on the opposite side. Some embodiments of the leaflet frame can further define one or more slots that extend through one or more frame elements that define the leaflet frame windows. Each slot is dimensioned to receive at least a single thickness of the leaflet, e.g., the leaflet attachment region. The slot can be a base receiving slot or a side receiving slot. In addition, each commissure post defines a post slot dimensioned to receive a double thickness of the leaflet. In further embodiments, the frames can comprise one or more attachment slots or other frame openings that defines an internal edge from which leaflet frame projections can extend.

The same or different method can comprise obtaining a sheet or tube of material comprising one or more layers of expanded PTFE composite and cutting a leaflet from the sheet or tube, where one or more apertures are formed in the leaflet attachment region of the leaflet. The apertures can be cut to dimensions suitable for coupling to a leaflet frame projection on a leaflet frame. In particular, the aperture can have a size and shape that is substantially the same as a transverse, cross-sectional size and shape of the projection base portion of the leaflet frame projection. The method can further comprise coupling a leaflet reinforcement to the leaflet and further, cutting the leaflet apertures into both the leaflet and the leaflet reinforcement simultaneously.

The same or different method can comprise coupling the leaflet to the leaflet frame by aligning an aperture on the leaflet with the corresponding projection on the leaflet frame, pressing the leaflet so that the leaflet projection extends through the aperture, and/or pressing the leaflet frame so that the leaflet projections extends through the apertures. In a further embodiment, the method can comprise pressing either the leaflet or the leaflet frame so that a leaflet surface defining the aperture contacts the leaflet retention surface. These steps can be repeated for the adjacent aperture and the corresponding adjacent projection until each aperture extends through a corresponding one of the leaflet frame projections.

In some embodiments, prior to pressing the leaflet frame so that the leaflet projections extends through the apertures of the leaflet, passing one or more portions of the leaflet through one or more slots in the leaflet frame and wrapping the same about the leaflet frame to achieve one of the various threaded and wrapped configurations illustrated and described above. That is, in some embodiments, coupling the leaflet to the leaflet frame can comprise first passing a portion of the leaflet defining the leaflet attachment region through a receiving slot (e.g., in the commissure post, the commissure post support, the leaflet window base, or some other suitable feature of the leaflet frame as described herein) and then wrapping the leaflet attachment region around one or more features of the leaflet frame (e.g., a tine of the commissure post), and then aligning one of the apertures on the leaflet with the corresponding projection on the leaflet frame, pressing the leaflet frame projection through the aperture, and seating the leaflet about the leaflet frame projection. These steps can be repeated for the adjacent aperture and corresponding projection until all apertures extend through a projection. Alternatively, in some embodiments, the leaflet attachment region may be wrapped around one or more features of the leaflet frame (e.g., a tine of the commissure post) prior to passing a portion of the leaflet defining the leaflet attachment region through one or more receiving slots.

Additionally or alternatively, in various embodiments, one or more leaflet retention features can be utilized to secure the leaflets to the leaflet frame 200. In various embodiments, the leaflet retention feature is configured such that is can be coupled to the leaflet frame 200. In some examples, the leaflet retention feature may include one or more structural elements that are configured to interface with one or more portions of the leaflet frame 200, such as one or more of the leaflet frame projections 260, wherein the interaction of the one or more structural elements with the one or more portions of the leaflet frame 200 operates to couple the leaflet retention feature to the leaflet frame 200. In some examples, the leaflet retention feature includes a fiber or wire that is interwoven with one or more features of the leaflet frame 200, such as one or more of the leaflet frame projections 260. The leaflet retention feature is generally coupled to the leaflet frame 200 such that the leaflet 310 is situated between the leaflet frame 200 and the leaflet retention feature, and thus may be secured to the leaflet frame 200 after the leaflets 310 are disposed over the leaflet frame projections 260. In some examples, a plurality of discrete leaflet retention features are utilized to secure the leaflet 310 to the leaflet frame 200.

In some examples, the leaflet retention features operate to minimize a potential for the leaflets 310 to decouple from the leaflet frame 200. For instance, in some examples, the leaflet retention features help minimize a potential of the leaflets 310 "backing-off" of the leaflet frame projections 260. That is, in some examples, the leaflet retention features are positioned adjacent the leaflets 310 and engage the leaflet frame 200 (e.g., by engaging the leaflet frame projections 260) such that the leaflets 310 are physically obstructed from backing-off the leaflet frame projections 260 by the leaflet retention features. In some examples, the leaflet retention features are configured such that they apply a normal force to the leaflets 310 when coupled to the leaflet frame 200, thereby compressing the portion of the leaflet 310 situated between the leaflet frame 200 and the leaflet retention member. In some examples, a configuration that includes compressing a portion of the leaflet 310 helps mitigate or minimize abrasion wear of the leaflet 310 under normal operating conditions.

FIGS. 10 to 13 provide an illustration of an example leaflet retention feature 400 that can be utilized to secure a leaflet 310 to a leaflet frame 200. The leaflet retention feature 400 generally includes one or more features, elements, or components that accommodate, receive, or otherwise engage one or more of the leaflet frame projections 260 in a manner that maintains a couple between the leaflet retention feature 400 and the leaflet frame 200. Such a couple is generally one of friction and/or interference. The leaflet retention feature 400 can be formed any metal, metal alloy, or polymeric material as discussed herein, and can be formed through one or more known chemical etching, laser cutting, or micro-molding processes.

The leaflet retention feature 400 generally includes a body 402 having a first end 404, a second end 406 opposite the first end 404, a first side 408, and a second side 410 opposite the first side 208. In some examples, the first and second sides 408 and 410 extend between the first and second ends 404 and 406. In various examples, the leaflet retention feature 400 includes one or more struts 412 extending between the first and second sides 408 and 410. That is, in various examples, one or more struts 412 interconnect or otherwise interlink the first and second sides 408 and 410. In some examples, one or more of these struts define the first and second ends 404 and 406.

In various examples, the one or more struts 412 split the leaflet retention feature into a plurality of cells, such as 414 and 416. As shown, the plurality of cells are defined between the first and second sides 408 and 410 and adjacently situated struts 412. In various examples, one or more of the cells are "closed cells" in that the adjacently struts 412 define the cell extend between and terminate into the first and second sides 408 and 410 such that a closed interior region 418 is defined between the first and second sides 408 and 410 and adjacently situated struts 412. In some examples, each of the cells of the leaflet retention feature 400 is a closed cell. However, in various other examples, the leaflet retention feature 400 may additionally or alternatively include one or more "open cells," or one or more of cells not otherwise defining closed interior region, as discussed in greater detail below. For instance, in some examples, the leaflet retention feature 400 includes one or more struts 412 having a free end (e.g., one or more struts 412 that do not otherwise extend between the first and second sides 408 and 410).

In various examples, when coupled with the leaflet frame 200, the interior regions 418 are configured to accommodate the leaflet frame projections 260. For instance, in various examples, the leaflet retention feature 400 is disposed over the leaflet frame 200 such that the leaflet frame projections 260 are received within or otherwise extend through the interior regions 418 of the cells of the leaflet retention feature 400. In various examples, one or more of the first and second sides, and the adjacently situated struts engage or otherwise interface with the leaflet frame projection extending through the interior region. This engagement or interaction between the leaflet frame projection 260 and one or more features of the leaflet retention feature 400 operations to maintain a couple between the leaflet frame 200 and the leaflet retention feature 400.

In some examples, the engagement or interaction between the leaflet frame projection 260 and one or more features of the leaflet retention feature 400 is facilitated by a distance between adjacently situated struts 412 being less than a maximum transverse dimension of the leaflet frame projection 260, as those of skill will appreciate. Additionally or alternatively, in some examples, a distance between the first and second sides 408 and 410 less than a maximum transverse dimension of the leaflet frame projection 260, as those of skill will appreciate. It will thus be appreciated that the engagement or interaction between the leaflet frame projection 260 and one or more features of the leaflet retention feature 400 may be facilitated by way of an interference fit (e.g., friction or press fit).

In various examples, the leaflet retention feature 400 includes one or more deflectable ears 420 that project into the interior region 418 and that are configured to engage a leaflet frame projection 260 extending through the interior region 418. In some examples, the ears 420 engage the leaflet frame projection 260 extending through the interior region 418 via an interference fit (see discussion above). In some examples, one or more ears 420 extend from one or more of the struts 412. Additionally or alternatively, in some examples, one or more ears 420 extend from one or more of the first and second sides 408 and 410.

Figure 11:
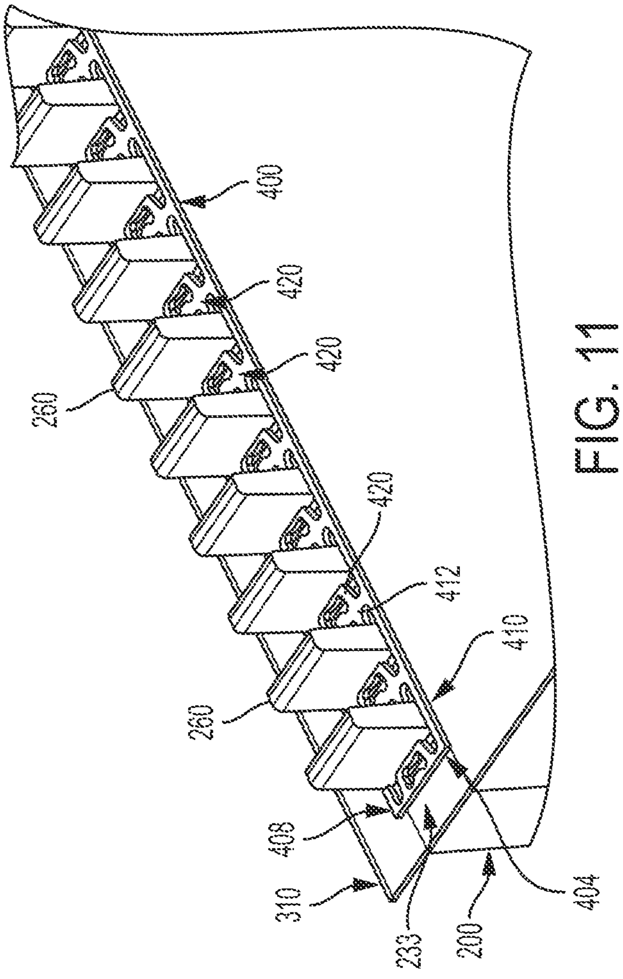
FIG. 11 is a perspective view of a leaflet retention member disposed about projections of a leaflet frame, according to some embodiments.
Figure 12:
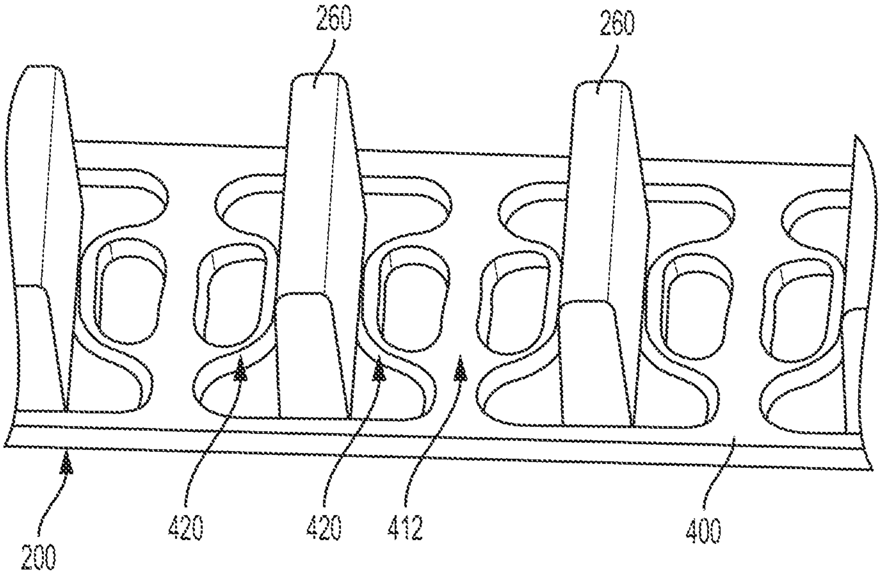
FIG. 12 is a top perspective view of a leaflet retention member disposed about projections of a leaflet frame, according to some embodiments.
Figure 13:
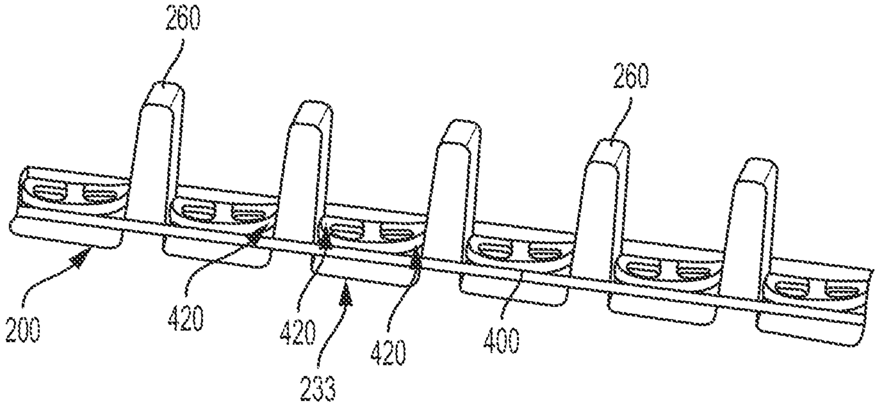
FIG. 13 is a front view of a leaflet retention member disposed about projections of a leaflet frame, according to some embodiments.

With continued reference to FIGS. 11 to 13, the leaflet retention feature 400 is a multi-celled structure including a plurality of struts 412 extending between first and second sides 408 and 410. Each cell includes a plurality of ear 420 extending into an interior region thereof and engaging a leaflet frame projection 260 extending therethrough. As shown in FIGS. 12 and 13, in various examples, the ears 420 are deflectable. Specifically, as the leaflet retention feature 400 is disposed over the leaflet frame projections 260, an interference between the leaflet retention feature 400 and the leaflet frame projections 260 (see explanation above) causes the ears 420 to deflect, as those of skill will appreciate. Such a configuration provides that the energy stored in the deflected ears 420 operates to maintain a couple between the leaflet frame projection 260 and the leaflet retention feature 400, thereby retaining the leaflet 310 between the leaflet frame 200 and the leaflet retention feature 400.

Generally, the leaflet retention feature 400 is coupled with the leaflet frame 200 by disposing the leaflet retention feature 400 over the leaflet frame projections 260 such that the leaflet frame projections extend through the interior region of each of the cells of the leaflet retention feature 400. In some examples, the leaflet retention feature 400 is then advanced along the leaflet frame projections 260 toward the leaflet retention surface 233 from which the leaflet frame projection 260 extends. Generally, the leaflet retention feature 400 is advanced until the leaflet retention feature 400 contacts the leaflet 310, and/or until the leaflet retention feature 400 is advanced to a designated position along the leaflet frame projection 260, and/or until the leaflet retention feature 400 is properly seated within one or more features of the leaflet frame projection 260 (see further explanation below), and/or until the leaflet retention feature 400 contacts the leaflet 310 and the leaflet 310 contacts the leaflet retention surface 233.

In some embodiments, the leaflet retention feature 400 may be bonded or otherwise coupled to leaflet 310. In some examples, leaflet retention feature 400 is bonded or otherwise coupled to the leaflet attachment region 330 of the leaflet 310. The leaflet retention feature 400 may be bonded or coupled to the leaflet 310 using known methods (e.g., suturing, adhesives, thermal processing, chemical processing, etc.). Generally, the leaflet retention feature 400 may be bonded or otherwise coupled either side (e.g., an inflow side or an outflow side) of the leaflet 310 depending on the desired attachment arrangement (e.g., whether the associated portion of the leaflet attachment region 330 is to be wrapped about the leaflet frame 200 prior to disposing the leaflet 310 and the leaflet retention feature 400 over the leaflet frame projections 206). For instance, in some examples where the associated portion of the leaflet attachment region 330 is not wound or wrapped about the leaflet frame prior to being disposed over the leaflet frame projections 260, the leaflet retention feature 400 may be coupled to the outflow side of the leaflet 310. Conversely, in some examples where the associated portion of the leaflet attachment region 330 is wound or wrapped about the leaflet frame 200 prior to being disposed over the leaflet frame projections 260, the leaflet retention feature 400 may be coupled to the inflow side of the leaflet 310. However, in some examples where the leaflet retention feature is bonded or otherwise coupled to the leaflet attachment region 330 of the leaflet 310, it may be desirable to dispose the leaflet 310 and the leaflet retention feature 400 about the leaflet frame projection 260 such that the leaflet frame projection 260 is situated between the leaflet retention surface 233 of the leaflet frame 200 and the leaflet 310.

In some examples, the leaflet 310 may be additionally or alternatively wrapped or wound around the leaflet retention member prior to disposing the leaflet 310 and the leaflet retention feature 400 over the leaflet frame projections 206. In some such examples, the leaflet 310 may be wrapped about the leaflet retention feature 400 such, when coupled with the leaflet frame 200, a first portion of the leaflet 310 is sandwiched between the leaflet retention feature 400 and the leaflet frame 200, and such that the leaflet retention feature 400 is sandwiched between the first portion of the leaflet 310 and a second portion of the leaflet 310. In some examples, the leaflet attachment region 330 is folded back over itself to form a pocket and the leaflet retention feature 400 is situated within the pocket such that the interior regions of the are aligned with the leaflet apertures 308 of the leaflets 310 such that the leaflets 310 and the leaflet retention features 400 can be disposed over the leaflet frame projections 260 of the leaflet frame 200. Thus, in some examples, the leaflet retention feature 400 may be fully enveloped or encapsulated by the leaflet 310.

In some examples where the leaflet 310 is folded back over itself to form a pocket for receiving the leaflet retention feature 400, the leaflet 310 generally includes a plurality of rows of leaflet apertures 308 including a first row and a second row such that when folded back over itself to form the pocket for accommodating the leaflet retention features 400, the corresponding leaflet apertures 308 of the first and second rows of apertures are aligned with one another. In some examples, when disposed over the leaflet frame projections 260, each leaflet frame projection extending through the leaflet 310 and the leaflet retention feature 400 extends through each of a first aperture of the first row of apertures, a first interior region of a first cell of the leaflet retention member, and a first aperture of the second row of apertures.

Figure 15:
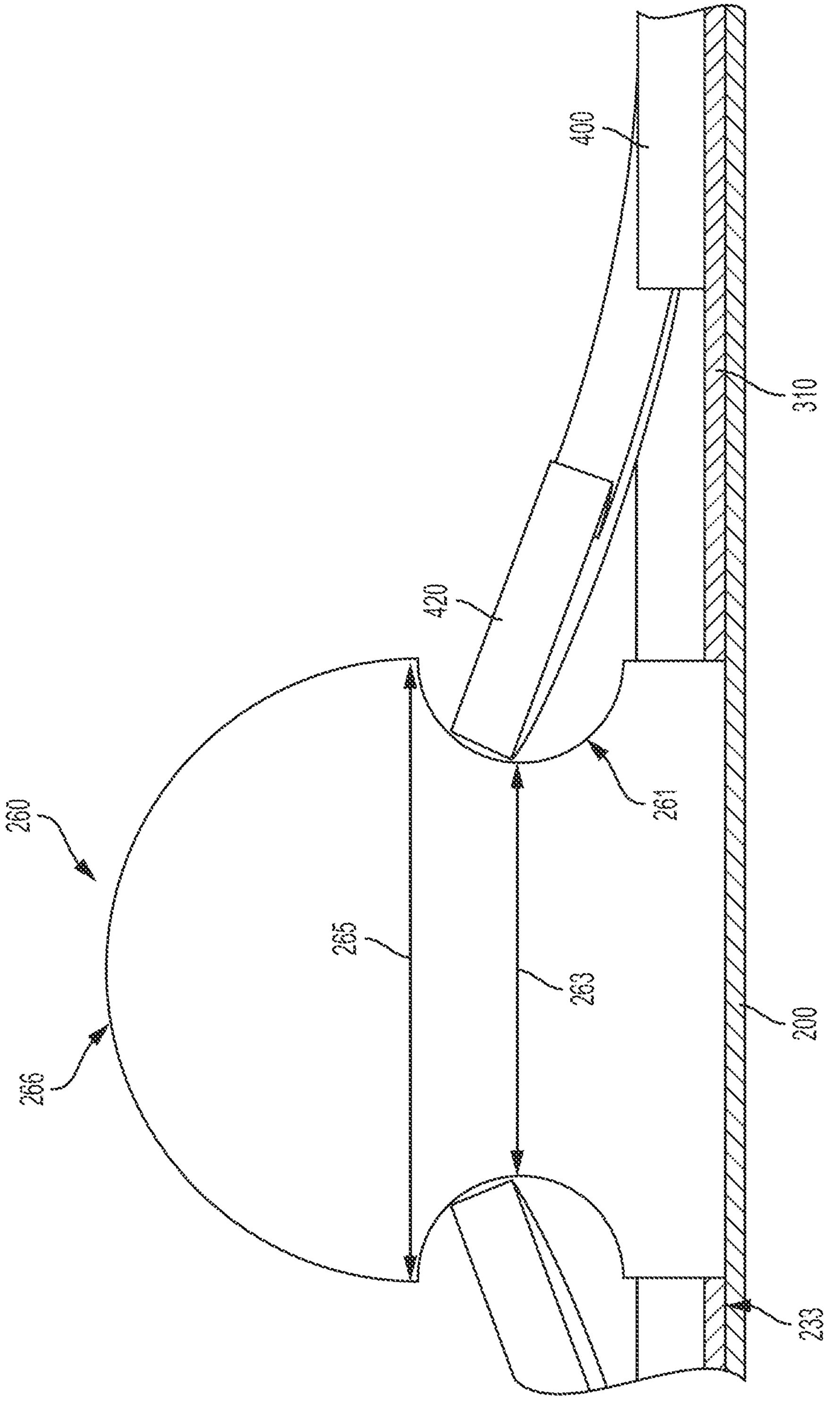
FIG. 15 is a side view illustrating a leaflet retention member interfacing with a projection of a leaflet frame, according to some embodiments.

In various examples, the ears 420 of the leaflet retention feature 400 deflect away from the leaflet retention surface 233 as the leaflet retention feature 400 is advanced along the leaflet frame projections 260, as shown in FIGS. 12 and 13, and as those of skill will appreciate. Similar deflection of an ear 420 is shown in FIG. 15. In various examples, the leaflet frame projection 260 is sandwiched between or otherwise positioned between adjacently situated ears 420 (see FIGS. 11 to 13). As mentioned above, adjacently situated ears 420 may extend from adjacently situated struts 412, and/or from opposing first and second sides 408 and 410.

In various examples, one or more apertures 422 are formed in the ears 420 of the leaflet retention feature 400. In some examples, the apertures operate to increase the flexibility or otherwise reduce a stiffness of the ears 422. Put differently, in some examples, the apertures operate to reduce an amount of force required to deflect the ears 422 an amount required to achieve the desired interference fit between the ears 422 and the leaflet frame projections 260. It will be appreciated that the size and shape of the apertures 422 illustrated and described herein are not to be interpreted as limited, and that the apertures 422 can be sized and shaped according to any desired profile to achieve a designated flexibility of the ears 422. Similarly, in some examples, the leaflet retention feature 400 is formed without any apertures 422.

In various examples, release of the leaflet retention feature 400 from the leaflet frame projections 260 generally requires sliding the leaflet retention feature 400 along the leaflet frame projections 260 away from the leaflet retention surface 233. In some examples, due to the interference fit between the leaflet retention feature 400 (e.g., including the ears 420) and the leaflet frame projections 260, release of the leaflet retention feature 400 from the leaflet frame projections 260 additionally requires one of bending of the ears 420 away from the leaflet frame projection 260, and/or inverting of the ears 420 such that the ears 420 deflect toward the leaflet retention surface 233, as those of skill will appreciate.

Figure 14:
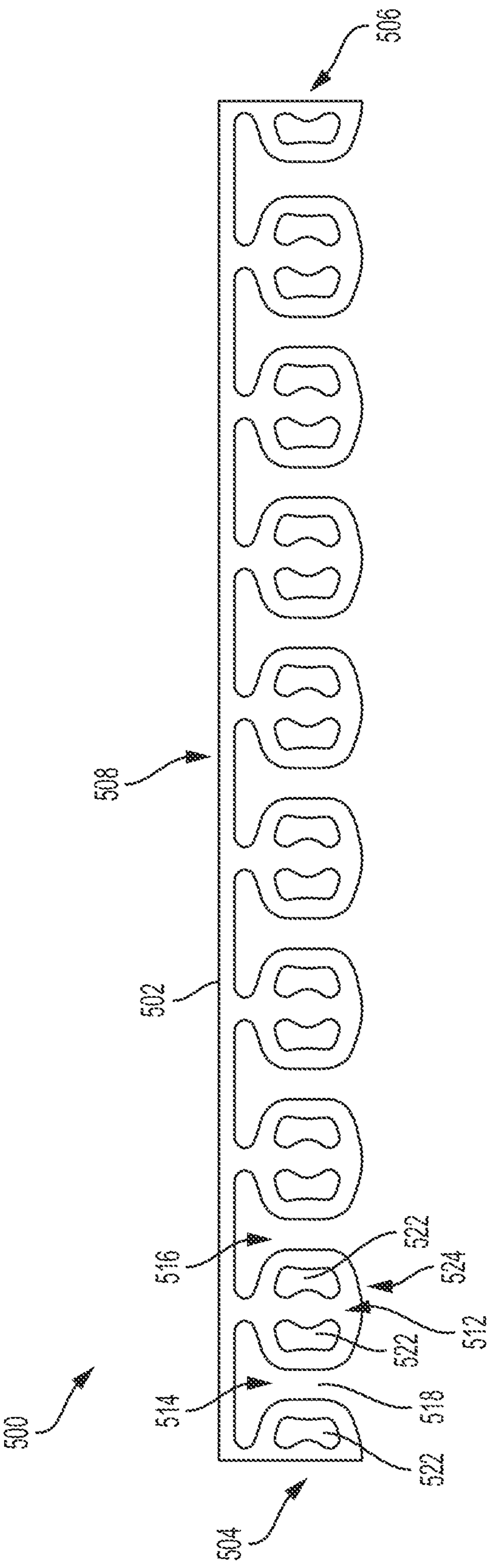
FIG. 14 is a top view of a leaflet retention remember, according to some embodiments.

FIG. 14 is a top view of a leaflet retention feature 500. The leaflet retention feature 500 is generally similar to the leaflet retention feature 400 discussed above, with the exception that the struts 512 have a free end 524. As shown, the leaflet retention feature 500 includes a body 502, a first end 504, a second end 506 opposite the first end 504 and a first side 508 extending between the first and second ends 504 and 506. The leaflet retention feature 500 also includes a plurality of struts 512 that extend from the first side 508. However, as shown in FIG. 14, each of the plurality of struts 512 include a free end 524 that projects away from where the struts are coupled to the body 502. Similar to the leaflet retention feature 400, the leaflet retention feature 500 includes a plurality of cells, such as cells 514 and 516. However, unlike cells 414 and 416, cells 514 and 516 are “open cells” in that they are not fully enclosed (or otherwise bordered) by elements of the leaflet retention feature 500. Instead, as shown, a region 518 defined between adjacently situated struts 512 is exposed or not otherwise enclosed. In various examples, similar to the leaflet retention feature 400, the leaflet retention feature 500 includes a plurality of ears 520 that project into the region 518 defined between adjacently situated struts 512.

The leaflet retention feature 500 is coupled to the leaflet frame 200 of the prosthetic valve 100 in the same manner as the leaflet retention feature 500. Specifically, the leaflet retention feature 500 is coupled with the leaflet frame 200 by disposing the leaflet retention feature 500 over the leaflet frame projections 260 such that the leaflet frame projections extend through the interior region of each of the cells of the leaflet retention feature 500, as discussed above. In some examples, the leaflet retention feature 500 is then advanced along the leaflet frame projections 260 toward the leaflet retention surface 233 from which the leaflet frame projection 260 extends, as discussed above. Generally, the leaflet retention feature 500 is advanced until the leaflet retention feature 500 contacts the leaflet 310, and/or until the leaflet retention feature 500 is advanced to a designated position along the leaflet frame projection 260, and/or until the leaflet retention feature 500 is properly seated within one or more features of the leaflet frame projection 260, and/or until the leaflet retention feature 500 contacts the leaflet 310 and the leaflet 310 contacts the leaflet retention surface 233.

In various examples, the configuration of the leaflet retention feature 500 provides for a leaflet retention feature having a smaller profile with additional degrees of freedom.

In some examples, a leaflet retention feature having a smaller profile can be coupled with the leaflet frame 200 such that the leaflet retention feature 400 does not project from a maximum outside profile of the leaflet frame 200. Specifically, and drawing a comparison with the leaflet retention feature 400, the leaflet retention feature 400 includes the first side 408 and the second side 410. When coupled with the leaflet frame 200, the first and second sides 408 and 410 effectively straddle the leaflet frame projections 260. In examples where the leaflet frame projections 260 are as wide as the leaflet retention surfaces 233 from which they project, the first and second sides 408 and 410 extend radially inwardly of and radially outwardly of the leaflet retention surfaces 233 (and in some configurations radially inwardly of the leaflet frame inner surface 202 and radially outwardly of the leaflet frame outer surface 203). In some examples, such a configuration results in the leaflet retention features 400 extending radially outwardly of a maximum outside profile of the leaflet frame 200 (e.g., radially outwardly of the leaflet frame outer surface 203). On the other hand, because leaflet retention feature 500 includes only one side 508, the leaflet retention feature 500 can be coupled with the leaflet frame 200 such that the first side 508 extends along and radially inwardly of the leaflet frame inner surface 202, without extending radially outwardly of a maximum outside profile of the leaflet frame 200 (e.g., radially outwardly of the leaflet frame outer surface 203). In particular, in some examples, the struts 512 extend from the first side 508 a distance less than a width of the leaflet retention surface 233 defined between the leaflet frame inner and outer surfaces 202 and 203.

Additionally, as mentioned above, the configuration of the leaflet retention feature 500 provides for a leaflet retention feature having additional degrees of freedom in comparison with the leaflet retention feature 400 having first and second sides. For example, the leaflet retention feature 500 can be bent about a longitudinal axis of the leaflet frame 200. On the other hand, bending the leaflet retention feature 400 in a similar manner generally requires an elongation of one of the first and second sides 408 and 410, and a corresponding compression/reduction in length of the other of the first and second sides 408 and 410, as those of skill will appreciate. The configuration of the leaflet retention feature 400 is thus more rigid and less conformable than is the configuration of the leaflet retention feature 500.

Such a configuration is generally associated with improved conformability. For instance, in some examples, the leaflet frame 200 is curved or cylindrical (see, e.g., FIG. 1D), and includes leaflet frame projections 260 extending from leaflet retention surfaces 233 that are arced or curved in accordance with the curved or cylindrical profile of the leaflet frame 200. Thus, the leaflet frame projections 260, in some instances, are not linearly arranged. Instead, in various examples, because the leaflet frame projections 260 project from some leaflet retention surfaces 233 that are arced or curved, some of the leaflet frame projections 260 are situated in a curved or nonlinear arrangement. A highly conformable leaflet retention feature, like leaflet retention feature 500, is operable to adopt or otherwise conform to such a nonlinear arrangement (e.g., is operable to be bent about a longitudinal axis of the leaflet frame 200), as mentioned above.

It will be appreciated, however, that in various examples, the leaflet retention feature 400 can be pre-formed in accordance with a curvature or a curved arrangement of the leaflet frame projections 260.

As mentioned above, in various examples, when coupling the leaflet retention feature 400 with the leaflet frame 200, the leaflet retention feature 400 is advanced along the leaflet frame projections 260 until the leaflet retention feature 500 is advanced to a designated position along the leaflet frame projection 260, and/or until the leaflet retention feature 500 is properly seated within one or more features of the leaflet frame projection 260. In some examples, one or more retaining features 261 are formed in the leaflet frame projection 260. These one or more retaining features may include one or more reliefs, one or more projections, and/or one or more textured surfaces. As mentioned above, in various examples, the projection head portion 264 of the leaflet frame projection 260 has a wider second transverse dimension 265 than the narrowest first transverse dimension 263 of the projection base portion 262 of the leaflet frame projection 260 (see, e.g., FIGS. 3A-3D and 14).

In some examples, narrowest first transverse dimension 263 may correspond with a retaining feature in the form of a relief 261, as shown in FIG. 14. In some examples, the relief 261 extends about an entire periphery of the leaflet frame projection 260. In some other examples, the relief 261 extends about only a portion of the periphery of the leaflet frame projection 260. For instance, in some examples, the leaflet frame projection 260 includes a plurality of reliefs 261 (e.g., a relief on either side of the leaflet frame projection), wherein each relief 261 extends along a portion of the leaflet frame projection between the leaflet frame inner and outer surfaces 202 and 203. In some other examples, the wider second transverse dimension 265 may correspond with a retaining feature in the form of a projection (not shown). It will be appreciated that the projection may be a suitable shape and size provided the leaflet retention feature 400 can be advanced along the leaflet frame projection 260 and can traverse the projection such that the wider second transverse dimension of the projection is situated between the leaflet retention feature 400 and the projection tip 266 of the leaflet frame projection 260.

As shown in FIG. 15, in some examples, the leaflet retention feature 400 has been advanced along the leaflet frame projection to a position where the leaflet retention feature 400 engages the relief 261 of the leaflet frame projection 260. While the relief 261 is shown in FIG. 15 as an arc or continuous curvature, it is to be appreciated that the relief may be of any suitable shape, such as a rectangular or triangular relief (see, e.g., FIGS. 3A-3C and 8-9B). As mentioned above, in various examples, release of the leaflet retention feature 400 from the leaflet frame projections 260 generally requires sliding the leaflet retention feature 400 along the leaflet frame projections 260 away from the leaflet retention surface 233. In some examples, due to the interference fit between the leaflet retention feature 400 (e.g., including the ears 420) and the leaflet frame projections 260, release of the leaflet retention feature 400 from the leaflet frame projections 260 additionally requires one of bending of the ears 420 away from the leaflet frame projection 260, and/or inverting of the ears 420 such that the ears 420 deflect toward the leaflet retention surface 233, as those of skill will appreciate.

Figure 17:
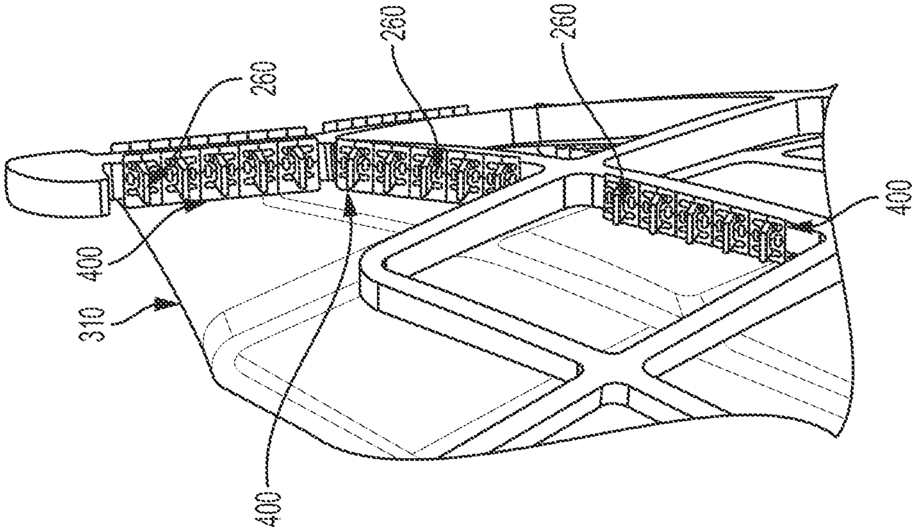
FIG. 17 is a magnified view of circle 17 in FIG. 16.
Figure 16:
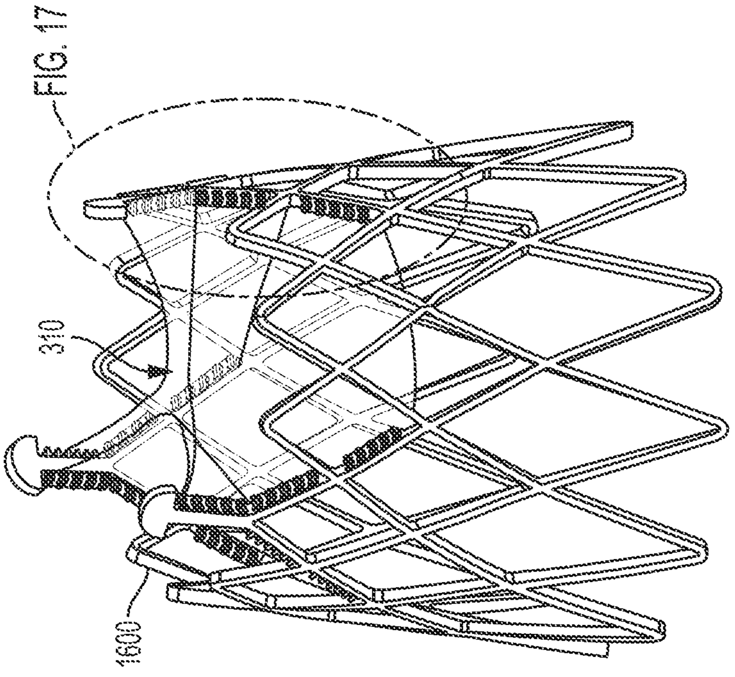
FIG. 16 is a perspective view of a leaflet frame for use in a transcatheter delivery procedure, according to some embodiments.

As discussed above, the prosthetic valve 100 of the present disclosure is configurable for both transcatheter and surgical devices. With reference now to FIGS. 16 and 17 a leaflet frame 1600 that is operable to be used in a transcatheter procedure, wherein the leaflet frame 1600 has a smaller pre-deployment diameter and a larger deployed diameter. As mentioned above, it is understood that embodiments of leaflet frame projections 260 and the leaflet retention features 400 discussed herein are operable to be used for either surgical or transcatheter prosthetic heart valves.

FIG. 16 is an outflow-side, perspective view of a non-limiting example of a leaflet frame 1600 for use in a transcatheter procedure. FIG. 17 is a magnified view of circle 17 in FIG. 16. Similar to the leaflet frames 200 and 900 discussed above, the leaflet frame 1600 defines a plurality of leaflet windows, each of which follow the shape of the leaflet attachment region 330 of the leaflet. Though not illustrated in FIGS. 16 and 17, it will be appreciated that the leaflets 310 may extend through one or more slots prior to being disposed over the leaflet frame projections 260. Similarly, not illustrated in FIGS. 16 and 17, it will be appreciated that the leaflets 310 may be wrapped and/or wound about one or more portion of the leaflet frame 1600 (e.g., one or more portions and/or tines of a commissure post) prior to be disposed over the leaflet frame projections 260, as discussed herein. Thus, the embodiments shown in FIGS. 16 and 17 are not to be construed as limiting, but are instead intended to illustrate the leaflet retention features 400 in association with a transcatheter prosthetic heart valve.

It will also be appreciated that, while not illustrated in FIGS. 16 and 17, in various examples, one or more surfaces, regions, or areas of the leaflet frame 1600 may be wrapped or covered with a film, as discussed above.

Figure 19:
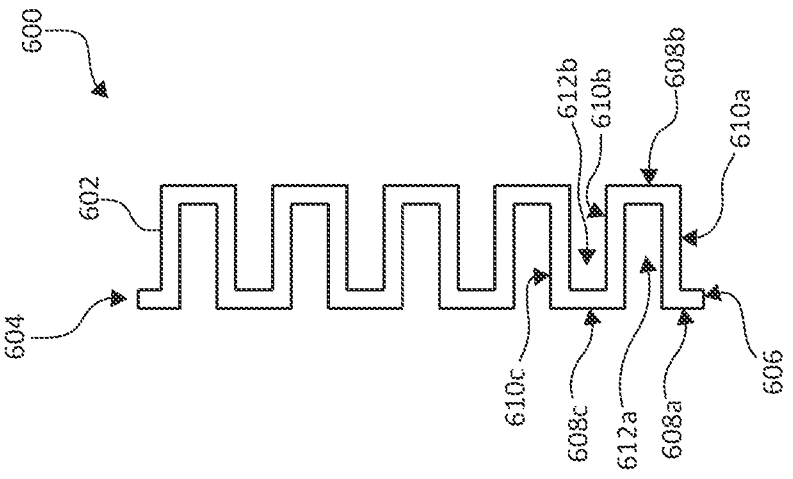
FIG. 19 is a magnified top view of region 19 of FIG. 18 showing the leaflet retention feature coupled to a leaflet frame, according to some embodiments.
Figure 18:
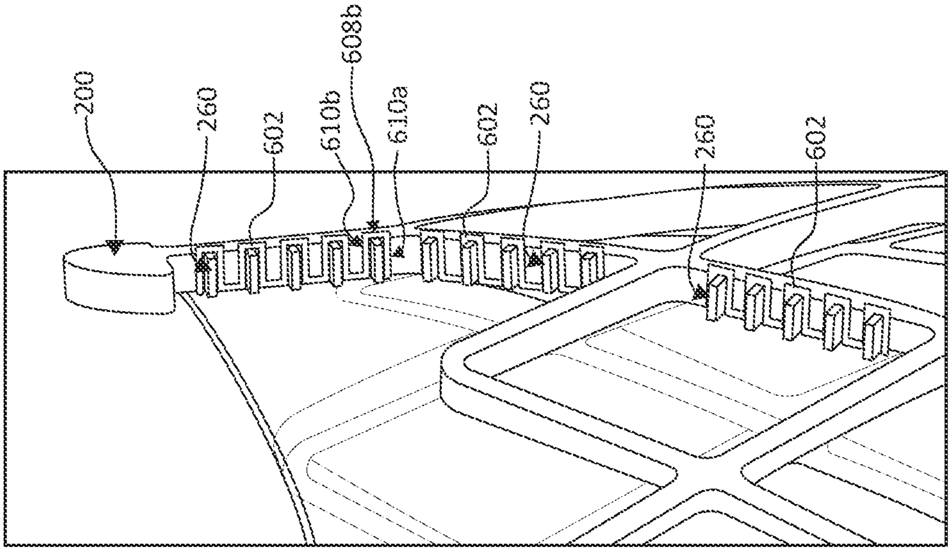
FIG. 18 is an illustration of a leaflet retention feature, according to some embodiments.

FIGS. 18 and 19 provide illustration of a leaflet retention feature 600. FIG. 18 is a is a perspective view of a portion of a leaflet frame 200 with the leaflet retention feature 600 coupled to leaflet frame projections 260 of the leaflet frame 200. It is to be appreciated that the configuration of the leaflet frame 200 illustrated in FIG. 18 should not be construed as limiting, and any leaflet frame configuration including a plurality of leaflet frame projections 260 as described herein may be utilized. Likewise, while the configuration of the leaflet frame projections 260 illustrated in FIG. 18 (and FIGS. 20, 22, and 25) is rectangular, it is to be appreciated that the leaflet frame projections 260 may be configured in accordance with any of the leaflet frame projection configurations described or referred to herein (see, e.g., FIGS. 1B, 2D, 3A-3E). FIG. 19 provides an example illustration of the leaflet retention feature 600 shown in FIG. 18. Like leaflet retention feature 500 described above, the leaflet retention feature 600 is configured to help retain or otherwise secure leaflets 310 to leaflet frame 200. As shown, leaflet retention feature 600 includes a body 602 having a first end 604 and a second end 606. Between the first and second ends 604 and 606, the body 602 of the leaflet retention feature 600 includes a framework defined by one or more longitudinal portions, such as longitudinal portions 608*a*-608*c*, and one or more transverse portions, such as transverse portion 610*a*-610*c*. The framework of the leaflet retention feature 600 is generally configured such that a longitudinal element extends between (or otherwise links together) adjacent transverse elements. Similarly, the framework of the leaflet retention feature 600 is generally configured such that a transverse element extends between (or otherwise links together) adjacent longitudinal elements.

In some examples, the framework of the leaflet retention feature 600 may be configured to include one or more "open cells," such as open cells 612*a*-612*b*, which are cells that are not fully enclosed (or otherwise bordered on all sides) by the longitudinal and transverse portions of the leaflet retention feature 600. For example, as shown in FIG. 19, the leaflet retention feature 600 includes a first open cell 612*a* and a second open cell 612*b*. One or more of these open cells are configured to accommodate the leaflet frame projections 260 therein, as described further below.

As shown, the first open cell 612*a* is defined by a longitudinal portion 608*b* and a plurality of transverse elements 610*a* and 610*b*, where longitudinal portion 608*b* extends between transverse element 610*a* and 610*b*. In some examples, one or more of the longitudinal elements are configured to span across a length of one or more of the leaflet frame projections 260, while one or more of the longitudinal elements are configured to span between adjacently situated leaflet frame projections 260. In some examples, one or more of the transverse elements are configured to span across a width of one of the leaflet frame projections (e.g., from at least a leaflet frame outer surface 202 to at least a leaflet frame inner surface 202). As mentioned above with regard to the various other leaflet retention features, the leaflet retention feature 600 may be configured such that, when coupled with the leaflet frame 200, the leaflet retention feature 600 does not project from a maximum outside profile (e.g., leaflet frame outer surface 203) and/or maximum inside profile (e.g., leaflet frame inner surface 202) of the leaflet frame 200.

The leaflet retention feature 600 can be formed any metal, metal alloy, or polymeric material discussed herein, and can be formed through one or more known chemical etching, laser cutting, micro-molding, stamping, bending or other processes.

The leaflet retention feature 600 is couplable to the leaflet frame 200 of the prosthetic valve 100 in a similar manner to that described above with regard to leaflet retention features 400 and 500. In some examples, coupling the leaflet retention feature 600 with the leaflet frame 200 includes disposing the leaflet retention feature 600 over the leaflet frame projections 260 such that the leaflet frame projections extend through one or more of the open cells of the leaflet retention feature 600. In some examples, the leaflet retention feature 600 may then be advanced along the leaflet frame projections 260 toward the leaflet retention surface 233 from which the leaflet frame projection 260 extends, as similarly discussed above. The leaflet retention feature 600 may be advanced until the leaflet retention feature 600 contacts the leaflet 310, and/or until the leaflet retention feature 600 is advanced to a designated position along the leaflet frame projection 260, and/or until the leaflet retention feature 600 is properly seated within one or more features of the leaflet frame projection 260, and/or until the leaflet retention feature 600 contacts the leaflet 310 and the leaflet 310 contacts the leaflet retention surface 233. In some examples, the leaflet retention feature 600 is advanced along the leaflet frame projections 260 until the leaflet retention feature 600 is properly seated between the leaflet retention surface 233 and a flange extending from an end of the leaflet frame projection 260 (e.g., within relief 261).

Figure 21:
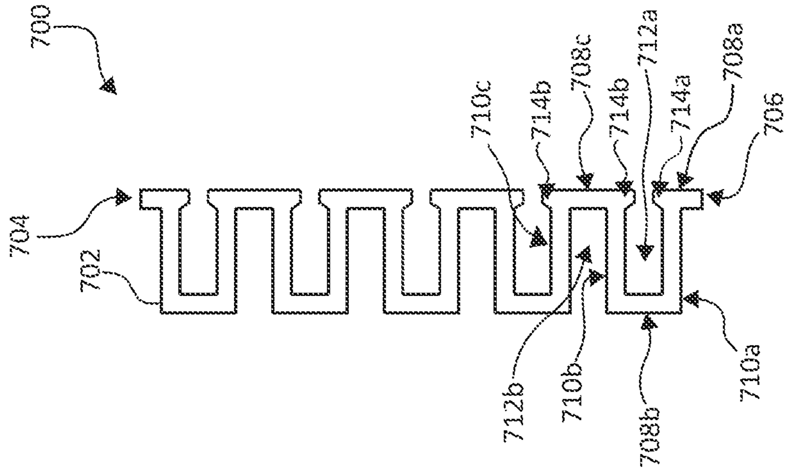
FIG. 21 is a magnified top view of region 21 of FIG. 20 showing the leaflet retention feature coupled to a leaflet frame, according to some embodiments.
Figure 20:
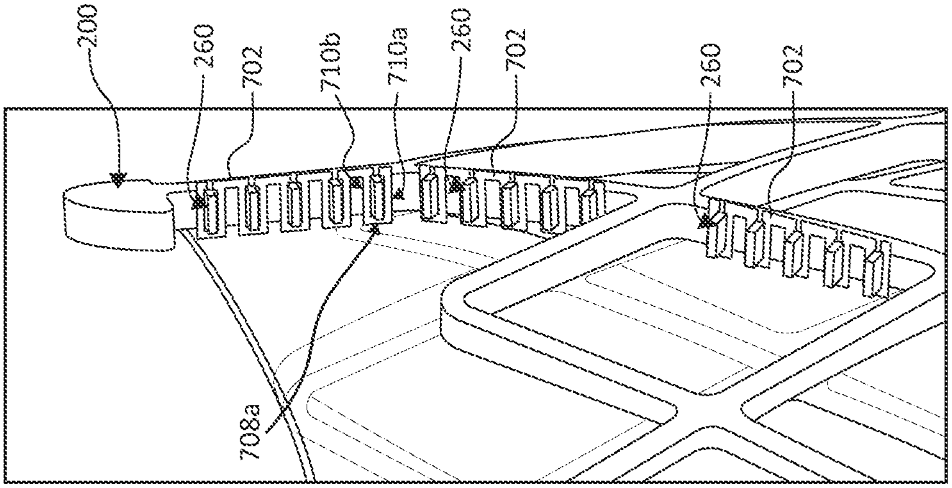
FIG. 20 is an illustration of a leaflet retention feature, according to some embodiments.

FIGS. 20 and 21 provide illustration of a leaflet retention feature 700. FIG. 20 is a is a perspective view of a portion of a leaflet frame 200 with the leaflet retention feature 600 coupled to leaflet frame projections 260 of the leaflet frame 200. As mentioned above, the leaflet frame 200 illustrated in FIG. 20 should not be construed as limiting, and any leaflet frame configuration including a plurality of leaflet frame projections 260 as described herein may be utilized. FIG. 21 provides an example illustration of the leaflet retention feature 700 shown in FIG. 20. Like leaflet retention feature 600 described above, the leaflet retention feature 700 is configured to help retain or otherwise secure leaflets 310 to leaflet frame 200. As shown, leaflet retention feature 700 includes a body 702 having a first end 704 and a second end 706. Between the first and second ends 704 and 706, the body 702 of the leaflet retention feature 700 includes a framework defined by one or more longitudinal portions, such as longitudinal portions 708_a_-708_c_, and one or more transverse portions, such as transverse portion 710_a_-710_c_. The framework of the leaflet retention feature 700 is generally configured such that a longitudinal element extends between (or otherwise links together) adjacent transverse elements. Similarly, the framework of the leaflet retention feature 700 is generally configured such that a transverse element extends between (or otherwise links together) adjacent longitudinal elements.

In some examples, the framework of the leaflet retention feature 700 may be configured to include one or more "open cells," such as open cells 712_a_-712_b_, which are cells that are not fully enclosed (or otherwise bordered on all sides) by the longitudinal and transverse portions of the leaflet retention feature 700. For example, as shown in FIG. 21, the leaflet retention feature 700 includes a first open cell 712_a_ and a second open cell 712_b_. One or more of these open cells are configured to accommodate the leaflet frame projections 260 therein, as described further below.

As shown, the first open cell 712_a_ is defined by a longitudinal portion 708_b_ and a plurality of transverse portions 710_a_ and 710_b_, where longitudinal portion 708_b_ extends between transverse portions 710_a_ and 710_b_. In some examples, one or more of the longitudinal elements are configured to span across a length of one or more of the leaflet frame projections 260, while one or more of the longitudinal elements are configured to span between adjacently situated leaflet frame projections 260. In some examples, one or more of the transverse elements are configured to span across a width of one of the leaflet frame projections (e.g., from at least a leaflet frame outer surface 202 to at least a leaflet frame inner surface 202). As mentioned above with regard to the various other leaflet retention features, the leaflet retention feature 700 may be configured such that, when coupled with the leaflet frame 200, the leaflet retention feature 700 does not project from a maximum outside profile (e.g., leaflet frame outer surface 203) and/or maximum inside profile (e.g., leaflet frame inner surface 202) of the leaflet frame 200.

The leaflet retention feature 700 can be formed any metal, metal alloy, or polymeric material discussed herein, and can be formed through one or more known chemical etching, laser cutting, micro-molding, stamping, bending or other processes.

The leaflet retention feature 700 is couplable to the leaflet frame 200 of the prosthetic valve 100 in a similar manner to that described above with regard to leaflet retention features 400 and 500. In some examples, coupling the leaflet retention feature 700 with the leaflet frame 200 includes disposing the leaflet retention feature 700 over the leaflet frame projections 260 such that the leaflet frame projections extend through one or more of the open cells of the leaflet retention feature 700. In some examples, the leaflet retention feature 700 may then be advanced along the leaflet frame projections 260 toward the leaflet retention surface 233 from which the leaflet frame projection 260 extends, as similarly discussed above. The leaflet retention feature 700 may be advanced until the leaflet retention feature 700 contacts the leaflet 310, and/or until the leaflet retention feature 700 is advanced to a designated position along the leaflet frame projection 260, and/or until the leaflet retention feature 700 is properly seated within one or more features of the leaflet frame projection 260, and/or until the leaflet retention feature 700 contacts the leaflet 310 and the leaflet 310 contacts the leaflet retention surface 233. In some examples, the leaflet retention feature 700 is advanced along the leaflet frame projections 260 until the leaflet retention feature 700 is properly seated between the leaflet retention surface 233 and a flange extending from an end of the leaflet frame projection 260 (e.g., within relief 261).

As shown, however, the leaflet retention feature 700 further includes one or more retaining tabs, such as retaining tabs 714_a_-714_c_, that are configured to help minimize a possibility for the leaflet retention feature 700 to become dislodged from the leaflet frame projections 260. In particular, as shown, the retaining tabs 714_a_-714_c_ are configured to minimize dislodgement of the leaflet retention feature 700 by way of lateral translation (e.g., in a radially inwardly or a radially outwardly direction) of the leaflet retention feature 700 relative to the leaflet frame projections 260. While illustrated in FIGS. 20 and 21 as tabs that project longitudinally (e.g., in a direction of the longitudinal portions 708_a_-708_c_ of the leaflet retention feature 700) relative to the leaflet frame projections 260, it should be appreciated that various alternative configurations are envisioned. For instance, in some examples, one or more retaining tabs may additionally or alternatively project longitudinally from the transverse elements (e.g., 710_a_-710_c_) and engage the leaflet frame projections 260 along the leaflet frame projections 260 between the leaflet frame inner surface 202 and the leaflet frame outer surface 203.

Figure 23:
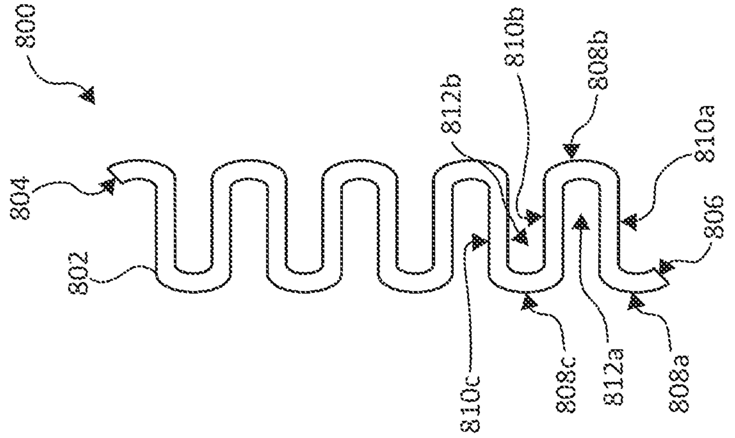
FIG. 23 is a magnified top view of region 23 of FIG. 22 showing the leaflet retention feature coupled to a leaflet frame, according to some embodiments.
Figure 22:
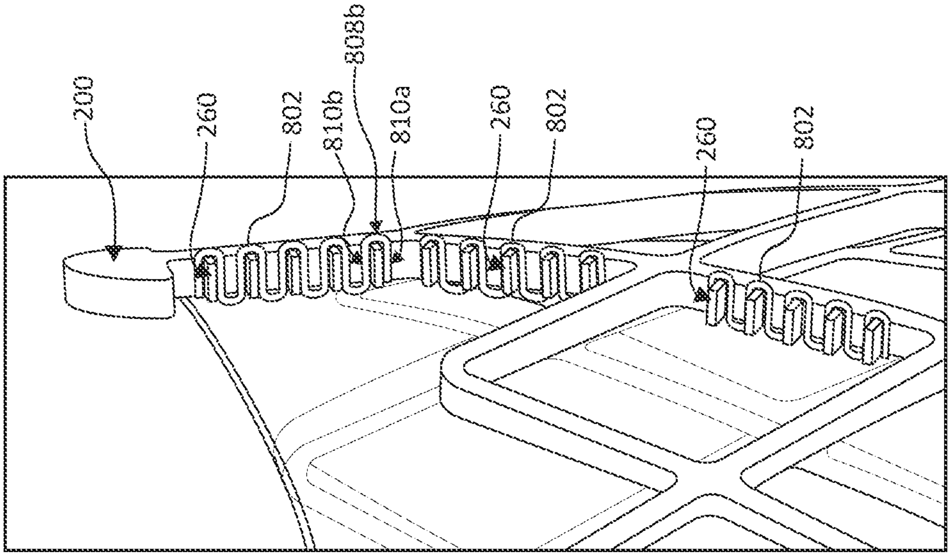
FIG. 22 is an illustration of a leaflet retention feature, according to some embodiments.

FIGS. 22 and 23 provide illustration of a leaflet retention feature 700. FIG. 22 is a is a perspective view of a portion of a leaflet frame 200 with the leaflet retention feature 700 coupled to leaflet frame projections 260 of the leaflet frame 200. As mentioned above, the leaflet frame 200 illustrated in FIG. 22 should not be construed as limiting, and any leaflet frame configuration including a plurality of leaflet frame projections 260 as described herein may be utilized. FIG. 23 provides an example illustration of the leaflet retention feature 700 shown in FIG. 22. Like leaflet retention feature 600 described above, the leaflet retention feature 800 is configured to help retain or otherwise secure leaflets 310 to leaflet frame 200. As shown, leaflet retention feature 800 includes a body 802 having a first end 804 and a second end 806. Between the first and second ends 804 and 806, the body 802 of the leaflet retention feature 800 includes a framework defined by one or more longitudinal portions, such as longitudinal portions 808_a_-808_c_, and one or more transverse portions, such as transverse portion 810_a_-810_c_. Accordingly, framework of leaflet retention feature 800 is similar to the frame work of leaflet retention feature 600. For instance, the framework of the leaflet retention feature 800 includes one or more "open cells," such as open cells 812_a_-812_b_ that are configured to accommodate the leaflet frame projections 260 therein. However, the leaflet retention feature 800 includes smooth transitions between the longitudinal and transvers elements defining the framework. For instance, while the framework of the leaflet retention feature 800 is generally configured such that a longitudinal element (e.g., 808_a_-808_c_) extends between (or otherwise links together) adjacent transverse elements (e.g., 810_a_-810_c_), the longitudinal element (e.g., 808_a_-808_c_) is curved or non-linearly shaped. In some examples, the transverse elements (e.g., 810_a_-810_c_) are curved or non-linearly shaped. The curvatures of the longitudinal elements (e.g., 808_a_-808_c_) and/or the transverse elements (e.g., 810_a_-810_c_) may be concave, convex, or combinations thereof to achieve optimal locking force or force of engagement with the leaflet frame projections (e.g., 260 and/or 1260).

Like the various leaflet retention features illustrated and described above, the leaflet retention feature 800 can be formed any metal, metal alloy, or polymeric material discussed herein, and can be formed through one or more known chemical etching, laser cutting, micro-molding, stamping, bending or other processes.

The leaflet retention feature 800 is also couplable to the leaflet frame 200 of the prosthetic valve 100 in a similar manner to that described above with regard to leaflet retention feature 600. In some examples, the leaflet retention feature 800 may be configured to be transitionable between a preinstalled configuration and an installed configuration, wherein a shape of the leaflet retention feature 800 is different in the installed configuration relative to the preinstalled configuration. For instance, in some examples the leaflet retention feature 800 may be configured such that, in a preinstalled configuration, an arrangement of its open cells (e.g., 812*a*-812*c*), such as a size and shape of its open cell (e.g., 812*a*-812*c*), differs from an arrangement of the leaflet frame projections 260 of the leaflet frame 200.

Figure 24:
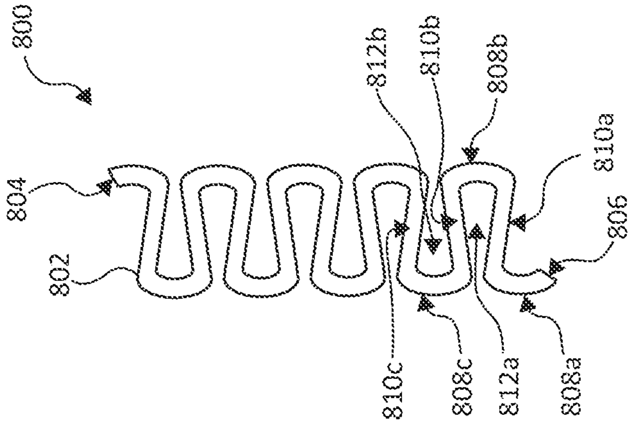
FIG. 24 is an illustration of the leaflet retention feature of FIG. 22 in a preinstalled configuration, according to some embodiments.

For instance, FIG. 24 provides an illustration of the leaflet retention feature 800 in a preinstalled configuration, while each of FIGS. 22 and 23 provides an illustration of the leaflet retention feature 800 in an installed configuration. As shown in comparing FIG. 24 with each of FIGS. 22 and 23, the leaflet retention feature 800 transitions to the installed configuration by deforming to accommodate or otherwise conform to the arrangement of the leaflet frame projections 260. In some examples, in the preinstalled configuration, adjacently situated transverse portions (e.g., 810*a* and 810*b*) may be non-parallel or otherwise angled relative to one another, while in the installed configuration, the leaflet frame projections 260 cause adjacently situated transvers portions (e.g., 810*a* and 810*b*) to become parallel, more parallel, or less angled relative to one another than in the preinstalled configuration. For instance, in comparing FIG. 23 with FIG. 24, it is shown that a shape of the open cells (e.g., 812*a*-812*b*) is different in the installed configuration (FIG. 23) relative to the preinstalled configuration (FIG. 24). In some examples, the longitudinal portions (e.g., 808*a*-808*c*) of the leaflet retention feature 800 may become more severely curved (e.g., curve about a smaller radius) than in the installed configuration. In some examples, these deformations of the leaflet retention feature 800 in the installed configuration causes the leaflet retention feature 800 to store potential energy, which biases one or more of the longitudinal portions (e.g., 808*a*-808*c*) and/or one or more of the transverse portions 810*a*-810*c*) to engage the one or more leaflet frame projections 260 of the leaflet frame 200.

It is to be appreciated that, while not illustrated above, leaflet retention features 600 and 700 may similarly be configured to be similarly oversized such that they are deformed when they are coupled with the leaflet frame 200.

Figure 26:
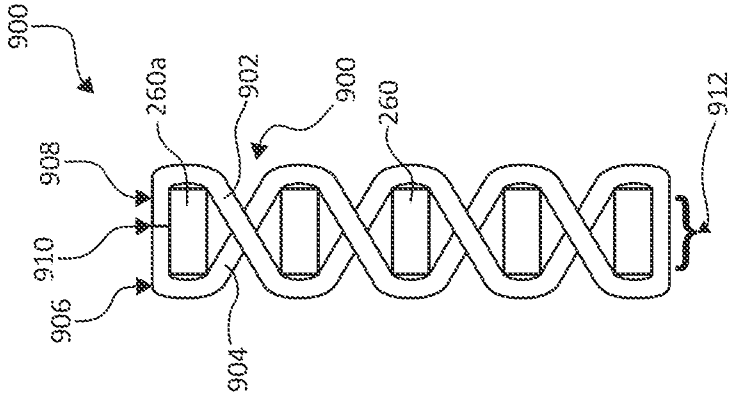
FIG. 26 is a magnified top view of region 26 of FIG. 25 showing the leaflet retention feature coupled to a leaflet frame, according to some embodiments.
Figure 25:
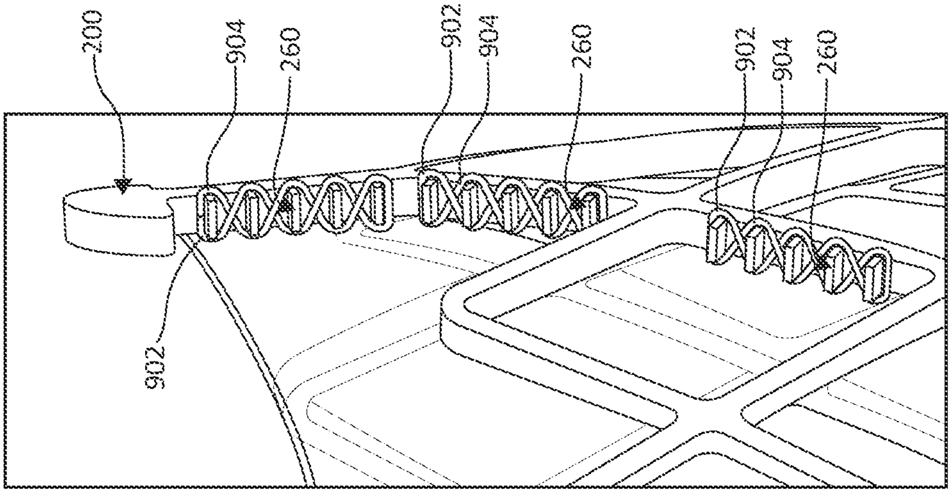
FIG. 25 is an illustration of the leaflet retention feature, according to some embodiments.

FIGS. 25 and 26 provide illustration of a leaflet retention feature 900. FIG. 25 is a is a perspective view of a portion of a leaflet frame 200 with the leaflet retention feature 900 coupled to leaflet frame projections 260 of the leaflet frame 200. As mentioned above, the leaflet frame 200 illustrated in FIG. 25 should not be construed as limiting, and any leaflet frame configuration including a plurality of leaflet frame projections 260 as described herein may be utilized. FIG. 26 provides an example illustration of the leaflet retention feature 900 shown in FIG. 25. In some examples, the leaflet retention feature 900 may include one or more fibers that are interwoven with the leaflet frame projections 260 of the leaflet frame 200. In some examples, a plurality of fibers or wires may be interwoven with the leaflet frame projections 260 of the leaflet frame 200. For example, as shown in FIG. 26, the leaflet retention feature 900 includes a first fiber 902 and a second fiber 904. The first and second fibers 902 and 904 may be the same fiber. That is, in some examples the first and second fibers 902 and 904 form a monolithic or unibody fiber, wherein first fiber 902 corresponds to a first portion of the monolithic fiber routed about or interwoven with the leaflet frame projections 260 in a first direction (e.g., such as a first longitudinal direction) while the second fiber 904 corresponds to a second portion of the monolithic fiber routed about or interwoven with the leaflet frame projections 260 in a second direction (e.g., such as a second longitudinal direction).

In some examples, the first and second directions may be opposing directions. In various examples, ends of the first and second fibers 902 and 904 may be coupled together or otherwise terminated at one another. For instance, in some examples, a first end of the first fiber 902 may be coupled to a first or second end of the second fiber 906. As shown in FIG. 26, an end 906 of the first fiber 902 is coupled with an end 908 of the second fiber 904 at a junction 910. The ends of the fibers may be coupled together according to known mentions, including, but not limited to, welding, tying, suturing, adhering. It is to be appreciated that, although the first and second fibers 902 and 904 are coupled together at junction 910, the fibers 902 and 904 may be one continuous fiber. That is, junction 910 may represent the only joint between fibers 902 and 904. Thus, in some examples, the leaflet retention feature 900 may loop around another leaflet frame projection from a first side of the leaflet frame projection to an opposing side of the leaflet frame projection in a continuous manner (e.g., without a joint) as shown in region 912 of FIG. 26. Thus, it is to be appreciated that the leaflet retention feature 900 may be a continuous element having a first end and a second end, that is interwoven with one or more leaflet frame projections and then coupled to itself, such as at its first and second ends.

In some examples, the leaflet retention feature 900 may optionally include separate independent fibers. For instance, first fiber 902 and second fiber 904, may instead by two independent fibers. In such examples where the leaflet retention feature 900 includes two separate and independent fibers, it will be appreciated that such fibers may be coupled together to form the leaflet retention feature 900 or may optionally be routed through or interwoven with the leaflet frame projections 260 of the leaflet frame 200 without being coupled together. Moreover, while FIGS. 25 and 26 include a leaflet retention feature 900 that includes a first fiber 902 and a second fiber 904, it should be appreciated that the leaflet retention feature 900 may include any number of fibers, such as three (3), four (4), five (5), or more than five (5) fibers, provided that the leaflet retention feature is operable to help secure the leaflet 310 to the leaflet frame 200.

The interwoven fibers may be single strand, multi-strand, braded, woven, constructions and may include an expanded fluoropolymer material made from porous ePTFE, for instance as generally described in U.S. Pat. No. 7,306,729, to Bacino. The expandable fluoropolymer, may comprise PTFE homopolymer. In alternative embodiments, blends of PTFE, expandable modified PTFE and/or expanded copolymers of PTFE may be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

As shown in FIGS. 25 and 26, the leaflet retention feature 900 is interwoven with the leaflet frame projections such that as the fiber (e.g., first fiber 902 and/or second fiber 904)

extends from a first leaflet frame projection to a second leaflet frame projection adjacent the first leaflet frame projection, the fiber traverses a width of the leaflet frame (e.g., from the leaflet frame outer surface 203 to the leaflet frame inner surface 202, or vice versa). Thus, in some examples, a path of the fiber of the leaflet retention feature 900 extends along the leaflet frame inner surface 202 of a first leaflet frame projection 260 toward a second leaflet frame projection 260 adjacent the first leaflet frame projection, and then along the leaflet frame outer surface 203 of the second leaflet frame projection 260, wherein the fiber extends across a width of the leaflet frame 200 (from the leaflet frame inner surface 202 to the leaflet frame outer surface 203) between the first leaflet frame projection 260 and the second leaflet frame projection 260. The path of the fiber of the leaflet retention feature 900 then extends along the leaflet frame outer surface 203 of a second leaflet frame projection 260 toward a third leaflet frame projection 260 adjacent the second leaflet frame projection, and then along the leaflet frame inner surface 202 of the third leaflet frame projection 260, wherein the fiber extends across a width of the leaflet frame 200 (from the leaflet frame outer surface 203 to the leaflet frame inner surface 202) between the second leaflet frame projection 260 and the third leaflet frame projection 260. This zig-zag or alternating pattern is illustrated in FIGS. 25 and 26. It will be appreciated that the fiber of the leaflet retention feature 900 may continue this type of alternating pattern along as many leaflet frame projections 260 as desired.

As shown in FIGS. 25 and 26, where the leaflet retention feature includes a first fiber 902 and a second fiber 904, the second fiber 904 may be routed along a path that opposes the path of the first fiber 902. For instance, where the first fiber 902 extends along the leaflet frame inner surface 202 of a first leaflet frame projection 260 toward a second leaflet frame projection 260 adjacent the first leaflet frame projection, and then along the leaflet frame outer surface 203 of the second leaflet frame projection 260, the second fiber 904 may conversely extend along the leaflet frame outer surface 203 of the first leaflet frame projection 260 toward the second leaflet frame projection 260 adjacent the first leaflet frame projection, and then along the leaflet frame inner surface 202 of the second leaflet frame projection 260. In such an example, as shown in FIGS. 25 and 26, the first and second fibers cross one another in the region between adjacently situated leaflet frame projections 260. In some examples, the first fiber 902 crosses above the second fiber 904 in such regions, such that the second fiber 904 is situated between the first fiber 902 and the leaflet 310, while in other examples the second fiber 904 crosses above the first fiber 902 in such regions, such that the first fiber 902 is situated between the second fiber 904 and the leaflet 310. In some examples, the leaflet retention feature 900 may be routed such that the first fiber 902 always extends above the second fiber 904 in such regions (or vice versa). For instance, as shown in FIGS. 25 and 26, the first fiber 902 always crosses above the second fiber 904. In some examples, the leaflet retention feature 900 may be alternatively routed such that the first and second fibers 902 and 904 cross over one another in an alternating manner or pattern. In some examples, such an alternating pattern may be repetitious or may be random. In some example, the first and second fibers 902 and 904 of the leaflet retention feature 900 may be twisted or knotted together in their regions of crossover to provide redundancy to the system in the event the first and/or second fibers 902 and 904 fail (e.g., tear, split, and/or separate) in one or more regions of the leaflet frame 200.

While the leaflet retention feature 900 described above includes one or more fibers, it is to be appreciated that the leaflet retention feature 900 may additionally or alternatively include one or more wires, such as one or more wires formed of known suture material, nitinol, stainless steel, or other biocompatible materials.

In some examples, a cross-sectional dimension (e.g., a height or a diameter) of any of the various the leaflet retention features (e.g., 400, 500, 600, 700, 800, 900) illustrated and described herein may exceed a distance between the leaflet 310 and the flange of the leaflet frame projection 260, such that, when the leaflet retention feature is positioned between the leaflet 310 and the flange of the leaflet frame projection 260, the leaflet retention feature is applies a normal force to the leaflet, thereby compressing the portion of the leaflet 310 situated between the leaflet frame 200 and the leaflet retention member. In some examples, a configuration that includes compressing a portion of the leaflet 310 helps mitigate or minimize abrasion wear of the leaflet 310 under normal operating conditions. It is to be appreciated that, in some other examples, a distance between the leaflet 310 and the flange of the leaflet frame projection 260 may exceed or be substantially equal to the cross-sectional dimension (e.g., the height or the diameter) of the leaflet retention feature. It should also be appreciated that the cross section of the leaflet retention feature may exhibit virtually any geometry, including circular, ovular, square, rectangular, polygonal, or other suitable geometries. Additionally or alternatively, in some example, the leaflet retention feature may be configured such that it is more deformable than the leaflet 310. In such examples, the leaflet retention feature is thus configured to deform more than the leaflet 310 under similar loading conditions. Similarly, in such examples, a leaflet retention feature exhibiting a larger cross-sectional dimension than the distance between the leaflet 310 and the flange of the leaflet frame projection 260, will deform to a profile that is consistent with the leaflet retention feature being situated between the leaflet 310 and the flange of the leaflet frame projection 260 (e.g., a circular cross-sectional profile deforming to an ovular cross-sectional profile) without causing or requiring a substantial deformation of the leaflet situated between the leaflet retention feature and the leaflet frame.

In various examples, the leaflet frame 200 with the leaflets 310 and the leaflet retention feature (e.g., 400, 500, 600, 700, 800, 900) may be subjected to one or more molding processes where a material is applied to the leaflet frame to cover at least those regions where the leaflet retention feature is present. For instance, a jacket of material (see, e.g., jacket 300 described further below) may be applied over one or more leaflet frame projections 260 and/or the leaflet retention feature. The jacket may be formed of at least one of Polyether ether ketone (PEEK), expanded Polytetrafluoroethylene (ePTFE), Fluorinated ethylene propylene (FEP), copolymers of tetrafluoroethylene (TFE) and perfluoromethyl vinyl ether (PMVE) (TFE-PMVE copolymer), urethanes, polyimides, thermoplastics, thermosets, nylon, or any other biocompatible material. In some examples, the jacket of overmolded material may be applied to the leaflet frame 200, such as via an injection molding process, a heat and/or pressure molding process, one or more dip coating processes, one or more spray coating processes, and other known methods, and combinations thereof.

Figure 27A:
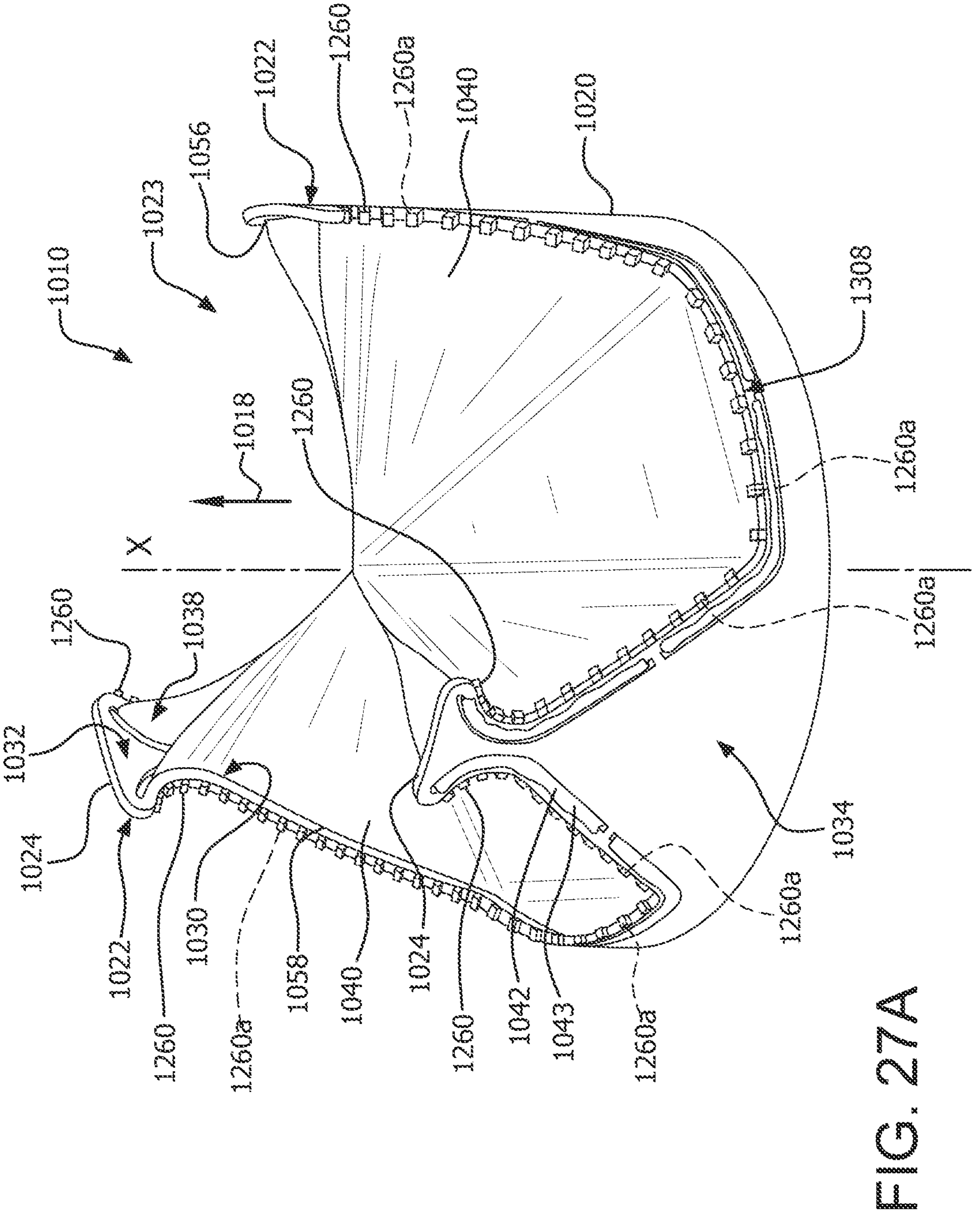
FIG. 27A is a perspective view of a closed prosthetic valve that includes a frame that supports leaflets having adjacent support attachment regions of the commissure post that diverge from a location away from a commissure post tip in an outflow direction towards the commissure post tip, according to some embodiments.
Figure 27B:
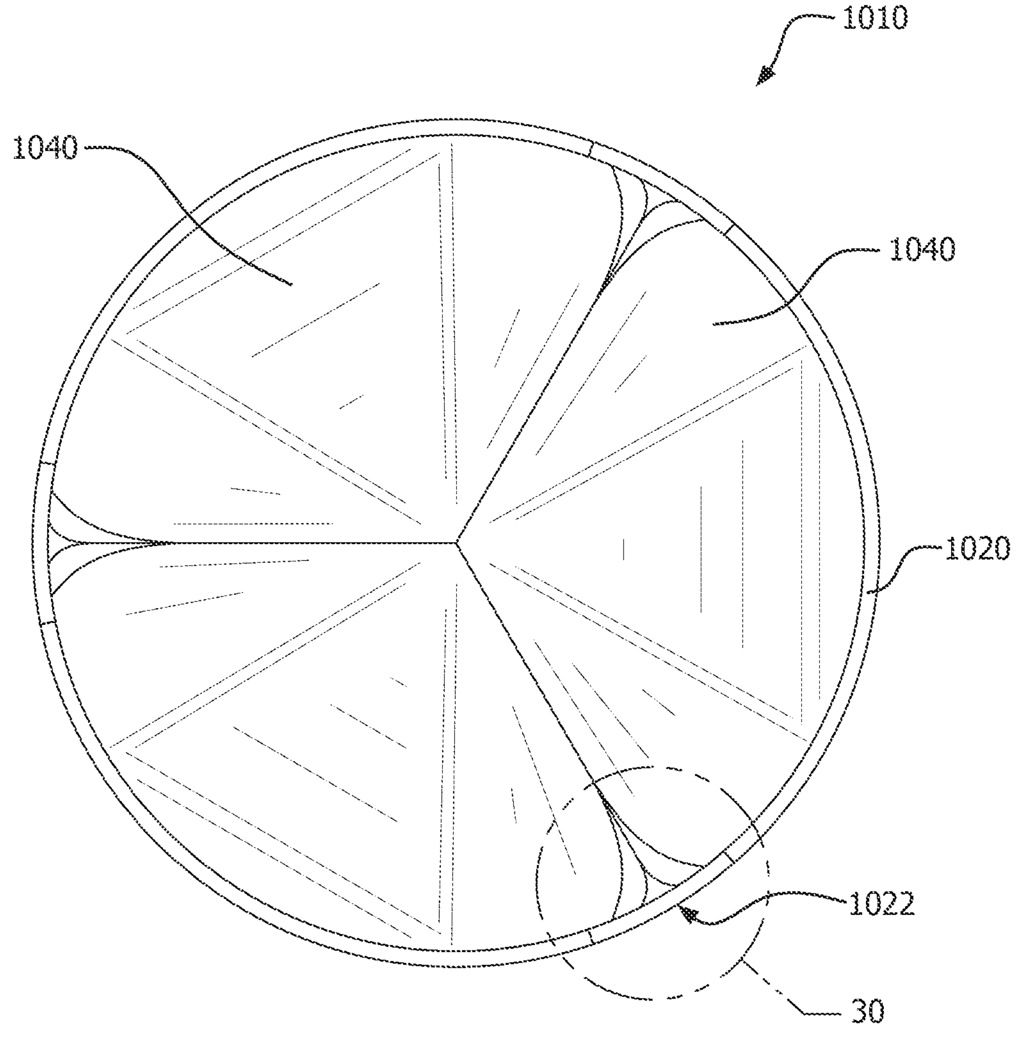
FIG. 27B is an axial view of the prosthetic valve of FIG. 1A in the closed position.
Figure 27C:
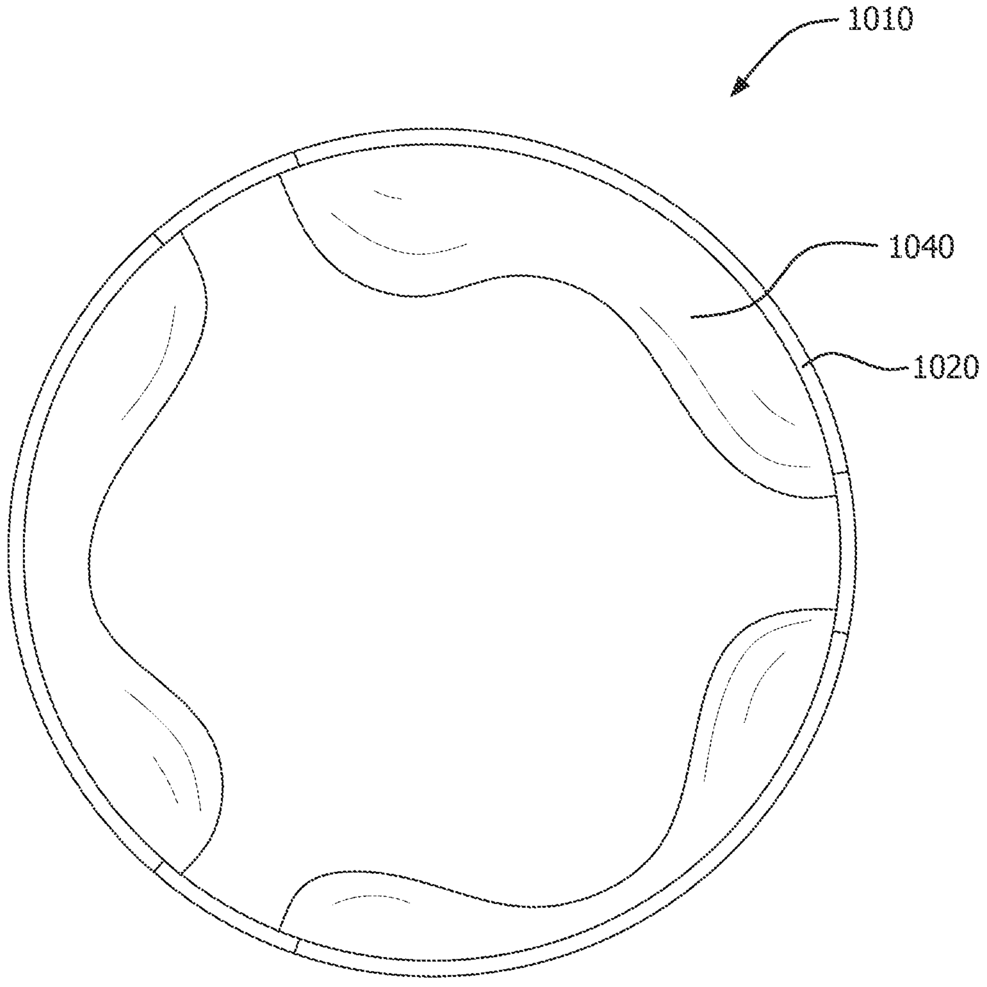
FIG. 27C is an axial view of the prosthetic valve of FIG. 1A in an open position.
Figure 27E:
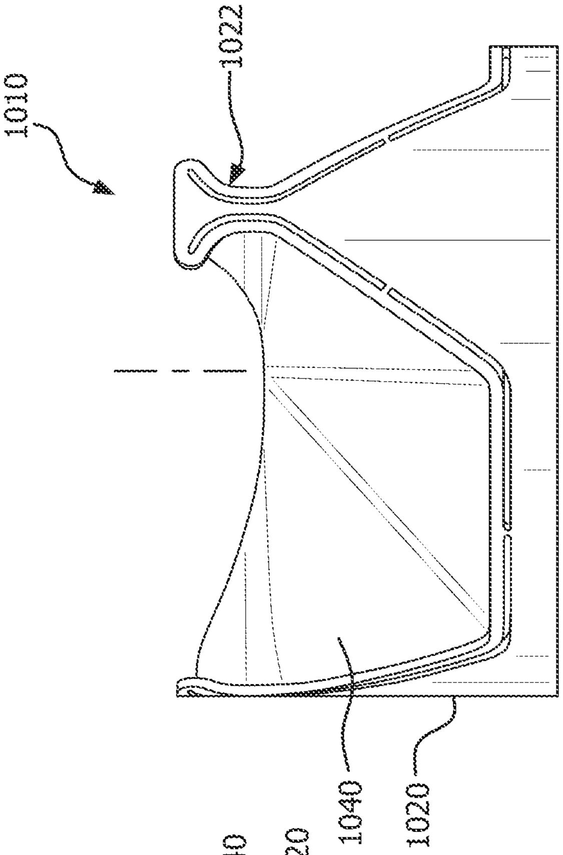
FIG. 27E is another side view of the prosthetic valve of FIG. 1A.
Figure 27D:
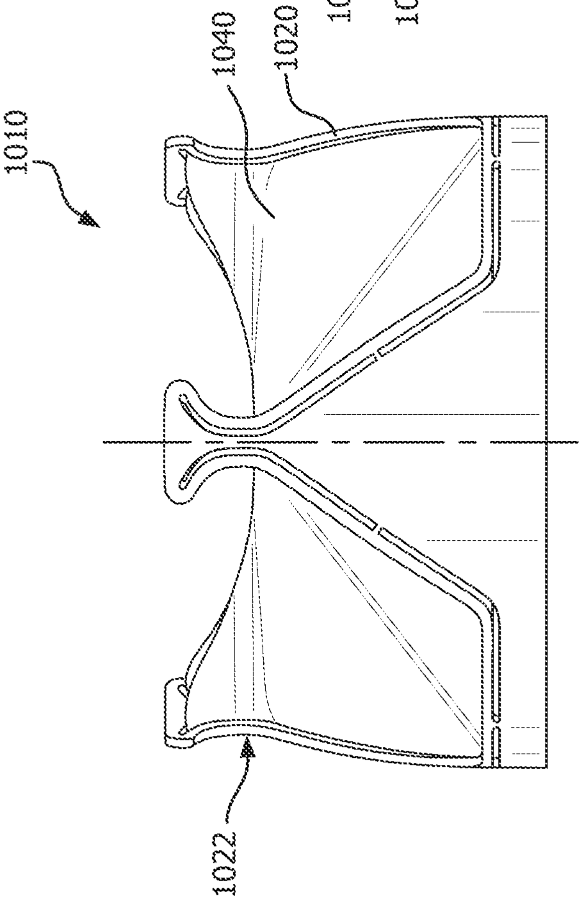
FIG. 27D is a side view of the prosthetic valve of FIG. 1A.

Prosthetic valve leaflets detaching from a support structure, such as the leaflet frame, constitute a high risk to a patient into which it is placed. One factor contributing to leaflet detachment can be peak stress in the leaflet at the commissure region when the prosthetic valve is closed and under fluid backpressure. In some examples, leaflet detachment and stress concentration issues may be addressed by changing the geometry of the upper most portion of adjacent commissure attachment regions on the support structure from being non-divergent to being divergent in the outflow direction from a location away from the commissure post tip. In particular, by employing adjacent, diverging leaflet attachment regions, a beneficial overall stress pattern may be achieved. Thus, it is to be appreciated that the geometry of the leaflet at or proximate the commissure post (e.g., variations from parallel to divergent) has an effect on the stress profile in the leaflet during the operation (including while the leaflet is in the closed and resisting reverse flow), suitable for a particular purpose In some examples, employing adjacent, diverging leaflet attachment regions, provides means by which to preserve, if not shorten, prosthetic valve height while reducing the peak commissure stress in the leaflet at the commissure post without altering the leaflet material properties. FIGS. 27A-35 show a commissure attachment region variation and associated leaflet closing profile at the outflow end that can be employed in any of the embodiments and examples previously described herein. FIGS. 27A and 27B are perspective and axial views, respectively, and FIGS. 27D and 27E are side views of a closed prosthetic valve 1010 that includes a leaflet frame 1020 that couples with and supports a plurality of leaflets 1040 having adjacent support attachment regions 1030 (which may correspond to a modified version of the slots 216 and 217, discussed above) of the commissure post 1022 (which may correspond to commissure posts 210, discussed above) that diverge from a location away from a commissure post tip 1024 (which may correspond to commissure tips 221, discussed above) in an outflow direction 1018 towards the commissure post tip 1024, in accordance with an embodiment. FIG. 27C is an example illustration of the prosthetic valve 1010 during an opening of the prosthetic valve 100. It is to be appreciated that FIG. 27C is for the purpose of illustrating one potential opening configuration of the prosthetic valve 100, and is therefore not intended to be limiting. The closed prosthetic valve 1010 presents when the outflow pressure downstream of the prosthetic valve 1010 is greater than the inflow pressure, wherein the leaflets 1040 close to restrict regurgitate flow through the prosthetic valve 1010. It is to be appreciated that the leaflet frame projections 1260 and 1260*a* shown in FIG. 27A have been removed from FIGS. 27B-27E for clarity purposes.

Figure 28A:
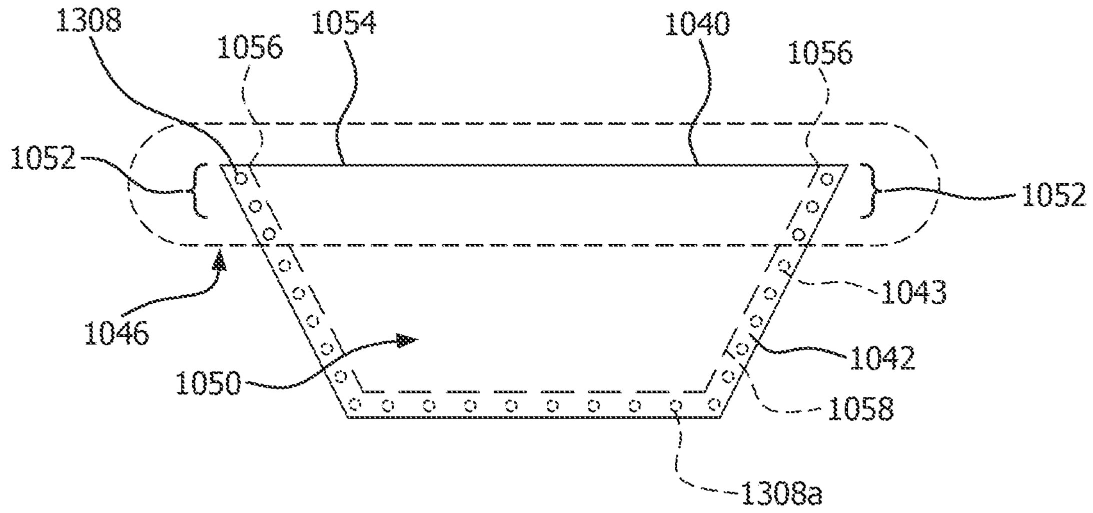
FIG. 28A is a plan view of a leaflet used in the prosthetic valve of FIG. 1A, according to some embodiments.
Figure 28B:
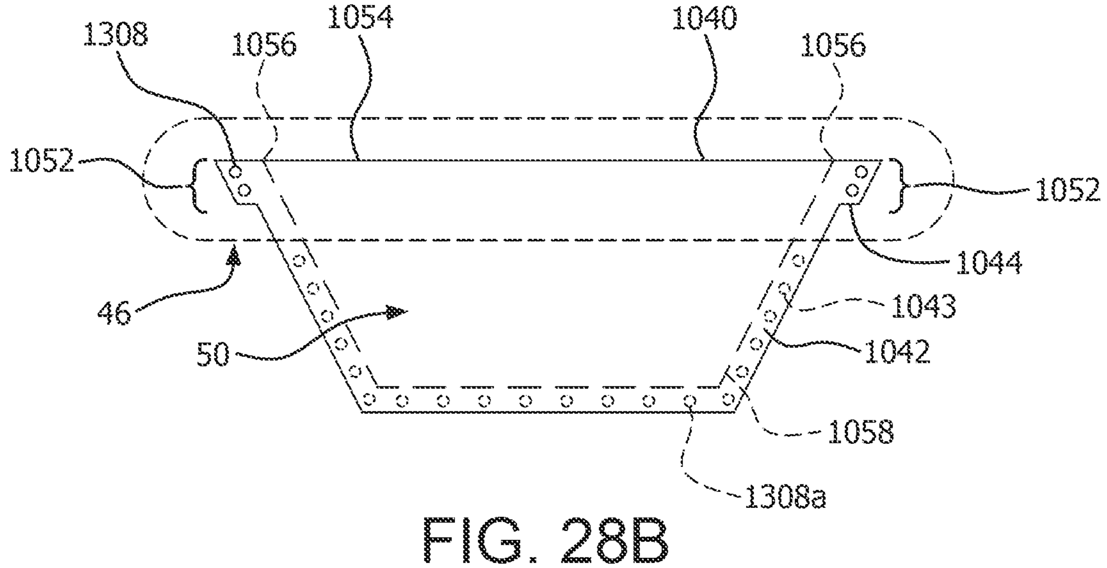
FIG. 28B is a plan view of a leaflet used in the prosthetic valve of FIG. 1A, in accordance with another embodiment.

FIGS. 28A and 28B are plan views of various configurations of leaflets 1040 (which may correspond to leaflets 310, discussed above) that may be used in the prosthetic valve 1010. Leaflets 1040 may have a shape similar to the shape of leaflets 310, in some examples. FIG. 28A shows a leaflet 1040 having a cusp 1050, free edge 1054, and commissure regions 1052. The free edge 1054 extends to two termini 1056. In this embodiment, a (dashed) fold line 1058 defines an outer margin 1042 of the cusp 1050 and commissure regions 1052 that is used to secure the leaflet 1040 to the leaflet frame 1020 as shown in FIG. 27A. A free edge region 1046 is that location of the leaflet 1040 including and adjacent to the leaflet free edge 1054. As will be clear from the discussion below, the outer margin 1042 of each leaflet 1040 is coupled to the frame, and the free edge 1054 of the leaflet 1040 extends across a cylindrical region defined by the leaflet frame 1020, as shown in FIG. 27A, and is generally free to move in that region. In various examples, leaflets 1040 may include one or more leaflet apertures 1308 (which may correspond to leaflet apertures 308, discussed above) along commissure regions 1052 that are configured to interface with the one or more leaflet frame projections 1260. As shown in FIGS. 28A and 28B, leaflets 1040 may optionally include one or more leaflet apertures 1308*a* (which may correspond to leaflet apertures 308, discussed above) along those portions of the leaflet 1040 extending between commissure regions 1052, which are configured to interface with the one or more leaflet frame projections 1260*a*. The interface between the leaflet apertures 1308 and the leaflet frame projections 1260, and/or between the leaflet apertures 1308*a* and leaflet frame projections 1260*a* help facilitate coupling of the leaflet 1040 to the leaflet frame 1020 as discussed above.

FIG. 28B shows a leaflet 1040 that is substantially the same as the leaflet of FIG. 28A, and thus like elements are given the same element numbers. The leaflet 1040 includes a pair of commissure tabs 1044 in the commissure regions 1052. The commissure tabs 1044 are used to assist in coupling each of the leaflets 1040 to the commissure posts of the frame and/or to adjacent commissure tabs 1044 of adjacent leaflets 1040, among other things.

In the embodiment shown in FIG. 27A and FIGS. 28A-28B, the fold line 1058 of the leaflet 1040 and corresponding support attachment region 1030 of the leaflet frame 1020 has an outline that is substantially that of an isosceles trapezoid when viewed as a flat profile, though other shapes are contemplated, as discussed above (e.g., shape of leaflet 310 shown in FIG. 7A). The leaflet frame 1020 comprises a support attachment region 1030 that has substantially the outline of three sides of an isosceles trapezoid.

The fold line 1058 may define an outline predetermined for a particular purpose. In accordance with another embodiment, the outline of the fold line 1058 of the leaflet 1040 and corresponding support attachment region 1030 of the leaflet frame 1020 is substantially that of a parabola.

Figure 29:
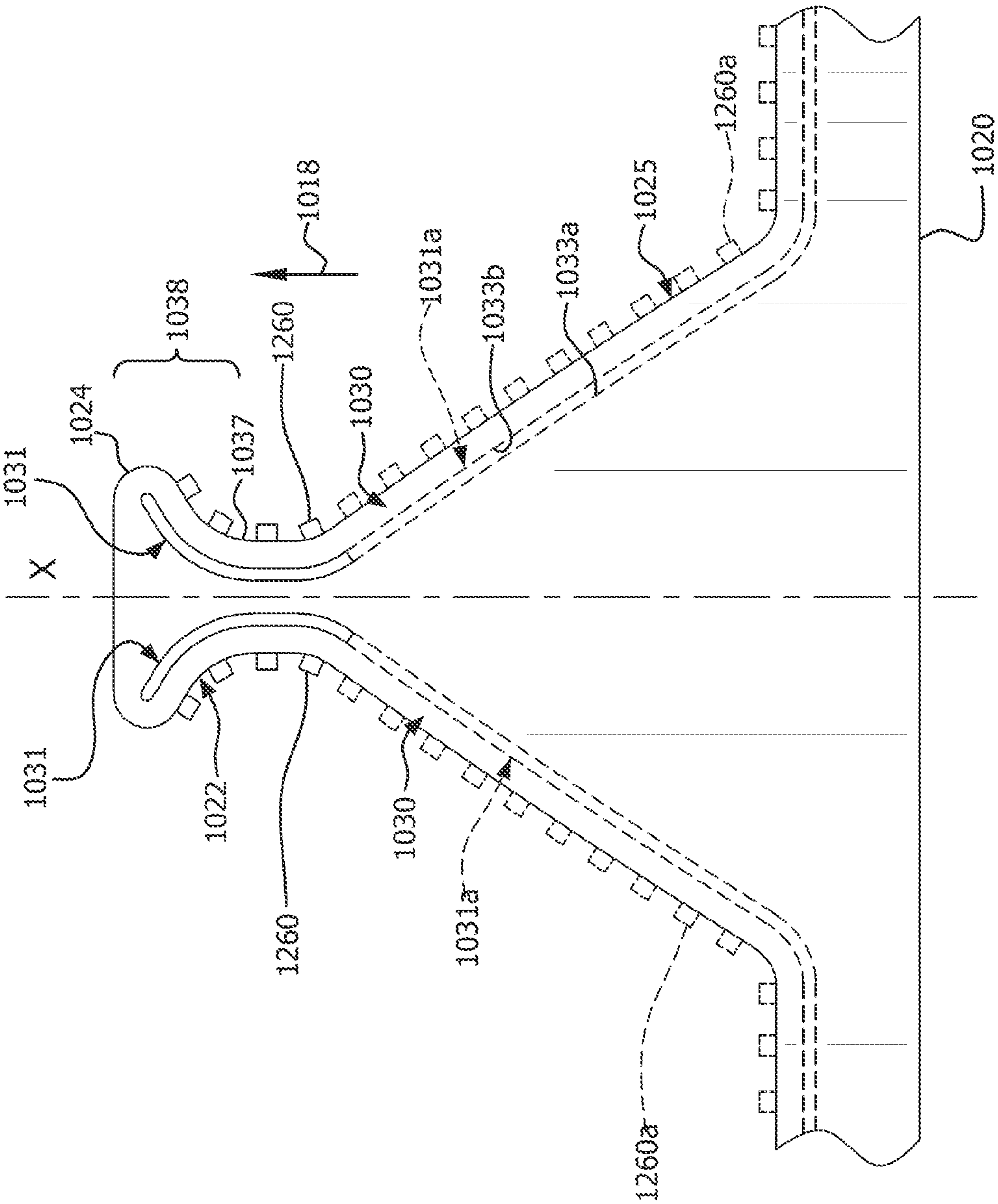
FIG. 29 is a side view of a portion of the frame of the prosthetic valve of the embodiment of FIG. 1A.

FIG. 29 is a side view of a leaflet frame 1020 in accordance with the embodiment of FIG. 27A. The leaflet frame 1020 defines a plurality of commissure posts 1022 operable to couple with a commissure region 1052 of the leaflet 1040, as shown in FIGS. 28A and 28B. The leaflet frame 1020 further defines a base portion 1025 operable to couple with a cusp 1050 of the leaflet 1040, as shown in FIGS. 28A and 28B, as will be described below. A plurality of leaflet frame projections 1260 are shown projecting from the commissure post 1022. The leaflet frame projections 1260 correspond with the leaflet frame projections 260 described and referred to herein. A plurality of leaflet frame projections 1260*a* are also shown in broken lines projecting from the leaflet frame 1020 to illustrate that, in some examples, the leaflets (e.g., 1040 and 310) described and referred to herein may be coupled to the leaflet frame 1020 via one or more leaflet frame projections 1260 along one or more of the commissure posts 1022, and/or one or more leaflet frame projections 1260*a* along one or more non-commissure regions (e.g., regions between adjacent commissure posts, such as base portion 1025) of the leaflet frame 1020.

Figure 30:
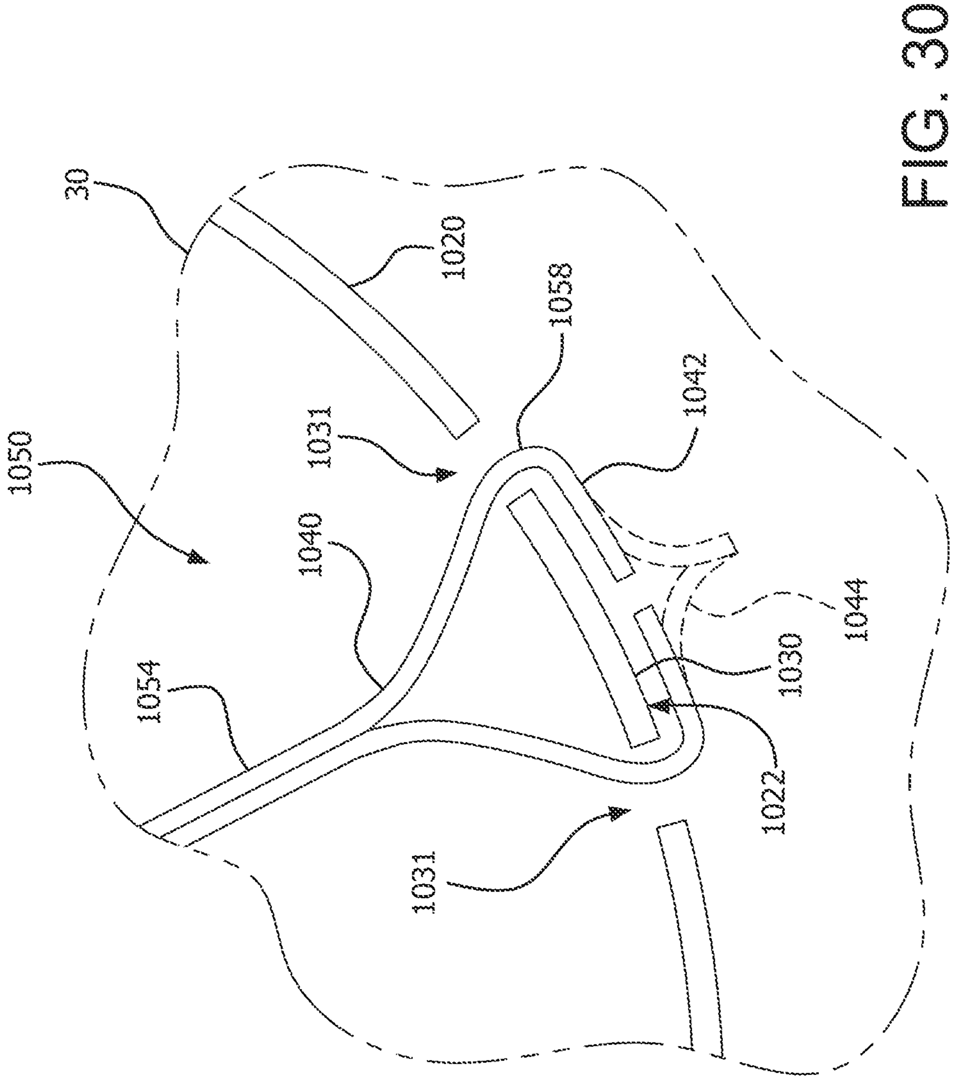
FIG. 30 is a detailed view of region 4 of the embodiment of FIG. 1B.

Between the commissure posts 1022 is a support attachment region 1030 that is operable to support the leaflet 1040 along at least the (dashed) fold line 1058, which defines an outer margin 1042 of the cusp 1050 of the leaflet 1040 when coupled to the leaflet frame 1020, as shown in FIG. 30. In various examples, the support attachment region 1030 may include a plurality of leaflet frame projections 1260*a* (which may correspond with leaflet frame projections 260 illustrated and described above), and/or may optionally include one or more slots 1031*a* (shown in broken line) through which the leaflet (e.g., 1040 or 310) may extend. FIG. 30 is a cross-sectional view of the cut line—30-30 of FIG. 29 showing the commissure post 1022 and support attachment region 1030.

FIG. 30 provides an illustration similar to FIGS. 2F-2I where the leaflet 1040 is wrapped about one or more portions of the leaflet frame 1020. As shown in FIG. 30, the outer margin 1042 of the leaflet 1040 extends along the support attachment region 1030 of leaflet frame 1020 The cusp 1050 is folded along the fold line 1058, as shown. In some examples, the outer margin 1042 may be coupled to the leaflet frame 1020 along the support attachment region 1030. While not shown in FIG. 30, it should be appreciated that the leaflet 1040 may be secured to the leaflet frame 1020 via one or more leaflet frame projections (e.g., 1260, 260) in accordance with FIGS. 21-2F, for example. Thus, while the leaflet 1040 is not illustrated in FIG. 30 as being disposed over any leaflet frame projections 1260, it should be appreciated that the leaflet 1040 may be coupled with one or more leaflet frame projections 1260 in the region of the commissure post 1022 shown in FIG. 30, in accordance with the discussion above.

With continued reference to FIG. 30, each leaflet 1040 is received within a respective slot 1031 defined in the commissure post 1022 of the leaflet frame 1020 with the commissure regions 1052 of the leaflet 1040 extending through the slot 1031 of the commissure post 1022. While the slot 1031 is shown in FIG. 29 as extending along the leaflet frame 1020 including along those portions of the leaflet frame 1020 corresponding to the leaflet frame second edge 206 described above (e.g., the region between the commissure posts 1022 and 210), it is to be appreciated that the slot 1031 may be present in the region of the commissure post 1022 without also being present in other regions of the leaflet frame 1020 (see, e.g., FIG. 2C). Continuing with FIG. 29, each outer margin 1042 of the leaflet 1040 may be “inserted” or otherwise extended through the slot 1031 of the leaflet frame 1020. An attachment means, including but not limited to one or more leaflet frame projections 1260, may operate to couple the outer margin 1042 of the leaflet 1040 to the leaflet frame 1020. Other suitable means of attachment include, but are not limited to, suturing, adhering or bonding, welding, wrapping, and coupling the leaflet to itself. For example, the commissure regions 1052, shown in FIG. 28A, of two adjacent leaflets 1040 may be coupled to a frame outer side 1034 of the leaflet frame 1020 and/or to each other, as shown in FIG. 30 in dashed lines, or some other means, so as to restrict the commissure regions 1052 from pulling back through the respective slot 1031 at the commissure post 1022. Moreover, while illustrated as being wrapped at least partially around a portion of the leaflet frame 1020, in some examples, one or more regions of the leaflet 1040, including all of or less than all of commissure region 1052, may be coupled to the leaflet frame 1020 without being first wrapped about the leaflet frame 1020. For instance, the leaflet 1040 may be coupled to one more of those portions of the leaflet frame 1020 that define the slot 1031 (e.g., wall or surface) without first being wrapped around a portion of the leaflet frame 1020 (e.g., without folding the leaflet 1040 along fold line 1058). Additionally, in some examples, one or more portions of the leaflet frame 1020 defining the slot 1031 may include one or more leaflet frame projections 1260 that project into the slot 1031 and over which one or more of the leaflet apertures 1308 of the leaflet 1040 are disposed. Various wrapping configurations are illustrated and described above with respect to FIGS. 2F-2I. A non-wrapping configuration is shown in FIG. 1B in the region of the leaflet frame 200 below commissure post 210.

In various examples, the commissure region 1052 of the leaflet 1040 may be coupled to the commissure post 1022 of the leaflet frame 1020 about one of the diverging support attachment regions 1030. The commissure post 1022 shown in FIG. 29 defines a diverging region 1038 having two slots 1031 that define respective support attachment regions 1030 that diverge from a location away from the commissure post tip 1024 in the outflow direction 1018 towards the commissure post tip 1024 (see, also, FIG. 27A), such that the two slots 1031 of a respective commissure post 1022 diverge from one another in the outflow direction in the region of the commissure post tip 1024. Thus, when coupled with the leaflet frame 1020, each of two commissure regions 1052 of respective leaflets 1040 will diverge from a location away from the commissure post tip 1024 in the outflow direction 18, as shown in FIG. 27A. The commissure region 1052 of the respective leaflet 1040 is coupled to the commissure post 1022 of the leaflet frame 1020 about one of the respective diverging support attachment regions 1030, such as, for example, beginning at the leaflet fold line 58.

Referring again to FIGS. 27A and 28A, a plurality of leaflets 1040 each define two termini 1056 at an intersection of a leaflet free edge 1054 and a leaflet attachment region 1043. The leaflet attachment region 1043 of each leaflet 1040 being coupled to the leaflet frame 1020 at the support attachment region 1030 such that the leaflet attachment region 1043 adjacent the terminus 1056 of two adjacent leaflets 1040 diverge relative to each other from a location away from the terminus 1056 to the terminus 1056.

Figure 31:
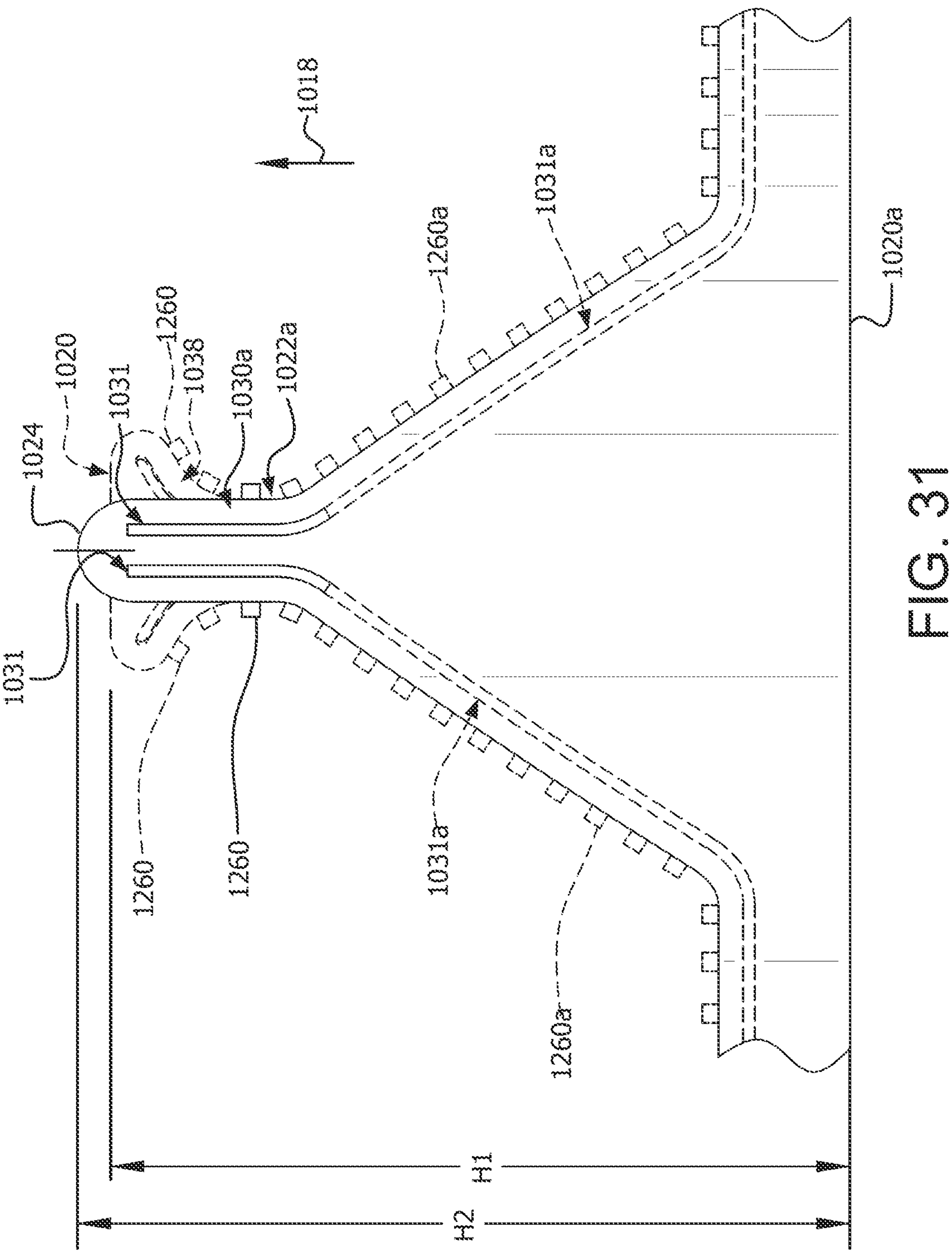
FIG. 31 is a side view of a portion of a frame of a prosthetic valve wherein adjacent support attachment regions of the commissure post are parallel for comparison purposes to the embodiment of FIG. 3, which is superimposed thereon in dashed line.

By way of comparison, FIG. 31 is a side view of a leaflet frame 1020*a* that shows a commissure post 1022*a* that defines two slots 1031 that define respective support attachment regions 1030*a* that are aligned with and parallel to the axis X of the leaflet frame 1020*a* at the commissure post 1022*a*; in other words, this is an example wherein the support attachment regions 1030*a* do not diverge from a location away from the commissure post tip 1024 in the outflow direction 1018 towards the commissure post tip 1024.

When coupled to a leaflet frame 1020, the commissure regions 1052 of each leaflet 1040 are under tension during dynamic motion of the prosthetic valve 1010 and when pressurized when the prosthetic valve 1010 is closed and there is downstream pressure against the closed leaflets 1040. It has been found that non-diverging support attachment regions 1030*a* at the commissure post 1022*a* corresponding to the leaflet fold line 1058 at the commissure region 1052 is an area of maximal stress when the leaflet 1040 is in the closed position and restricting reverse flow. In particular, the maximal stress is at the region of the terminus 1056.

As shown in the embodiments of FIGS. 27A-30, each of the respective commissure regions 1052 of the respective leaflets 1040 are coupled to the respective commissure post 1022 along one of the respective diverging support attachment regions 1030. As such, when the leaflets are in the closed position under the influence of downstream fluid pressure of a closed valve, each leaflet 1040 is placed in stress with the maximal stress at the commissure regions 1052, but in contrast with the embodiment of FIG. 31, the location of maximal stress is away from the terminus 1056, distributed over a larger area and at a reduced magnitude.

Figure 32A:
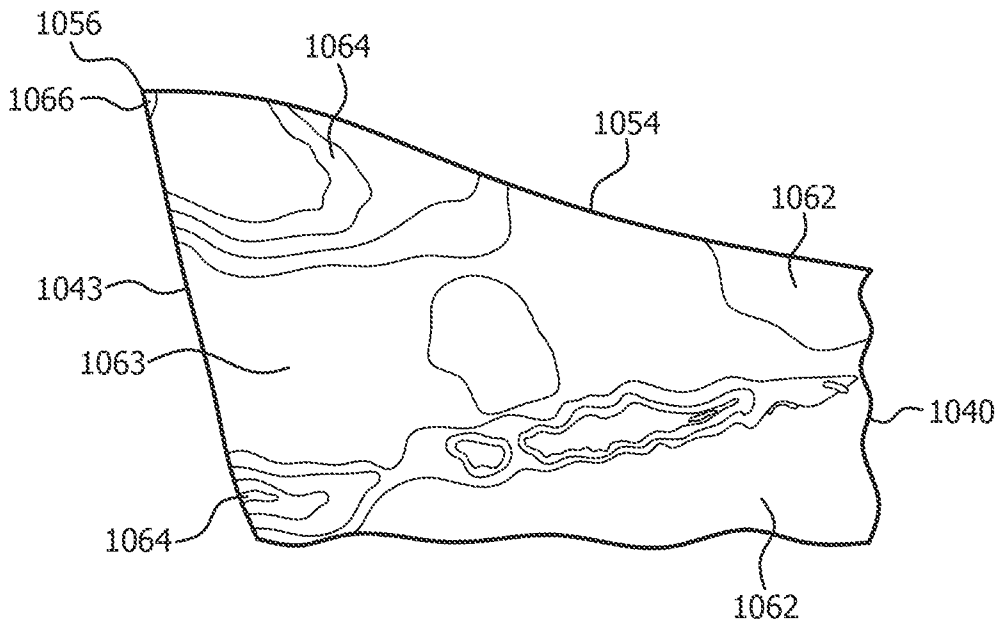
FIG. 32A illustrates the stress distribution for the leaflet coupled to the frame of the embodiment of FIG. 5 with non-diverging support attachment regions, produced by performing a finite element analysis.
Figure 32B:
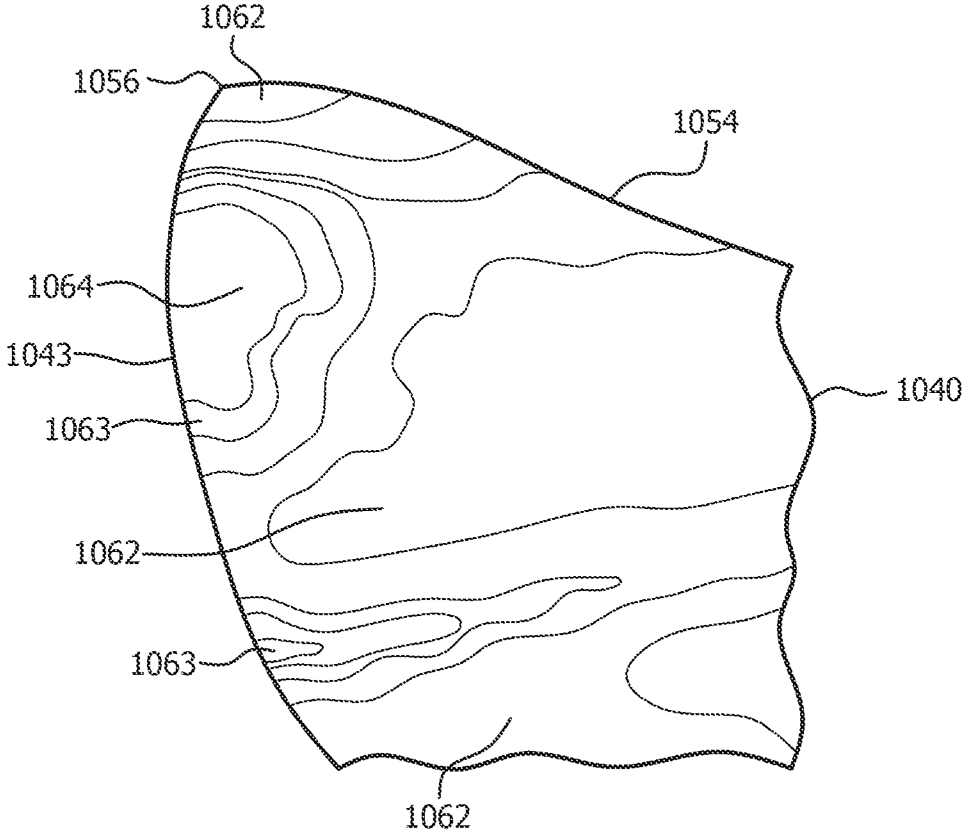
FIG. 32B illustrates the stress distribution for the leaflet coupled to the frame of the embodiment of FIG. 3 with diverging support attachment regions, produced by performing a finite element analysis.

FIG. 32A provides a von Mises stress distribution within the commissure region of the leaflet 1040 of the embodiment of FIG. 31 that is coupled to a non-diverging leaflet attachment region 1043, corresponding to a support attachment region 1030*a*, produced by performing a finite element analysis. FIG. 32B provides the von Mises stress distribution within the commissure region of the leaflet 1040 of the embodiment of FIG. 27A, shown in dashed line in FIG. 31, that is coupled to a diverging leaflet attachment region 1043, produced by performing a finite element analysis. The commissure region of the respective leaflets 1040 are shown having a free edge 1054 and a leaflet attachment region 1043 intersecting at a terminus 1056. The von Mises stress distributions shown are based on the leaflet 1040 experiencing a peak closing pressure of about 135 mmHg. Stress contour 1066 represents a stress value of about 2.85e+03 psi, stress contour 1064 of about 1.67e+03 psi, stress contour 1063 of about 1.10e+03 psi, and stress contour 1062 of about 0.67e+03 psi. As can be seen from FIG. 32A, the embodiment with a non-diverging leaflet attachment region 1043, the location of maximum loaded stress at the leaflet attachment region 1043 is located at the terminus 1056, stress contour 1066.

In the present embodiments, because the diverging outline of the support attachment regions at the commissure post is predetermined, the stresses along each leaflet attachment region can be calculated and an outline of the support attachment region can be selected which distributes the stress away from the terminus of the leaflet and reduces the stress at the terminus. In accordance with some embodiments, a stress force vector within the leaflet along a diverging region may be reduced relative to a non-diverging frame attachment resulting in a reduction of 41% of peak stress in the leaflet adjacent the free edge at the frame for a given frame length. In another embodiment, the stress within the leaflet along the diverging region may be reduced more than 40% relative to a non-diverging attachment when exposed to peak closing pressures of about 135 mmHg in the leaflet adjacent the free edge at the support structure for a given support structure length. As shown in FIG. 32B, the embodiment with a diverging leaflet attachment region 1043, also as shown in FIG. 27A and in dashed line in FIG. 31, corresponding to a support attachment region 1030, the maximum stress is located away from the terminus 1056, stress contour 1062, at a location on the leaflet attachment region 1043, stress contour 1064. The stress in the leaflet 1040 at the leaflet attachment region 1043 is in general more uniformly distributed as compared with the embodiment of FIG. 32A, and has a maximum stress, stress contour 1064, of about 40% less than the maximum stress encountered in the embodiment of FIG. 32A. This demonstrates that the location of maximum loaded stress can be moved to a predetermined and more favorable location and the magnitude and distribution of stress that a given region of the leaflet 1040 experiences can be changed by changing the geometry of the support attachment region 1030, and thus, the leaflet attachment region 1043, specifically through modification of the divergence and curvature of the support attachment region 1030.

Figure 33:
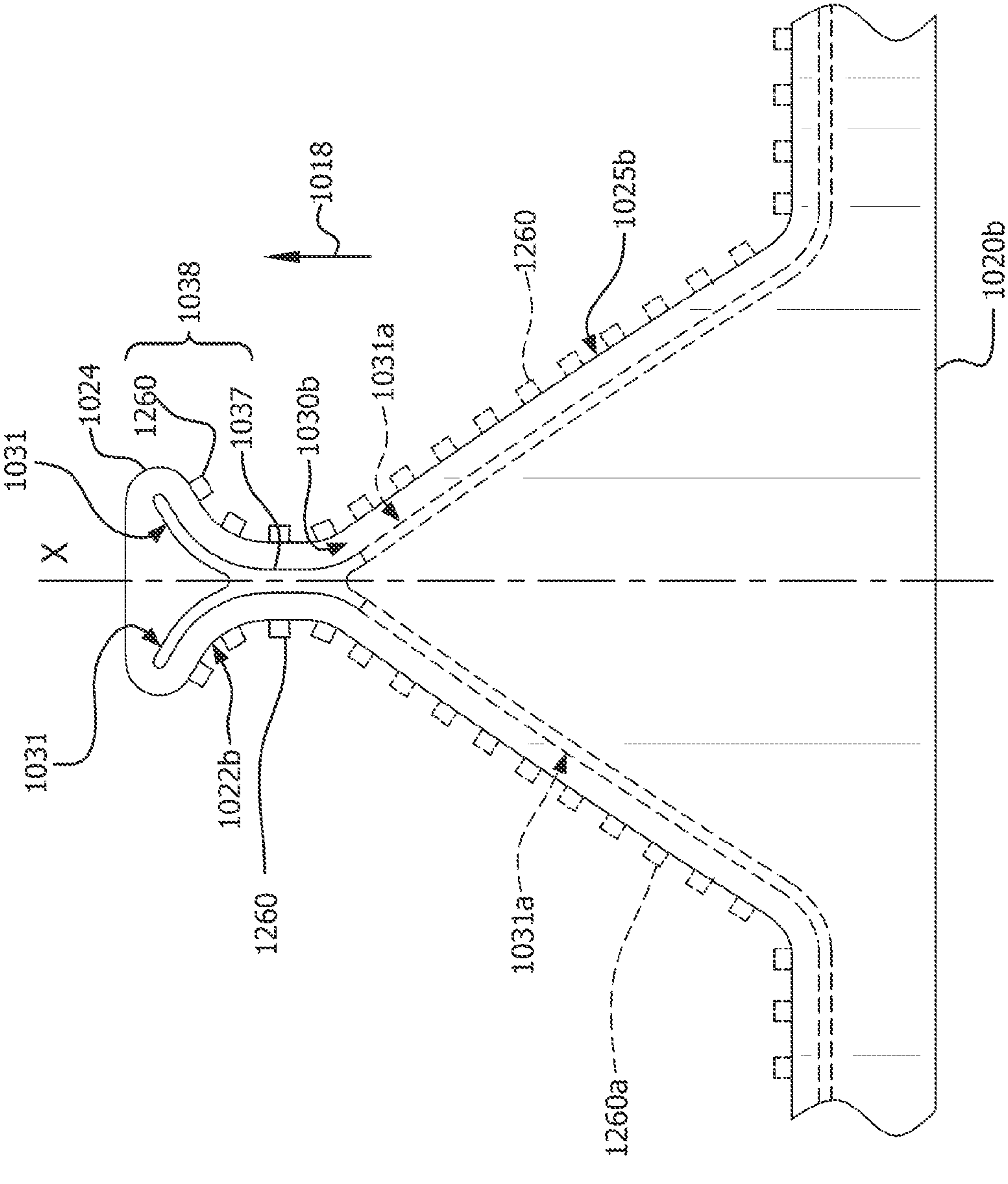
FIG. 33 is a side view of a frame in accordance with another embodiment that shows a support attachment region defined by a continuous slot through the frame that defines a proximal edge.

FIG. 33 is a side view of an embodiment of a leaflet frame 1020*b* that substantially corresponds to the embodiment of FIG. 29, but for and alternative configuration of the commissure post 1022*b*. In the embodiment of FIG. 33, the commissure post 1022*b* defines a continuous slot 31031 that defines adjacent support attachment regions 1030 that diverge from a location away from the commissure post tip 1024 in the outflow direction 1018 towards the commissure post tip 1024. While the embodiment of FIG. 29 includes two slots 1031 that are defined at a neck 1037 of the commissure post 1922, the embodiment of FIG. 33 includes one slot 1031 that is defined at the neck 1037. Thus, in some examples, the commissure post 1022 may include a plurality of slots 1031 that converge to a single slot 1031 at a neck 1037 of the commissure post 1022. The commissure regions 1052 of the adjacent respective leaflets 1040 of the configuration illustrated in FIG. 33 will be in closer proximity to each other in the neck 1037 as compared to the commissure regions 1052 of the adjacent respective leaflets 1040 of the configuration illustrated in FIG. 29. Referring to FIGS. 28A-28B, in accordance with an embodiment, the commissure regions 1052 of the adjacent respective leaflets 1040 will be in contact and sealing engagement with each other at the neck 1037 when in the configuration illustrated in FIG. 33. Each leaflet 1040 is received within the slot 1031 defined in the leaflet frame 1020 with the commissure regions 1052 extending through the slot 1031 of the frame commissure post 1022. Each outer margin 1042 of the leaflet 1040 is thus "inserted" or otherwise extends through the slot 1031 of the leaflet frame 1020*b*. The outer margin 1042 of each leaflet 1040 is folded underneath the support attachment region 1030*b* along the fold line 1058. At this point, attachment means couple the outer margin 1042 to the leaflet frame 1020*b* in a manner consisted with the leaflet to leaflet frame coupling descriptions above. As shown in FIG. 33 and described above with regard to FIG. 29, the slot 1031 may optionally extend between adjacent commissure posts 1022 to define one or more slots 1031*a*.

Referring also to FIGS. 27A and 28A, a plurality of leaflets 1040 each define two termini 1056 at an intersection of a leaflet free edge 1054 and a leaflet attachment region 1043, the leaflet attachment region 1043 of each leaflet 1040 being coupled to the leaflet frame 1020 at the support attachment region 1030 such that the leaflet attachment region 1043 adjacent the terminus 1056 of two adjacent leaflets 1040 diverge relative to each other from a location away from the terminus 1056 to the terminus 1056.

In the previous embodiments, the diverging support attachment region 1030 at the commissure post 1022 can be geometrically configured to distribute the maximum loaded stress to meet design requirements. In the embodiments previously presented, the respective diverging support attachment region 1030 at the commissure post 1022 curve away from each other about a radius from a location away from the commissure post tip 1024 in the outflow direction 1018, as shown in FIGS. 27A and 29. It is appreciated that the respective diverging support attachment region 1030 at the commissure post 1022 may diverge from each other in a linear manor, such as in a Y shape.

Figure 34:
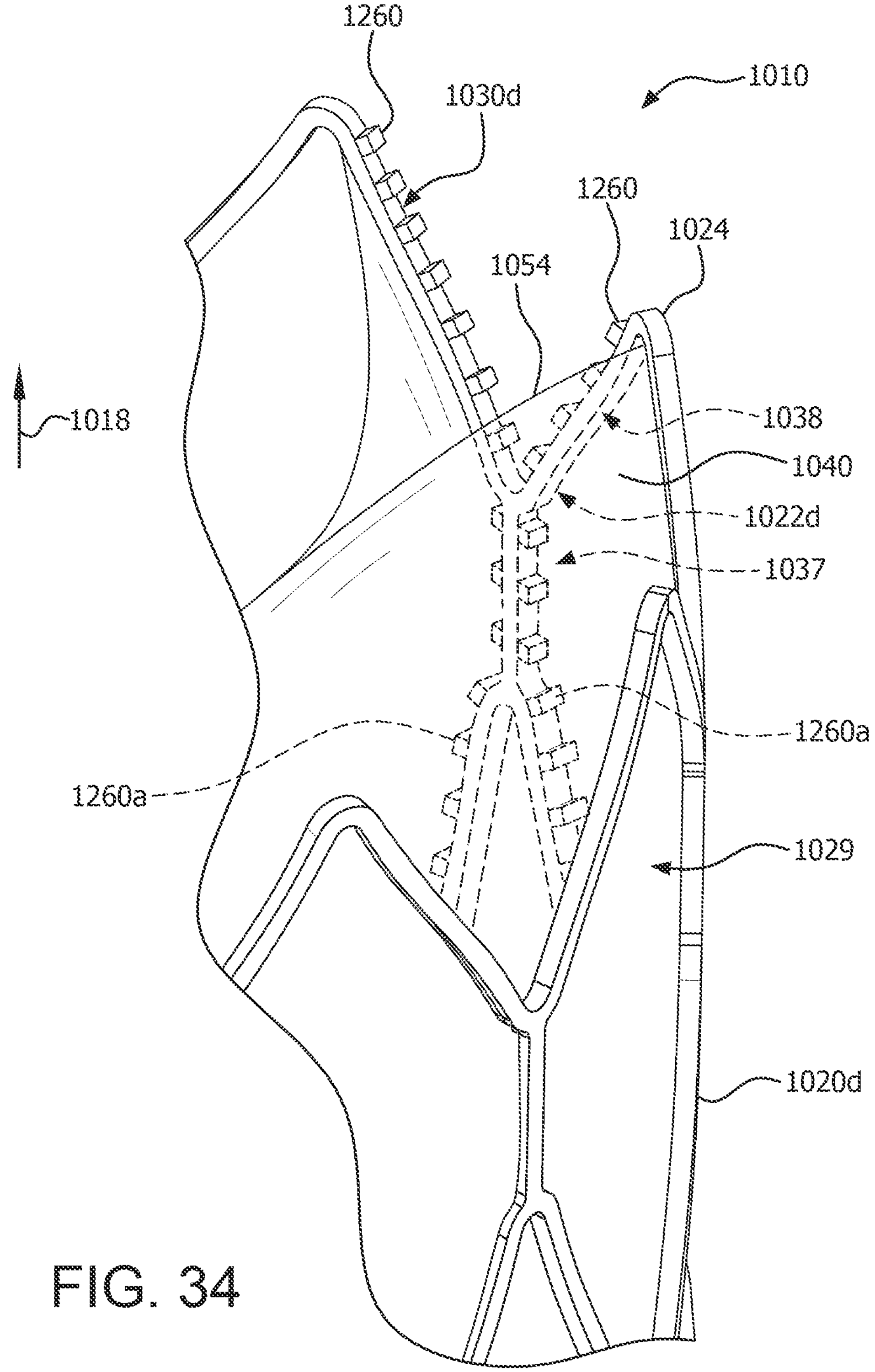
FIG. 34 shows a frame that is operable to be used in a transcatheter procedure, wherein the frame has a variable diameter, in accordance with another embodiment.
Figure 35:
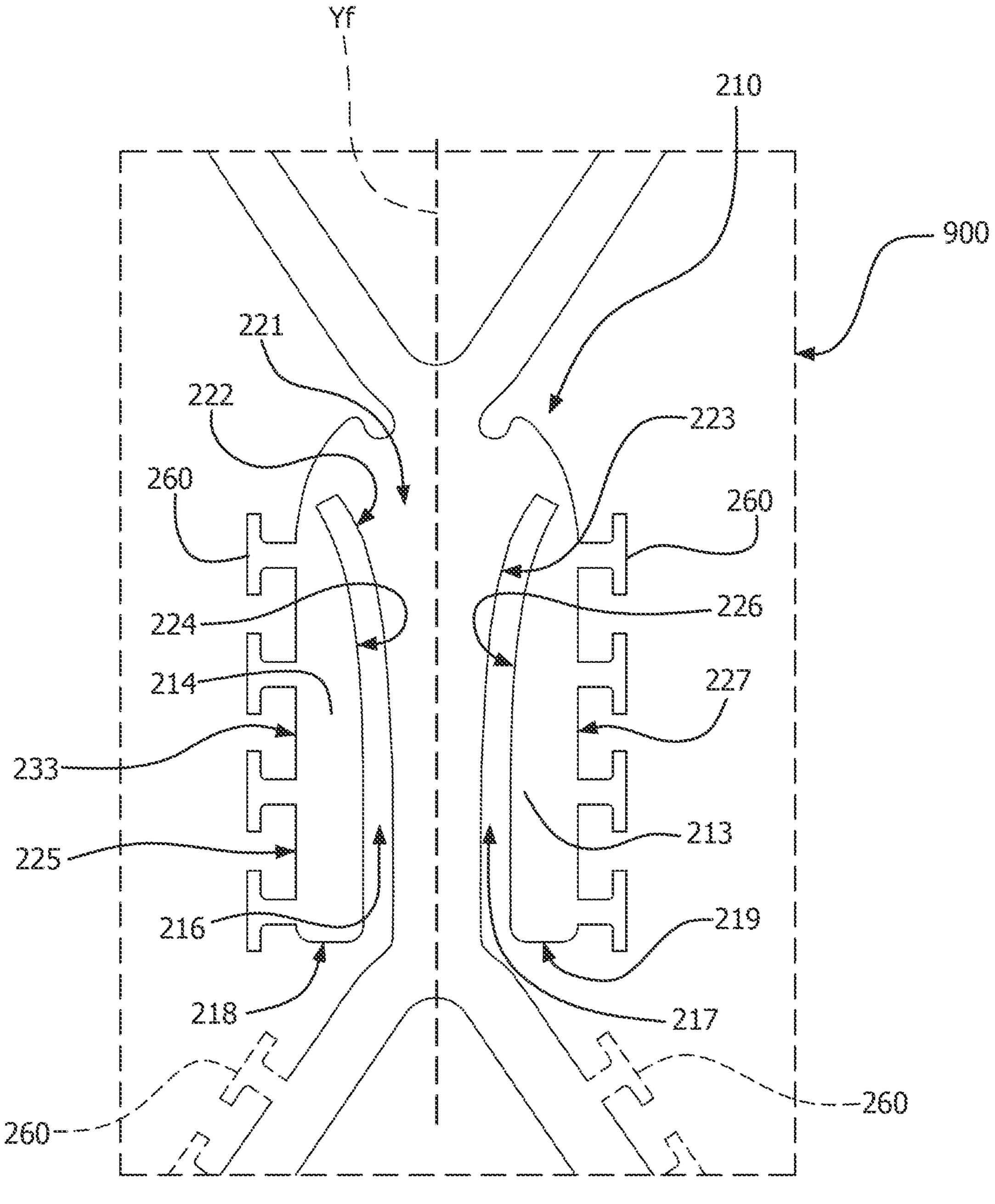
FIG. 35 is an alternative configuration of the commissure post shown in FIG. 9A, wherein the slots diverge from one another, according to some embodiments.

FIG. 34 is a side view of a leaflet frame 1020*d*, an example of a cut tube, but could also be presented as a continuous wire or a woven wire form, in accordance with an embodiment. The leaflet frame 1020*d* is an example of a transcatheter valve frame which defines a plurality of interconnected diamond-shaped apertures 1029, wherein each leaflet commissure region may follow a diverging portion of one of the apertures 1029. Alternatively, each leaflet commissure region of a transcatheter valve frame may correspond to a portion of the leaflet frame 1020*d* consistent with the embodiment depicted in FIGS. 9A and 9B (see, e.g., FIG. 35, showing slots 216 and 217 that diverge in the outflow direction proximate the commissure tip 221). As shown in FIG. 34, the leaflet frame 1020*d* defines a commissure post 1022 that defines a neck 37 adjacent linking members of the frame elements that define the aperture 1029.

The commissure post 1022*d* defines adjacent support attachment regions 1030*d* that diverge from a location away from the commissure post tip 1024 in the outflow direction 1018 towards the commissure post tip 1024. Thus, each of two respective commissure regions 1052 of complementary leaflets 1040 will diverge from the neck 1037, that is, from a location away from the commissure post tip 1024, in the outflow direction 1018 towards the commissure post tip 1024. The commissure region 1052 of the respective leaflet 1040 is coupled to the commissure post 1022*d* of the leaflet frame 1020*d* about the respective diverging support attachment region 1030*d* at the leaflet fold line 1058. The leaflet frame 1020*d* is operable to hold and support a plurality of leaflets 1040. As shown, the leaflet frame 1020*d* includes a plurality of leaflet frame projections 1260 along the diverging support attachment region 1030*d*, as well as one or more optional leaflet frame projections 1260*a* that may extend between adjacent commissure posts 1022*d* of the leaflet frame 1020*d*, consistent with the discussion of optional leaflet frame projections 1260*a*, above. The leaflet frame 1020*d* is annular, that is, it defines a cylinder having a lumen defining an axis X and the plurality of commissure posts 1022*d* extending parallel to the axis X that are spaced from one another.

Referring also to FIGS. 27A and 28A, a plurality of leaflets 1040 each define two termini 1056 at an intersection of a leaflet free edge 1054 and a leaflet attachment region 1043, the leaflet attachment region 1043 of each leaflet 1040 being coupled to the leaflet frame 1020*d* at the support attachment region 1030*d* such that the leaflet attachment region 1043 adjacent the terminus 1056 of two adjacent leaflets 1040 diverge relative to each other from a location away from the terminus 1056 to the terminus 1056.

In the embodiments previously presented, since the diverging support attachment regions (e.g., 1030, 1030*b*, 1030*d*) at the commissure post (e.g., 1022, 1022*b*, 1022*d*) diverge from each other from a location away from the commissure post tip 1024 in the outflow direction 1018 towards the commissure post tip 1024, the diverging support attachment regions (e.g., 1030, 1030*b*, 1030*d*) may have the same length as a corresponding non-diverging support attachment region (e.g., 1030*a*) but with a reduced overall frame height. This is even more so with diverging support attachment regions (e.g., 1030, 1030*b*, 1030*d*), further reducing the frame height. Referring again to FIG. 31, the frame height H2 of non-diverging support attachment regions 30*a* is longer than the frame height H2 of diverging support attachment regions 30.

FIG. 35 is an illustration of an alternative leaflet frame design that includes a commissure post 210 consistent with the leaflet frame 900 illustrated and described above, with the exception that the slots 216 and 217 diverge from one another in the outflow direction along the commissure post 210 such that the slots 216 and 217 are further apart at the commissure tip 221 than near the free ends 218 and 219 of the tines first and second tine 214 and 215, respectively (e.g., proximate the commissure post base).

Figure 36:
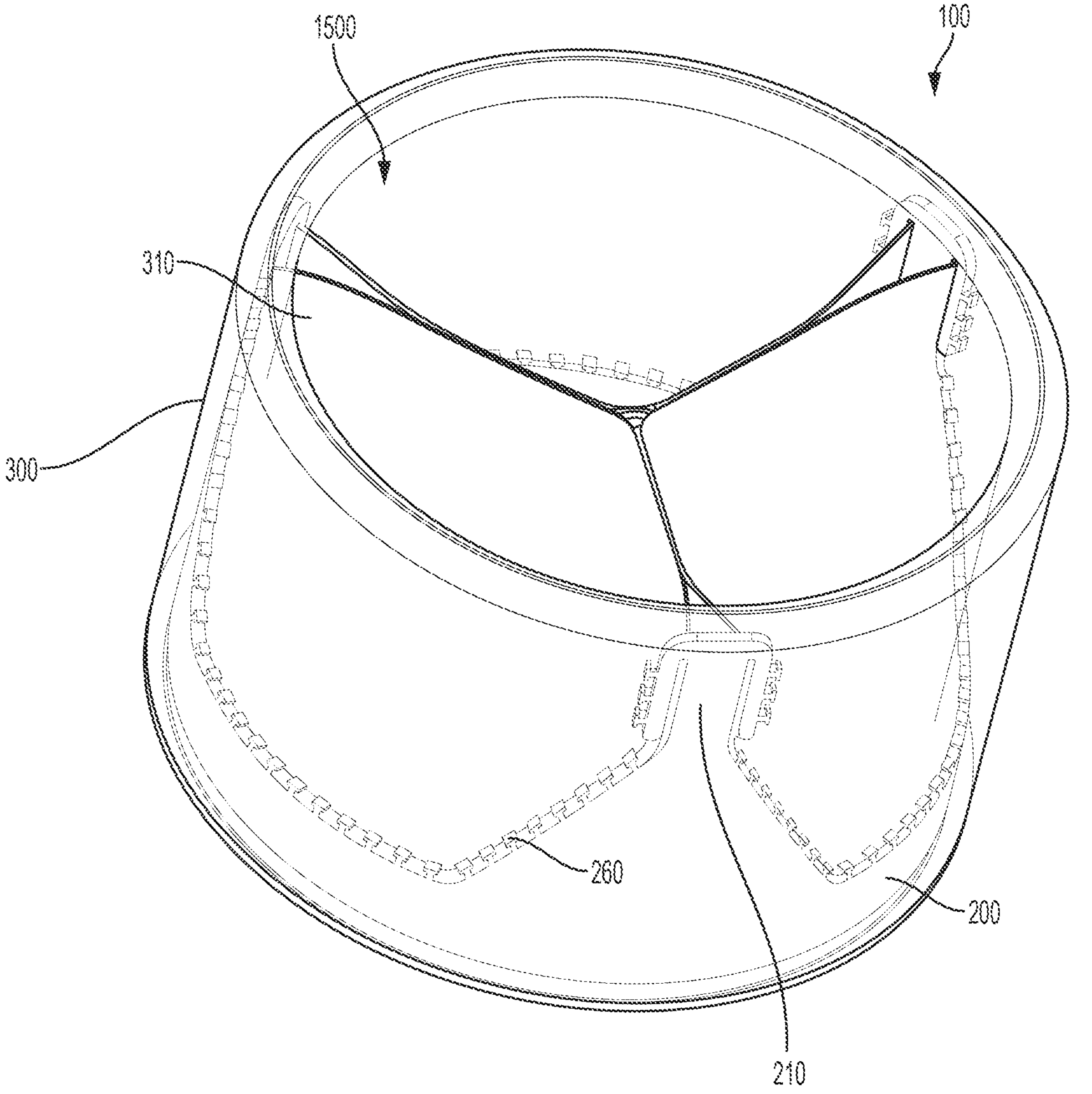
FIG. 36 is a perspective view of an illustration of an example jacket coupled to a prosthetic valve, according to some embodiments.
Figure 37:
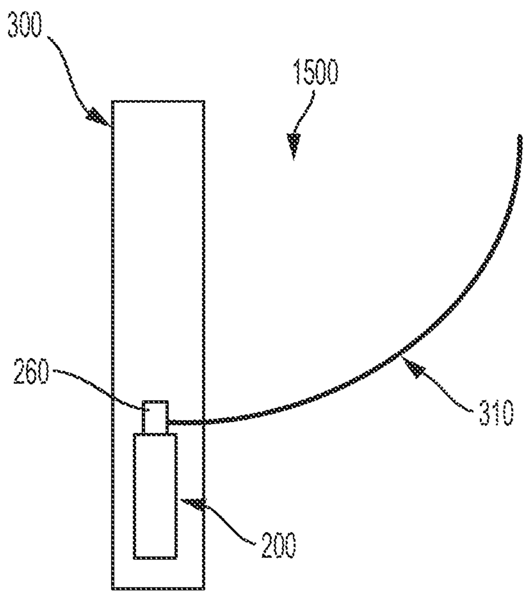
FIG. 37 is a cross-sectional illustration of the jacket and the prosthetic valve shown in FIG. 36, in accordance with an embodiment is a perspective view of an illustration of another example jacket coupled to a prosthetic valve, according to some embodiments.

FIG. 36 is a perspective view of an illustration of an example jacket coupled to a prosthetic valve, in accordance with an embodiment. FIG. 37 is a cross-sectional illustration of the jacket and the prosthetic valve shown in FIG. 36 taken along a longitudinal axis at a point equidistant between adjacent commissure posts 210, in accordance with an embodiment. The components of the prosthetic valve 100 include a plurality of leaflets 310 and a leaflet frame 200 (which corresponds to the leaflet frame 200 illustrated and described above with respect to FIG. 2A) that includes a plurality of commissure posts 210 flanked on each side by leaflet window frame element(s). The leaflet frame 200 is operable to mechanically couple and support the leaflets 310 by way of, at least in part, a plurality of leaflet frame projections 260.

The jacket 300 may be joined to the leaflet frame 200 in order to enhance the biocompatibility of the leaflet frame 200 and the prosthetic valve 100. More specifically, the jacket 300 is configured to cover gaps, spaces, interfaces or other structural aspects that are present in the leaflet frame 200 and/or interfaces between the leaflet frame 200 and the one or more leaflets 310 attached to the leaflet frame 200, and/or one or more leaflet retention features (e.g., leaflet retention features 400, 500, 600, 700, 800, 900), to enhance the biocompatibility of the leaflet frame 200. In some examples, the jacket 300 additionally helps maintain mechanical attachment of the leaflets 310 to the leaflet frame 200, including the leaflet frame projections 260. In addition, the jacket 300 may be configured to include smooth transition for the prosthetic valve 100 help minimize gaps and crevices, and thus help minimize stagnate blood regions and/or thrombus formation.

The components of the prosthetic valve 100 include a plurality of leaflets 310 and a leaflet frame 200 that includes a plurality of commissure posts 210 flanked on each side by leaflet window frame element(s). The leaflet frame 200 is operable to mechanically couple and support the leaflets 310 by way of, at least in part, a plurality of leaflet frame projections 260 consistent with the discussion above.

The jacket 300 may be joined to the leaflet frame 200 in order to enhance the biocompatibility of the leaflet frame 200 and the prosthetic valve 100. More specifically, the jacket 300 is configured to cover gaps, spaces, interfaces or other structural aspects that are present in the leaflet frame 200 and/or interfaces between the leaflet frame 200 and the one or more leaflets 310 attached to the leaflet frame 200, and/or one or more leaflet retention features (e.g., leaflet retention features 400, 500, 600, 700, 800, 900), which helps enhance the biocompatibility of the leaflet frame 200. In addition, the jacket 300 may be configured to include smooth transition for the prosthetic valve 100 help minimize gaps and crevices, and thus help minimize stagnate blood regions and/or thrombus formation. In addition, and as shown, the jacket 300 may extend to cover (outflow side) ends of the commissure posts 210. The jacket 300 being formed and configured in this manner may help minimize stagnate blood regions and/or thrombus formation by filling a gap 1500 behind the outflow side of the leaflets 310 and the leaflet frame 200. While the jacket 300 is shown coupled with the leaflet frame 200, it is to be appreciated that the jacket 300 is couplable with any of the various other leaflet frames (e.g., 1020) illustrated and described herein.

In certain instances, the jacket 300 may be include an inflow and an outflow portion that couple together about the leaflet frame 200. In other instances, the jacket 300 may be a single piece directly coupled or overmolded to the leaflet frame 200. In addition, portions of the jacket 300 may also be coupled or overmolded to portions of the leaflets 310.

In certain instances, the jacket 300 may be include an inflow and an outflow portion that couple together bout the leaflet frame 200. In other instances, the jacket 300 may be a single piece directly coupled or overmolded to the leaflet frame 200. In addition, portions of the jacket 300 may also be coupled or molded to the leaflet frame 200 such the jacket 300 extends onto (and may be bonded with) one or more portions of the leaflets 310.

In certain instances, the jacket 300 may be formed of a rigid polymer. In certain instances, the jacket 300 may be formed of a fluoropolymer (e.g., a TFE-PMVE copolymer).

In these instances, the TFE-PMVE copolymer jacket 300 may bond to the synthetic leaflets 310.

In certain instances, the prosthetic valve 100 (with the jacket 300) may be directly implanted into a patient and in other instances, the prosthetic valve 100 (with the jacket 300) may be arranged within a conduit as mentioned above. The prosthetic valve 100 having a wall height extending adjacent or up to ends of commissure posts 210, as shown in FIGS. 36 and 37, may help minimize stagnate blood regions and/or thrombus formation by extending the gap 1500 behind the outflow side of the leaflets 310 and the leaflet frame 200.

Figure 38:
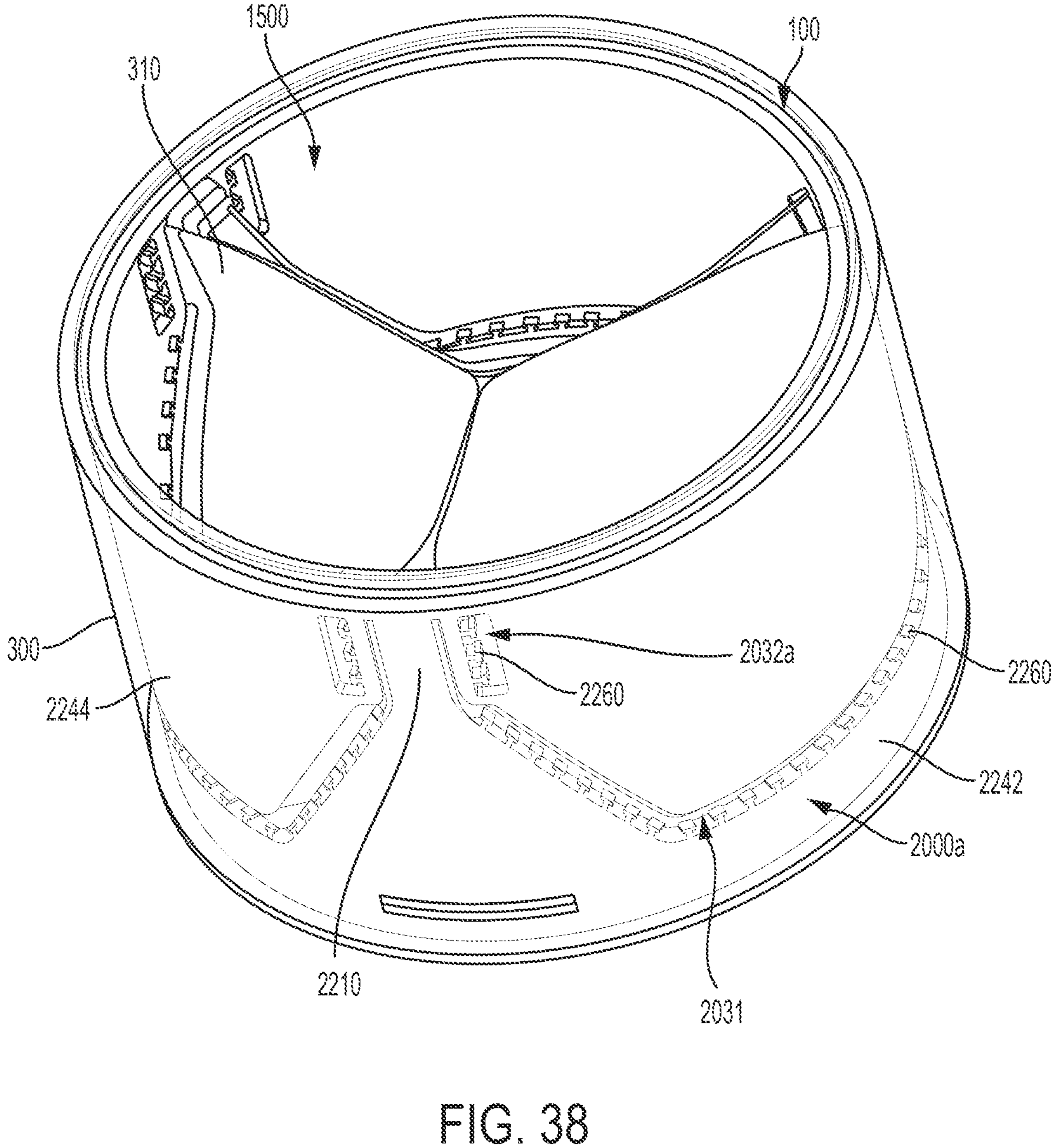
FIG. 38 is a perspective view of an illustration of another example jacket coupled to a prosthetic valve, according to some embodiments.

FIG. 38 is a perspective view of an illustration of an example jacket 300 coupled to a prosthetic valve 100, in accordance with an embodiment. The components of the prosthetic valve 100 include a plurality of leaflets 310 and a leaflet frame 2000 that includes a plurality of commissure posts 2210 (which can be understood to generally correspond to the various other commissure posts—210 and 1022—illustrated and described above) that are flanked on each side by leaflet window frame element(s). The leaflet frame 2000 is operable to mechanically couple and support the leaflets 310 by way of, at least in part, a plurality of leaflet frame projections 2260 (which correspond with leaflet frame projections 260 and 1260, described above).

The leaflet frame 2000 includes a relief or slot 2031 extending along one or more portions thereof (which can be understood to correspond with the slot 1031 described above, in that one or more leaflets may extend through the slot 2031 for coupling to the leaflet frame 2000). As shown in FIG. 38, the slot 2031 operates to define an inflow portion 2242 (which corresponds with those regions of the leaflet frame 2000 on an inflow side of the slot 2031) and an outflow portion 2244 (which corresponds with those regions of the leaflet frame 2000 on an outflow side of the slot 2031). The leaflet frame 2000 includes one or more portions (e.g., frame elements such as struts or links) that extend between the inflow and outflow portions 2242 and 2244. As shown, in some examples, the slot 2031 may include one or more leaflet frame projections 2260. Additionally, as shown, the leaflet frame 2000 may include a second slot or relief 2032 adjacent the slot 2031 along the commissure post 2210. As shown, in some examples, the slots 2031 and 2032 may include one or more leaflet frame projections 2260. Consistent with the discussion above, the leaflets (e.g., 310 and 1040) are coupled to the leaflet frame 2000 via the one or more slots 2031 and 2032, and the one or more leaflet frame projections 2260. The leaflet frame 2000 can be etched, cut, laser cut, stamped, three-dimensional printed, wire wound, or formed according to any of the other methods referred to herein.

The jacket 300 may be joined to the leaflet frame 2000 in order to enhance the biocompatibility of the leaflet frame 2000 and the prosthetic valve 100. More specifically, the jacket 300 is configured to cover gaps, spaces, interfaces or other structural aspects that are present in the leaflet frame 2000 and/or interfaces between the leaflet frame 2000 and the one or more leaflets 310 attached to the leaflet frame 2000, and/or one or more leaflet retention features (e.g., leaflet retention features 400, 500, 600, 700, 800, 900), to enhance the biocompatibility of the leaflet frame 2000. In some examples, the jacket 300 additionally helps maintain mechanical attachment of the leaflets 310 to the leaflet frame 2000, including the leaflet frame projections 2260. In addition, the jacket 300 may be configured to include smooth transition for the prosthetic valve 100 help minimize gaps and crevices, and thus help minimize stagnate blood regions and/or thrombus formation. In addition and as shown, the jacket 300 may extend to cover (outflow side) ends of the commissure posts 2210. The jacket 300 being formed and configured in this manner may help minimize stagnate blood regions and/or thrombus formation by filling a gap 1500 behind the outflow side of the leaflets 310 and the leaflet frame 2000.

In certain instances, the jacket 300 may include an inflow and an outflow portion that couple together about the leaflet frame 2000. In other instances, the jacket 300 may be a single piece directly coupled (e.g., affixed to, coated on, molded to) the leaflet frame 2000. In addition, portions of the jacket 300 may also be coupled to or molded onto the leaflet frame 2000 such that the jacket 300 extends onto one or more portions of the leaflets.

In certain instances, the jacket 300 may be include an inflow and an outflow portion that couple together about the leaflet frame 2000. In other instances, the jacket 300 may be a single piece directly coupled or overmolded to the leaflet frame 2000. In addition, portions of the jacket 300 may also be coupled or molded to the leaflet frame 2000 such the jacket 300 extends onto (and may be bonded with) one or more portions of the leaflets 310.

In certain instances, the jacket 300 may be formed of a rigid polymer. In certain instances, the jacket 300 may be formed of a fluoropolymer (e.g., a TFE-PMVE copolymer). In these instances, the TFE-PMVE copolymer jacket 300 may bond to the synthetic leaflets 310.

Figure 39:
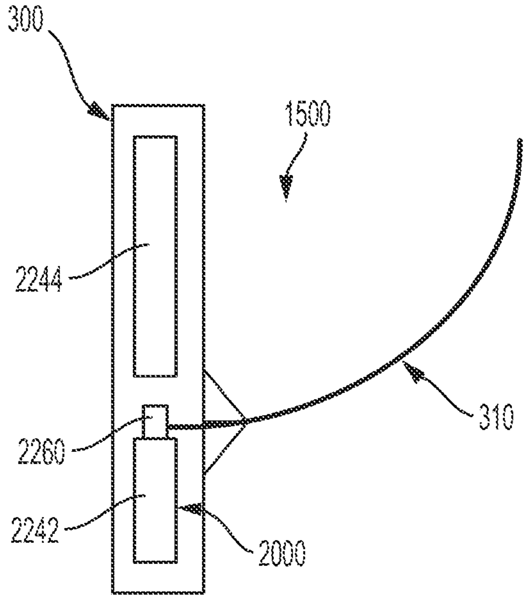
FIG. 39 is a cross-sectional illustration of the jacket and the prosthetic valve shown in FIG. 38 as arranged in a conduit, in accordance with an embodiment

FIG. 39 is a cross-sectional illustration of the jacket 300 and the prosthetic valve 100 shown in FIG. 36 taken along a longitudinal axis at a point equidistant between adjacent commissure posts 2210, in accordance with an embodiment. As shown, the leaflet 310 is coupled to the leaflet frame 2000 such that the inflow portion 2242 is positioned on an inflow side of the leaflet 310 and such that the outflow portion 2244 is position on an outflow side of the leaflet 310.

The prosthetic valve 100 having a wall height extending adjacent or up to ends of commissure posts 2210, as shown in FIGS. 38 and 39, may help minimize stagnate blood regions and/or thrombus formation by extending the gap 1500 behind the outflow side of the leaflets 310 and the leaflet frame 2000.

FIG. 40 is a perspective view of an illustration of another example jacket coupled to a prosthetic valve, in accordance with an embodiment. The components of the prosthetic valve 100 include a plurality of leaflets 310 and a leaflet frame 2000*a* that includes a plurality of commissure posts 2210*a* (which can be understood to generally correspond to the various other commissure posts—210, 1022, and 2210*a*—illustrated and described above) that are flanked on each side by leaflet window frame element(s). The leaflet frame 2000 is operable to mechanically couple and support the leaflets 310 by way of, at least in part, a plurality of leaflet frame projections 2260 (which correspond with leaflet frame projections 260 and 1260, described above).

The leaflet frame 2000*a* is similar to the leaflet frame 2000 illustrated and described above, and includes a relief or slot 2031*a* extending along one or more portions thereof (which can be understood to correspond with the slots 1031 and 2031 described above, in that one or more leaflets may extend through the slot 2031*a* for coupling to the leaflet frame 2000*a*). As shown in FIG. 40, the slot 2031*a* operates to define an inflow portion 2242*a* (which corresponds with those regions of the leaflet frame 2000 on an inflow side of the slot 2031*a*) and an outflow portion 2244*a* (which corresponds with those regions of the leaflet frame 2000 on an outflow side of the slot 2031*a*). Similar to the leaflet frame 2000, the leaflet frame 2000*a* also includes one or more portions (e.g., frame elements such as struts or links) that extend between the inflow and outflow portions 2242*a* and 2244*a*. As shown, in some examples, the slot 2031*a* may include one or more leaflet frame projections 2260. Additionally, as shown, the leaflet frame 2000*a* may include a second slot or relief 2032*a* adjacent the slot 2031*a* along the commissure post 2210. As shown, in some examples, the slots 2031*a* and 2032*a* may include one or more leaflet frame projections 2260. Consistent with the discussion above, the leaflets (e.g., 310 and 1040) are coupled to the leaflet frame 2000*a* via the one or more slots 2031*a* and 2032*a*, and the one or more leaflet frame projections 2260.

The leaflet frame 2000*a* can be etched, cut, laser cut, stamped, three-dimensional printed, wire wound, or formed according to any of the other methods referred to herein.

FIG. 41 is a cross-sectional illustration of the jacket 3000 and the prosthetic valve 100 shown in FIG. 42 taken along a longitudinal axis at a point equidistant between adjacent commissure posts 2210, in accordance with an embodiment. As shown, the leaflet 310 is coupled to the leaflet frame 2000*a* such that a protrusion of the outflow portion 3002 of the jacket 3000 is received within the void 2248*a* of the leaflet frame 2000*a*, and such that a protrusion of the inflow portion 3004 of the jacket 3000 is received within the void 2246*a* of the leaflet frame 2000*a*.

Figure 42B:
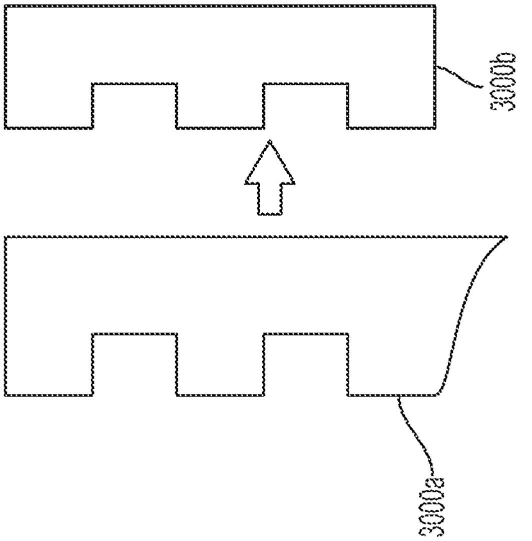
Figure 42A:
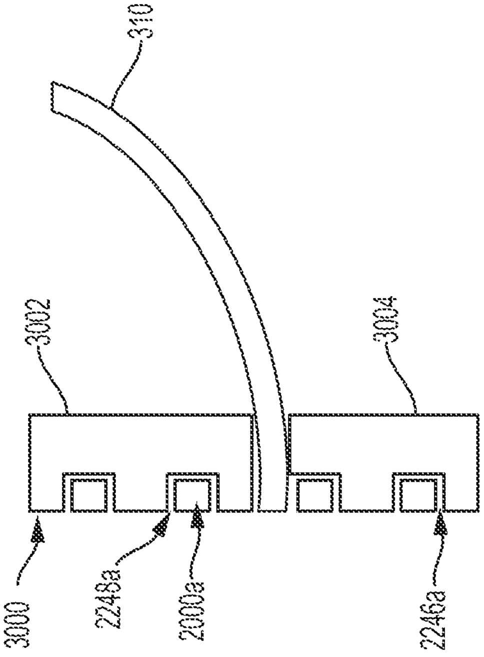

Referring now to FIGS. 42A and 42B, the jacket 3000 may be joined to the leaflet frame 2000*a* in order to enhance the biocompatibility of the leaflet frame 2000*a* and the prosthetic valve 100. More specifically, the jacket 3000 is configured to cover gaps, spaces, interfaces or other structural aspects that are present in the leaflet frame 200 and/or interfaces between the leaflet frame 2000 and the one or more leaflets 310 attached to the leaflet frame 2000*a* to enhance the biocompatibility of the leaflet frame 2000*a*. In certain instances, the jacket 3000 may be joined to the leaflet if the leaflet frame 200 is overmolded, as discussed above.

In certain instances, it may be beneficial for the jacket 3000 to be formed of a flexible component such as silicone. The jacket 3000 may minimize a seam and create a seal with compressive force in gaps between the leaflets 310 and the frame 2000*a*. In certain instances, portions of the jacket 3000 may be formed of different materials. The jacket 3000 may include a first portion 3002 (an outflow jacket portion) and a second portion 3004 (an inflow jacket portion). The inflow portion 3004 (also referred to as a first portion of the jacket) of the jacket 3000, for example, may be formed of a different material than the outflow portion 3002 (also referred to as a second portion) of the jacket 3000. In certain instances, the outflow portion 3002 of the jacket 3000 may be formed of more flexible material (e.g., silicone) than the inflow portion 3004 of the jacket 3000 (e.g., a thermoplastic polymer or a rigid material overmolded with silicone). The outflow portion 3002 and the inflow portion 3004 are configured to couple to the leaflet frame 2000 to form the jacket 3000.

In some examples, as shown in FIGS. 42A and 42B, the leaflet frame 2000*a* includes one or more voids, such as voids 2246*a* and 2248*a*. The voids 2246*a* and 2248*a* are configured to accommodate one or more protrusions of one or more of the inflow and outflow portions 3004 and 3002, respectively, of the jacket 3000. Accordingly, in various examples, the protrusions of inflow and outflow portions 3004 and 3002 of the jacket 3000, and the voids of the leaflet frame 2000*a*, are complementary of one another such that the jacket 3000 can be coupled with the leaflet frame 2000*a* by aligning the protrusions with the voids of the leaflet frame 2000*a*.

In certain instances, the inflow and outflow portions 3004 and 3002 of the jacket 3000 are secured with the leaflet frame 2000*a* by at least one of swaging, a snap fit, a click fit, one or more staples, tape, adhesives, or other known methods.

In certain instances, the prosthetic valve 100 (with the jacket 300) may be directly implanted into a patient and in other instances, the prosthetic valve 100 may be arranged within a conduit as mentioned above.

FIGS. 42A-42B are illustrations of a leaflet 310 arranged within the jacket 3000 and leaflet frame 2000*a* shown in FIGS. 40 and 41, in accordance with an embodiment. As shown in FIG. 42B, the jacket 3000 is flexible and compressible (e.g., one or more of the inflow and outflow portions 3004 and 3002 are flexible and compressible). The jacket 3000*a* may compress longitudinally when arranged with the frame 2000*a* and take the shape of the compressed jacket 3000*b*, as shown in FIG. 42B. As shown in FIG. 41A, the jacket 300 may minimize a seam and create a seal with compressive force in gaps between the leaflets 310 and the frame 2000 as a result of the compressibility of the jacket 3000. That is, by providing that one or more of the inflow and outflow portions 3004 and 3002 of the jacket 3000 are flexible and compressible, the jacket 3000 may be compressed against those portions of the leaflet 310 extending between the inflow and outflow portions 3004 and 3002 of the jacket 3000 when the jacket 3000 is coupled with the leaflet frame 2000*a*. In various examples, the voids (e.g., leaflet frame 2246*a* and 2248*a*) of the leaflet frame 2000*a* may be configured such that, when the inflow and outflow portions 3004 and 3002 are coupled with the leaflet frame 2000*a*, one or more of the inflow and outflow portions 3004 and 3002 become compressed against the leaflet 310. It will be appreciated that achieving such a compressed configuration can be accomplished by oversizing one or more of the inflow and outflow portions 3004 and 3002 of the jacket 3000 relative to the leaflet frame 2000*a*. For instance, where a distance from the leaflet 310 to void 2246*a* is a first distance, the inflow portion 3004 of the jacket 3000 may be configured such that region of the inflow portion 3004 of the jacket 3000 that interfaces with the leaflet 310 is a second distance (greater than the first distance) from the protrusion that is complimentary to (and configured to be received within) void 2246*a* when the inflow portion 3004 of the jacket 3000 is in a non-compressed state.

Leaflet Materials

The various leaflets disclosed herein (e.g., 310 and 1040) can comprise any biocompatible material sufficiently compliant and flexible, such as a biocompatible polymer (e.g., synthetic) and biological tissue (e.g., of animal origin). For instance, in various examples, the leaflets (e.g., 310 and 1040) are formed of a biocompatible, synthetic material (e.g., including ePTFE and ePTFE composites, or other materials as desired). In accordance with an embodiment, the composite material includes an expanded fluoropolymer material made from porous ePTFE membrane, for instance as generally described in U.S. Pat. No. 7,306,729 to Bacino, referred to above. In other examples, the leaflets are formed of a natural material, such as repurposed tissue, including bovine tissue, porcine tissue, or the like.

The expandable fluoropolymer, used to form the expanded fluoropolymer material described, can comprise PTFE homopolymer. In some embodiments, blends of PTFE, expandable modified PTFE and/or expanded copolymers of PTFE can be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al. The expanded fluoropolymer membrane can comprise any suitable microstructure, such as pores, for achieving the desired leaflet performance. Other biocompatible polymers that can be suitable for use in the leaflets (e.g., 310 and 1040) include but are not limited to the groups of urethanes, silicones (organopolysiloxanes), copolymers of silicon-urethane, styrene/isobutylene copolymers, polyisobutylene, polyethylene copoly (vinyl acetate), polyester copolymers, nylon copolymers, fluorinated hydrocarbon polymers and copolymers or mixtures of each of the foregoing.

As used herein, the term "elastomer" refers to a polymer or a mixture of polymers that has the ability to be stretched to at least 1.3 times its original length and to retract rapidly to approximately its original length when released. The term "elastomeric material" refers to a polymer or a mixture of polymers that displays stretch and recovery properties similar to an elastomer, although not necessarily to the same degree of stretch and/or recovery. The term "non-elastomeric material" refers to a polymer or a mixture of polymers that displays stretch and recovery properties not similar to either an elastomer or elastomeric material, that is, considered not an elastomer or elastomeric material.

In accordance with some embodiments herein, the leaflet (e.g., 310 and 1040) comprises a composite material having at least one porous synthetic polymer membrane layer having a plurality of pores and/or spaces and an elastomer and/or an elastomeric material and/or a non-elastomeric material filling the pores and/or spaces of the at least one synthetic polymer membrane layer. In accordance with other examples, the leaflet (e.g., 310 and 1040) further comprises a layer of an elastomer and/or an elastomeric material and/or a non-elastomeric material on the composite material. In accordance with examples, the composite material comprises porous synthetic polymer membrane by weight in a range of about 10% to 90%.

An example of a porous synthetic polymer membrane includes expanded fluoropolymer membrane having a node and fibril structure defining the pores and/or spaces. In some examples, the expanded fluoropolymer membrane is expanded polytetrafluoroethylene (ePTFE) membrane. Another example of porous synthetic polymer membrane includes microporous polyethylene membrane.

Examples of an elastomer and/or an elastomeric material and/or a non-elastomeric material include, but are not limited to, copolymers of tetrafluoroethylene and perfluoromethyl vinyl ether (TFE/PMVE copolymer), (per)fluoroalkylvinylethers (PAVE), urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing. In some examples, the TFE/PMVE copolymer is an elastomer comprising essentially of between 60 and 20 weight percent tetrafluoroethylene and respectively between 40 and 80 weight percent perfluoromethyl vinyl ether. In some examples, the TFE/PMVE copolymer is an elastomeric material comprising essentially of between 67 and 61 weight percent tetrafluoroethylene and respectively between 33 and 39 weight percent perfluoromethyl vinyl ether. In some examples, the TFE/PMVE copolymer is a non-elastomeric material comprising essentially of between 73 and 68 weight percent tetrafluoroethylene and respectively between 27 and 32 weight percent perfluoromethyl vinyl ether. The TFE and PMVE components of the TFE-PMVE copolymer are presented in wt %. For reference, the wt % of PMVE of 40, 33-39, and 27-32 corresponds to a mol % of 29, 23-28, and 18-22, respectively.

In some examples, the TFE-PMVE copolymer exhibits elastomer, elastomeric, and/or non-elastomeric properties.

In some examples, the composite material further comprises a layer or coating of TFE-PMVE copolymer comprising from about 73 to about 68 weight percent tetrafluoroethylene and respectively from about 27 to about 32 weight percent perfluoromethyl vinyl ether.

In some examples, the leaflet is an expanded polytetrafluoroethylene (ePTFE) membrane having been imbibed with TFE-PMVE copolymer comprising from about 60 to about 20 weight percent tetrafluoroethylene and respectively from about 40 to about 80 weight percent perfluoromethyl vinyl ether, the leaflet further including a coating of TFE-PMVE copolymer comprising from about 73 to about 68 weight percent tetrafluoroethylene and respectively about 27 to about 32 weight percent perfluoromethyl vinyl ether on the blood-contacting surfaces.

As discussed above, the elastomer and/or an elastomeric material and/or a non-elastomeric material may be combined with the expanded fluoropolymer membrane such that the elastomer and/or the elastomeric material and/or the non-elastomeric material occupies substantially all of the void space or pores within the expanded fluoropolymer membrane.

Numerous characteristics and advantages have been set forth in the preceding description, including various alternatives together with details of the structure and function of the devices and/or methods. Moreover, the inventive scope of the various concepts addressed in this disclosure has been described both generically and with regard to specific examples. The disclosure is intended as illustrative only and as such is not intended to be exhaustive. For example, the various embodiments of the present disclosure are described in the context of medical applications but can also be useful in non-medical applications. It will be evident to those skilled in the art that various modifications may be made, especially in matters of structure, materials, elements, components, shape, size, and arrangement of parts including combinations within the principles of the inventive concepts discussed herein, to the full extent indicated by the broad, general meaning of the terms in which the appended claims are expressed. To the extent that these various modifications do not depart from the spirit and scope of the appended claims, they are intended to be encompassed therein.

What is claimed is:

1. A prosthetic valve defining an inflow direction into the prosthetic valve and an outflow direction out of the prosthetic valve in operation, the prosthetic valve comprising:

a plurality of leaflets including a first leaflet, a second leaflet, and a third leaflet, each leaflet having a leaflet attachment region, a free edge opposite a base edge, and a fold line that has an outline that is substantially that of an isosceles trapezoid when viewed as a flat profile, wherein the base edge of each leaflet is shorter than and parallel to the free edge, and wherein the leaflet attachment region of each leaflet comprises a plurality of apertures.

2. The prosthetic valve of claim 1, wherein the leaflet attachment regions of the leaflets are divergent in the outflow direction.

3. The prosthetic valve of claim 1, wherein each leaflet comprises a commissure tab adjacent the free edge.

4. The prosthetic valve of claim 3, wherein each commissure tab comprises a plurality of apertures.

5. The prosthetic valve of claim 3, wherein each of the commissure tabs is divergent in the outflow direction.

6. The prosthetic valve of claim 1, further comprising a frame with a plurality of commissure posts, wherein each commissure post includes:

a first tine including a first interior edge and a first exterior edge opposite the first interior edge;

a second tine including a second interior edge and a second exterior edge opposite the second interior edge;

a spine positioned between the first and second tines such that the interior edges of the first and second tines face the spine;

a first slot defined between the first tine and the spine, the leaflet attachment region of one of the leaflets extending through the frame at the first slot; and a second slot defined between the second tine and the spine, the leaflet attachment region of another one of the leaflets extending through the frame at the second slot, the first and second slots diverging from one another in the outflow direction.

7. The prosthetic valve of claim 6, wherein the leaflets each define two termini at an intersection of the leaflet free edge and the leaflet attachment region, the leaflet attachment region of each leaflet being coupled to the frame such that the leaflet attachment region adjacent the terminus of the leaflets when positioned adjacent to one another diverge relative to each other from a location away from the terminus to the terminus.

8. A prosthetic valve defining an inflow direction into the prosthetic valve and an outflow direction out of the prosthetic valve in operation, the prosthetic valve comprising:

a plurality of leaflets including a first leaflet, a second leaflet, and a third leaflet, each leaflet having a leaflet attachment region and a free edge opposite a base edge, wherein the base edge and the free edge of each leaflet are at least substantially parallel when viewed as a flat profile, wherein the base edge of each leaflet is shorter than the free edge, wherein each leaflet comprises a commissure tab adjacent the free edge, and wherein each commissure tab comprises a plurality of apertures and is divergent in the outflow direction.

9. The prosthetic valve of claim 8, wherein the leaflet attachment regions of the leaflets are divergent in the outflow direction.

10. The prosthetic valve of claim 8, wherein the leaflet attachment region of each leaflet comprises a plurality of apertures.

11. The prosthetic valve of claim 8, further comprising a frame with a plurality of commissure posts, wherein each commissure post includes:

a first tine including a first interior edge and a first exterior edge opposite the first interior edge;

a second tine including a second interior edge and a second exterior edge opposite the second interior edge;

a spine positioned between the first and second tines such that the interior edges of the first and second tines face the spine;

a first slot defined between the first tine and the spine, the leaflet attachment region of one of the leaflets extending through the frame at the first slot; and a second slot defined between the second tine and the spine, the leaflet attachment region of another one of the leaflets extending through the frame at the second slot, the first and second slots diverging from one another in the outflow direction.

12. The prosthetic valve of claim 11, wherein the leaflets each define two termini at an intersection of the leaflet free edge and the leaflet attachment region, the leaflet attachment region of each leaflet being coupled to the frame such that the leaflet attachment region adjacent the terminus of the leaflets when positioned adjacent to one another diverge relative to each other from a location away from the terminus to the terminus.

13. A prosthetic valve defining an inflow direction into the prosthetic valve and an outflow direction out of the prosthetic valve in operation, the prosthetic valve comprising:

a frame; and a plurality of leaflets including a first leaflet, a second leaflet, and a third leaflet, each leaflet having a leaflet attachment region and a free edge opposite a base edge, wherein the base edge and the free edge of each leaflet are at least substantially parallel when viewed as a flat profile, wherein the base edge of each leaflet is shorter than the free edge, wherein the leaflet attachment region is coupled to the frame, wherein each leaflet comprises a commissure tab adjacent the free edge, wherein each commissure tab comprises a plurality of apertures, and wherein each of the commissure tabs is divergent in the outflow direction.

14. The prosthetic valve of claim 13, wherein the leaflet attachment regions of the leaflets are divergent in the outflow direction and comprise a plurality of apertures.

* * * * *